US009090527B2

(12) United States Patent
Senda et al.

(10) Patent No.: US 9,090,527 B2
(45) Date of Patent: *Jul. 28, 2015

(54) METHOD FOR PRODUCING TRANSITION METAL COMPLEX, CATALYST FOR TRIMERIZATION, METHOD FOR PRODUCING 1-HEXENE, METHOD FOR PRODUCING SUBSTITUTED CYCLOPENTADIENE COMPOUND (2)

(75) Inventors: Taichi Senda, Ichihara (JP); Masaya Tanimoto, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/007,692

(22) PCT Filed: Mar. 29, 2012

(86) PCT No.: PCT/JP2012/059283
§ 371 (c)(1),
(2), (4) Date: Sep. 26, 2013

(87) PCT Pub. No.: WO2012/133925
PCT Pub. Date: Oct. 4, 2012

(65) Prior Publication Data
US 2014/0018565 A1 Jan. 16, 2014

(30) Foreign Application Priority Data
Mar. 29, 2011 (JP) ................ 2011-071902

(51) Int. Cl.
*C07F 17/00* (2006.01)
*C07C 2/34* (2006.01)
*B01J 31/22* (2006.01)

(52) U.S. Cl.
CPC .............. *C07C 2/34* (2013.01); *B01J 31/2295* (2013.01); *C07F 17/00* (2013.01); *B01J 2231/20* (2013.01); *B01J 2531/46* (2013.01); *B01J 2531/48* (2013.01); *B01J 2531/49* (2013.01); *C07C 2531/14* (2013.01); *C07C 2531/22* (2013.01)

(58) Field of Classification Search
CPC ... C07F 17/00; B01J 31/2295; B01J 2531/46; B01J 2531/48; B01J 2531/49; B01J 2231/20; C07C 2/34; C07C 2531/14; C07C 2531/22
USPC ............ 502/103, 152, 155, 153; 556/11, 489; 585/511
See application file for complete search history.

(56) References Cited

U.S. PATENT DOCUMENTS 5,712,354 A 1/1998 Boncella et al.
6,121,402 A 9/2000 Machida et al.

(Continued)

FOREIGN PATENT DOCUMENTS

CN 1193323 A 9/1998
CN 1433433 A 7/2003
(Continued)

OTHER PUBLICATIONS

Int'l Search Report issued Jun. 26, 2012 in Int'l Application No. PCT/JP2012/059283.
Deckers et al, "Catalytic Trimerization of Ethene with Highly Active Cyclopentadienyl—Arene Titanium Catalysts," Organometallics, vol. 21, pp. 5122-5135 (2002).
Sai Mannshausen et al, "Half-sandwich complexes of titanium and zirconium with pendant phenyl substituents. The influence of ansa-aryl coordination on the polymerisation activity of half-sandwich catalysts," Journal of Organometallic Chemistry, vol. 592, pp. 84-94 (1999).
Int'l Search Report issued Oct. 26, 2010 in Intl Application No. PCT/JP2010/067127.

(Continued)

*Primary Examiner* — Porfirio Nazario Gonzalez
(74) *Attorney, Agent, or Firm* — Panitch Schwarze Belisario & Nadel LLP

(57) ABSTRACT

A silicon-bridged Cp-Ar transition metal complex serves as a catalytic component capable of efficiently and highly selectively producing 1-hexene through trimerization reaction of ethylene. The transition metal complex is represented by formula (1):

wherein M represents a transition metal atom of Group 4 of the Periodic Table of the Elements; $X^1, X^2, X^3, R^1, R^2, R^3, R^4, R^5, R^6, R^7, R^8$, and $R^9$ each independently represent a hydrogen atom, a halogen atom, an alkyl group having 1 to 20 carbon atoms, an alkoxy group having 1 to 20 carbon atoms, an aryl group having 6 to 20 carbon atoms, an aryloxy group having 6 to 20 carbon atoms, an aralkyl group having 7 to 20 carbon atoms, and an aralkyloxy group having 7 to 20 carbon atoms, and wherein each of the groups may have a halogen atom as a substituent.

14 Claims, No Drawings

(56) References Cited

U.S. PATENT DOCUMENTS

| | | |
|---|---|---|
| 6,329,478 B1 | 12/2001 | Katayama et al. |
| 7,163,907 B1 | 1/2007 | Canich et al. |
| 2004/0030082 A1 | 2/2004 | Iseki |
| 2004/0097772 A1 | 5/2004 | Deckers et al. |
| 2006/0089417 A1 | 4/2006 | Hisayama et al. |
| 2007/0244286 A1 | 10/2007 | Okamoto et al. |
| 2012/0184431 A1* | 7/2012 | Kawashima et al. ......... 502/117 |
| 2012/0184693 A1 | 7/2012 | Kawashima et al. |
| 2013/0005931 A1 | 1/2013 | Kawashima et al. |
| 2014/0012056 A1 | 1/2014 | Hishiya et al. |
| 2014/0018564 A1* | 1/2014 | Senda et al. .................... 556/11 |

FOREIGN PATENT DOCUMENTS

| | | |
|---|---|---|
| CN | 1448416 A | 10/2003 |
| CN | 1492847 A | 4/2004 |
| CN | 101050216 A | 10/2007 |
| EP | 0617044 A2 | 9/1994 |
| EP | 2045254 A1 | 4/2009 |
| JP | H07-082322 A | 3/1995 |
| JP | 09-087313 A | 3/1997 |
| JP | 2004-524959 A | 8/2004 |
| JP | 2005-248013 A | 9/2005 |
| JP | 2006-002057 A | 1/2006 |
| JP | 2006-504858 A | 2/2006 |
| JP | 2006-083370 A | 3/2006 |
| JP | 2006-152271 A | 6/2006 |
| JP | 2006-347899 A | 12/2006 |
| JP | 2008-546891 A | 12/2008 |
| WO | 9703992 A1 | 2/1997 |
| WO | 0148028 A1 | 7/2001 |
| WO | 02066404 A1 | 8/2002 |
| WO | 02066405 A1 | 8/2002 |
| WO | 2004046214 A2 | 6/2004 |
| WO | 2007002435 A1 | 1/2007 |
| WO | 2011040555 A1 | 4/2011 |
| WO | 2012/133937 A1 | 10/2012 |

OTHER PUBLICATIONS

Wang et al, "Catalytic Trimerization of Ethylene with Highly Active Half-sandwich Titanium Complexes Bearing Pendant p-Fluorophenyl Groups," Chinese Journal of Chemistry, vol. 24, pp. 1397-1401 (2006).

Ye et al, "A Tandem Catalytic System for the Synthesis of Ethylene-Hex-l-ene Copolymers from Ethylene Stock," Macromolecular Rapid Communications, vol. 25, pp. 647-652 (2004).

Alobaidi et al, "Direct Synthesis of Linear Low-Density Polyethylene of Ethylene/1-Hexene from Ethylene with a Tandem Catalytic System in a Single Reactor," Journal of Polymer Science Part A: Polymer Chemistry, vol. 42, pp. 4327-4336 (2004).

Hanaoka et al, "Synthesis and characterization of titanuim and zirconium complexes with silicone-bridged phenoxycyclopentadienyl ligands," Journal of Organometallic Chemistry, vol. 692, pp. 4059-4066 (2007).

Chen et al, "Reactions of SiH-Functionalized Cyclopentadienes with Metal Carbonyls," Organometallics, vol. 26, pp. 4212-4219 (2007).

Lukesova et al, "Synthesis and crystal structures of thermally stable titanocenes," Journal of Organometallic Chemistry, vol. 663, pp. 134-144 (2002).

Search Report issued Jul. 3, 2013 in CN Application No. 2010800541680.

Extended European Search Report issued Oct. 14, 2013 in EP Application No. 10820670.7.

Hitzbleck et al, "Half-sandwich dibenzyl complexes of scandium: Synthesis, structure, and styrene polymerization activity," Journal of Organometallic Chemistry, vol. 692, No. 21, pp. 4702-4707 (Sep. 14, 2007).

Sassmannshausen et al, "Models for Solvation of Zirconocene Cations: Synthesis, Reactivity, and Computational Studies of Phenylsilyl-Substituted Cationic and Dicationic Zirconocene Compounds," Organometallics, vol. 25, No. 11, pp. 2796-2805 (Apr. 22, 2006).

Office Action issued Jan. 22, 2014 in CN Application No. 201080054170.8.

Int'l Search Report issued Jun. 26, 2012 in Int'l Application No. PCT/JP2012/059282.

Office Action issued Nov. 20, 2013 in U.S. Appl. No. 13/498,980.

Office Action issued May 21, 2014 in U.S. Appl. No. 13/498,980.

Nabika et al, Kobunshi Ronbunshu, vol. 59, No. 6, pp. 382-387 (2002).

Office Action issued Jun. 6, 2014 in U.S. Appl. No. 14/007,218.

Office Action issued Sep. 26, 2014 in U.S. Appl. No. 13/498,980.

Office Action issued Sep. 4, 2014 in CN Application No. 201080054170.8.

Office Action issued Nov. 3, 2014 in CN Application No. 201280015878.1.

Int'l Search Report issued Jul. 10, 2012 in Int'l Applicaiton No. PCT/JP2012/059296.

Otten et al, "Versatile Coordination of Cyclopentadienyl-Arene Ligands and Its Role in Titanium-Catalyzed Ethylene Trimerization," Journal of the American Chemical Society, vol. 131, pp. 5298-5312 (2009).

Hagen et al, "Selective ethylene trimerization: A study into the mechanism and the reduction of PE formation," Journal of Molecular Catalysis A: Chemical 248, pp. 237-247 (2006).

Office Action issued Sep. 3, 2014 in CN Application No. 201280016301.2.

Extended European Search Report issued Nov. 25, 2014 in EP Application No. 12763507.6.

Bowen et al, "One electron oxidation of chromium N,N-bis(diarylphosphino)amine and bis(diarylphosphino)methane complexes relevant to ethene trimerisation and tetramerisation," Dalton Transactions, vol. 11, pp. 1160-1168 (2007).

English translation of an Office Action issued Feb. 15, 2015 in CN Application No. 201080054170.8.

Zaeni et al, Unsolvated [KFl(SiPh3)]n (Fl=fluorenyl): A supramolecular chain structure assembled exclusively through K...C-Pi-bonding. Journal of Organometallic Chemistry 696 (2011) 1935-1938.

Extended European Search Report issued Jan. 15, 2015 in EP 12764484.7.

Office Action issued Apr. 23, 2015 in CN App No. 201280016301.2.

* cited by examiner

METHOD FOR PRODUCING TRANSITION METAL COMPLEX, CATALYST FOR TRIMERIZATION, METHOD FOR PRODUCING 1-HEXENE, METHOD FOR PRODUCING SUBSTITUTED CYCLOPENTADIENE COMPOUND (2)

CROSS-REFERENCE TO RELATED APPLICATION

This application is a Section 371 of International Application No. PCT/JP2012/059283, filed Mar. 29, 2012, which was published in the English language on Oct. 4, 2012, under International Publication No. WO 2012/133925 A1, and the disclosure of which is incorporated herein by reference.

TECHNICAL FIELD

The present invention relates to a transition metal complex, a method for producing the transition metal complex, a catalyst for trimerization, a method for producing 1-hexene, a substituted cyclopentadiene compound, and a method for producing the substituted cyclopentadiene compound.

BACKGROUND ART

α-olefin is an industrially important raw material monomer that is produced by the oligomerization of ethylene using a metal catalyst. However, the oligomerization of ethylene usually gives α-olefin mixtures according to Schulz-Flory distribution. Therefore, the development of a catalyst system capable of selectively producing one kind of α-olefin is very important industrially.

For example, Patent Document 1 has reported that a half-metallocene titanium complex represented by the formula $(Cp-B(R)_nAr)TiR^1{}_3$ activated with an activating co-catalyst component works as a catalyst for selective trimerization of ethylene.

Among these catalysts for selective ethylene trimerization, a half-metallocene titanium complex (carbon-bridged Cp-Ar complex) comprising cyclopentadiene bonded to a substituted aryl group via a carbon atom, such as [1-(1-methyl-1-(3,5-dimethylphenyl)ethyl)-3-trimethylsilylcyclopentadienyl]titanium trichloride, has been reported to work as an efficient catalytic component for ethylene trimerization under conditions of 30° C. with MAO (methylaluminoxane) as an activating co-catalyst component (see e.g., Non-Patent Document 1). On the other hand, [dimethylphenylsilylcyclopentadienyl]titanium trichloride, which is a half-metallocene titanium complex (silicon-bridged Cp-Ar complex) comprising cyclopentadiene bonded to a substituted aryl group via a silicon atom, has been reported to have low catalytic activity in ethylene trimerization reaction under the same conditions as above and to also have low 1-hexene selectivity (see Non-Patent Document 1).

PRIOR ART

Patent Document

[Patent Document 1] JP-A-2004-524959

Non-Patent Document

[Non-Patent Document 1] Organometallics 2002, 21, 5122-5135.

SUMMARY OF THE INVENTION

Problem to be Solved by the Invention

Under such circumstances, an object of the present invention is to provide a novel silicon-bridged Cp-Ar transition metal complex that serves as a catalytic component capable of efficiently and highly selectively producing 1-hexene through the trimerization reaction of ethylene.

Means for Solving the Problem

Specifically, the 1st aspect of the present invention relates to a transition metal complex represented by formula (1):

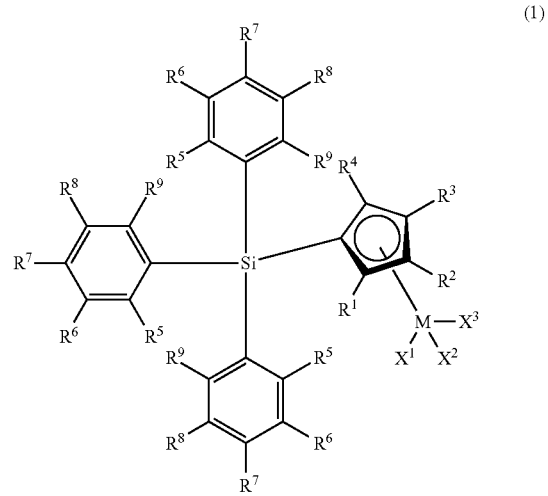

wherein.

M represents a transition metal atom of Group 4 of the Periodic Table of the Elements;

$X^1$, $X^2$, $X^3$, $R^1$, $R^2$, $R^3$, $R^4$, $R^5$, $R^6$, $R^7$, $R^8$ and $R^9$ each independently represent a hydrogen atom, a halogen atom, an alkyl group having 1 to 20 carbon atoms which may have a halogen atom as a substituent, an alkoxy group having 1 to 20 carbon atoms which may have a halogen atom as a substituent, an aryl group having 6 to 20 carbon atoms which may have a halogen atom as a substituent, an aryloxy group having 6 to 20 carbon atoms which may have a halogen atom as a substituent, an aralkyl group having 7 to 20 carbon atoms which may have a halogen atom as a substituent, an aralkyloxy group having 7 to 20 carbon atoms which may have a halogen atom as a substituent, a substituted silyl group represented by $-Si(R^{10})_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20, or a disubstituted amino group represented by $-N(R^{11})_2$, wherein the two $R^{11}$ moieties each independently represent a hydrocarbyl group or a halogenated hydrocarbyl group, and the total number of the carbon atoms in the two $R^{11}$ moieties is 2 to 20, and at least one of $R^5$, $R^6$, $R^7$, $R^8$ and $R^9$ is the alkoxy group, the aryloxy group, the aralkyloxy group, the substituted silyl group or the disubstituted amino group; or of $R^1$, $R^2$, $R^3$ and $R^4$, two group bonded to two adjoining carbon atoms may be bonded to each other to form a ring together with the two carbon atoms to which the two groups are bonded, and of $R^5$, $R^6$, $R^7$, $R^8$ and $R^9$, two group bonded to two adjoining carbon atoms may be bonded to each other to form a ring together with the two carbon atoms to which the two groups are bonded.

Further, the 2nd aspect of the present invention relates to a catalyst for trimerization which is obtained by bringing the transition metal complex into contact with an activating co-catalyst component.

Furthermore, the 3rd aspect of the present invention relates to a method for producing 1-hexene by ethylene trimerization in the presence of the catalyst for trimerization.

Moreover, the 4th aspect of the present invention relates to a method for producing the transition metal complex represented by formula (1).

Furthermore, the 5th aspect of the present invention relates to a substituted cyclopentadiene compound represented by formula (2):

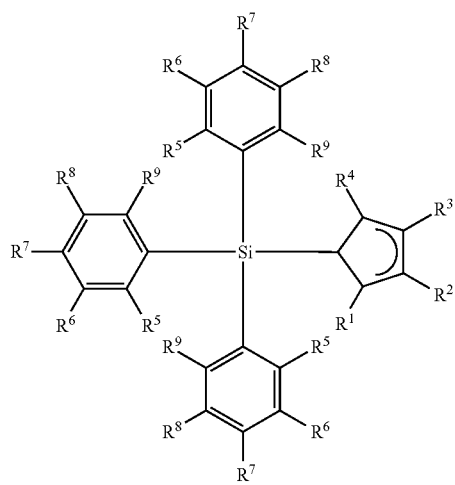

(2)

wherein
$R^1$, $R^2$, $R^3$, $R^4$, $R^5$, $R^6$, $R^7$, $R^8$ and $R^9$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by $—Si(R^{10})_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20, or
a disubstituted amino group represented by $—N(R^{11})_2$, wherein the two $R^{11}$ moieties each independently represent a hydrocarbyl group or a halogenated hydrocarbyl group, and the total number of the carbon atoms in the two $R^{11}$ moieties is 2 to 20, and at least one of $R^5$, $R^6$, $R^7$, $R^8$ and $R^9$ is the alkoxy group, the aryloxy group, the aralkyloxy group, the substituted silyl group or the disubstituted amino group; or of $R^1$, $R^2$, $R^3$ and $R^4$, two group bonded to two adjoining carbon atoms may be bonded to each other to form a ring together with the two carbon atoms to which the two groups are bonded, and of $R^5$, $R^6$, $R^7$, $R^8$ and $R^9$, two group bonded to two adjoining carbon atoms may be bonded to each other to form a ring together with the two carbon atoms to which the two groups are bonded, the moiety

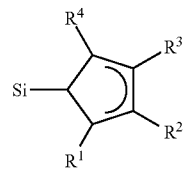

represents

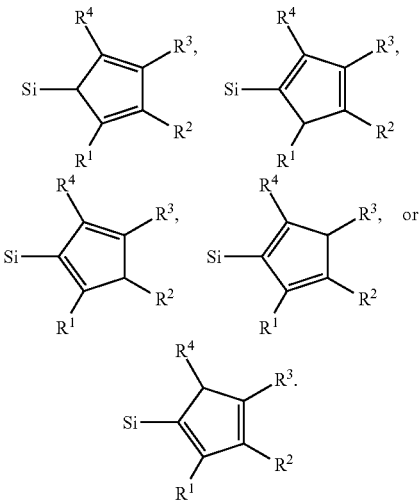

Moreover, the 6th aspect of the present invention relates to a method for producing the substituted cyclopentadiene compound represented by formula (2).

Advantages of the Invention

The present invention can provide a transition metal complex that is suitable as a catalyst capable of efficiently and highly selectively producing 1 hexene through the trimerization reaction of ethylene even under high temperature conditions.

EMBODIMENTS FOR CARRYING OUT THE INVENTION

In the present invention, the term "substituent" encompasses a halogen atom constituting a compound or a group.

Furthermore, in the present invention, substituted cyclopentadiene compounds represented by the general formulas (2) and (4) respectively have isomers differing in the double bond position of each cyclopentadiene ring. In the present invention, the substituted cyclopentadiene compounds refer to any of them or a mixture of them.

<Transition Metal Complex (1) (Catalytic Component for Trimerization)>

Hereinafter, the transition metal complex represented by formula (1) (hereinafter, abbreviated to a "transition metal complex (1)") will be described in detail.

In the transition metal complex (1), M represents an element of Group 4 of the Periodic Table of the Elements, and examples thereof include titanium, zirconium and hafnium atoms. Among them, a titanium atom is preferable.

In the transition metal complex (1), the substituents $R^1$, $R^2$, $R^3$, $R^4$, $R^5$, $R^6$, $R^7$, $R^8$, $R^9$, $X^1$, $X^2$ and $X^3$ are as defined above, and examples thereof are shown below.

The halogen atom is a fluorine, chlorine, bromine or iodine atom and is preferably a chlorine atom.

Examples of the "alkyl group having 1 to 20 carbon atoms" in the alkyl group having 1 to 20 carbon atoms which may have a halogen atom as a substituent include methyl, ethyl, n-propyl, isopropyl, n-butyl, sec-butyl, tert-butyl, n-pentyl, neopentyl, amyl, n-hexyl, heptyl, n-octyl, n-nonyl, n-decyl, n-dodecyl, n-tridecyl, tetradecyl, pentadecyl, hexadecyl, heptadecyl, octadecyl, nonadecyl and n-eicosyl groups. Of them, a preferable alkyl group is an alkyl group having 1 to 10 carbon atoms, and more preferable examples thereof can include methyl, ethyl, isopropyl, tert-butyl and amyl groups. Moreover, the phrase "may have a halogen atom as a substituent" in the "alkyl group which may have a halogen atom as a substituent" means that some or all hydrogen atoms in the alkyl group may be substituted by a halogen atom. Examples of the halogen atom are as described above. When the alkyl group has a halogen atom as a substituent, the number of its carbon atoms is preferably in the range of 1 to 20, more preferably in the range of 1 to 10. Preferable examples of the alkyl group having a halogen atom as a substituent can include fluoromethyl, difluoromethyl, trifluoromethyl, chloromethyl, dichloromethyl, trichloromethyl, bromomethyl, dibromomethyl, tribromomethyl, fluoroethyl, perfluoropropyl, perfluorobutyl, perfluoropentyl and perfluorohexyl groups.

Examples of the "aryl group having 6 to 20 carbon atoms" in the aryl group having 6 to 20 carbon atoms which may have a halogen atom as a substituent include phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, naphthyl and anthracenyl groups. Of them, a preferable aryl group is an aryl group having 6 to 10 carbon atoms, and more preferable examples thereof can include a phenyl group. Moreover, the phrase "may have a halogen atom as a substituent" in the "aryl group which may have a halogen atom as a substituent" means that some or all hydrogen atoms in the aryl group may be substituted by a halogen atom. Examples of the halogen atom are as described above. When the aryl group has a halogen atom as a substituent, the number of its carbon atoms is preferably in the range of 6 to 20, more preferably in the range of 6 to 10. Preferable examples of the aryl group having a halogen atom as a substituent can specifically include fluorophenyl, difluorophenyl, trifluorophenyl, tetrafluorophenyl, pentafluorophenyl, chlorophenyl, bromophenyl and iodophenyl groups.

Examples of the "aralkyl group having 7 to 20 carbon atoms" in the aralkyl group having 7 to 20 carbon atoms which may have a halogen atom as a substituent include benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (3,5-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, 1.5 (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, naphthylmethyl and anthracenylmethyl groups. Of them, a preferable aralkyl group is an aralkyl group having 7 to 10 carbon atoms, and more preferable examples thereof include a benzyl group. Moreover, the phrase "may have a halogen atom as a substituent" in the "aralkyl group which may have a halogen atom as a substituent" means that some or all hydrogen atoms in the aralkyl group may be substituted by a halogen atom. Examples of the halogen atom are as described above. When the aralkyl group has a halogen atom as a substituent, the number of its carbon atoms is preferably in the range of 7 to 20, more preferably in the range of 7 to 10.

Examples of the "alkoxy group having 1 to 20 carbon atoms" in the alkoxy group having 1 to 20 carbon atoms which may have a halogen atom as a substituent include methoxy, ethoxy, n-propoxy, isopropoxy, n-butoxy, sec-butoxy, tert-butoxy, n-pentyloxy, neopentyloxy, n-hexyloxy, n-octyloxy, n-nonyloxy, n-decyloxy, n-undecyloxy, n-dodecyloxy, tridecyloxy, tetradecyloxy, n-pentadecyloxy, hexadecyloxy, heptadecyloxy, octadecyloxy, nonadecyloxy and n-eicosyloxy groups. Of them, a preferable alkoxy group is an alkoxy group having 1 to 10 carbon atoms, and more preferable examples thereof include methoxy, ethoxy and tert-butoxy groups. Moreover, the phrase "may have a halogen atom as a substituent" in the "alkoxy group which may have a halogen atom as a substituent" means that some or all hydrogen atoms in the alkoxy group may be substituted by a halogen atom. Examples of the halogen atom are as described above. When the alkoxy group has a halogen atom as a substituent, the number of its carbon atoms is preferably in the range of 1 to 20, more preferably in the range of 1 to 10.

Examples of the "alkoxy group having 2 to 20 carbon atoms" in the alkoxy group having 2 to 20 carbon atoms which may have a halogen atom as a substituent include ethoxy, n-propoxy, isopropoxy, n-butoxy, sec-butoxy, tert-butoxy, n-pentyloxy, neopentyloxy, n-hexyloxy, n-octyloxy, n-nonyloxy, n-decyloxy, n-undecyloxy, n-dodecyloxy, tridecyloxy, tetradecyloxy, n-pentadecyloxy, hexadecyloxy, heptadecyloxy, octadecyloxy, nonadecyloxy and n-eicosyloxy groups. Of them, a preferable alkoxy group is an alkoxy group having 2 to 10 carbon atoms, and more preferable examples thereof include ethoxy and tert-butoxy groups. Moreover, the phrase "may have a halogen atom as a substituent" in the "alkoxy group which may have a halogen atom as a substituent" means that some or all hydrogen atoms in the alkoxy group may be substituted by a halogen atom. Examples of the halogen atom are as described above. When the alkoxy group has a halogen atom as a substituent, the number of its carbon atoms is preferably in the range of 2 to 20, more preferably in the range of 2 to 10.

Examples of the "aryloxy group having 6 to 20 carbon atoms" in the aryloxy group having 6 to 20 carbon atoms which may have a halogen atom as a substituent include phenoxy, 2-methylphenoxy, 3-methylphenoxy, 4-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2,3,4-trimethylphenoxy, 2,3,5-trimethylphenoxy, 2,3,6-trimethylphenoxy, 2,4,5-trimethylphenoxy, 2,4,6-trimethylphenoxy, 3,4,5-trimethylphenoxy, 2,3,4,5-tetramethylphenoxy, 2,3,4,6-tetramethylphenoxy, 2,3,5,6-tetramethylphenoxy, pentamethylphenoxy, ethylphenoxy, n-propylphenoxy, isopropylphenoxy, n-butylphenoxy, sec-butylphenoxy, tert-butylphenoxy, n-hexylphenoxy, n-octylphenoxy, n-decylphenoxy, n-tetradecylphenoxy, naphthoxy and anthracenoxy groups. Of them, a preferable aryloxy group is an aryloxy group having 6 to 10 carbon atoms, and more preferable examples thereof include phenoxy, 2-methylphenoxy, 3-methylphenoxy and 4-methylphenoxy groups. Moreover, the phrase "may have a halogen atom as a substituent" in the "aryloxy group which may have a halogen atom as a substituent" means that some or all hydrogen atoms in the aryloxy group may be substituted by a halogen atom. Examples of the halogen atom are as described above. When the aryloxy group has a halogen atom as a substituent, the number of its carbon atoms is preferably in the range of 6 to 20, more preferably in the range of 6 to 10.

Examples of the "aralkyloxy group having 7 to 20 carbon atoms" in the aralkyloxy group having 7 to 20 carbon atoms which may have a halogen atom as a substituent include benzyloxy, (2-methylphenyl)methoxy, (3-methylphenyl)methoxy, (4-methylphenyl)methoxy, (2,3-dimethylphenyl)methoxy, (2,4-dimethylphenyl)methoxy, (2,5-dimethylphenyl)methoxy, (2,6-dimethylphenyl)methoxy, (3,4-dimethylphenyl)methoxy, (3,5-dimethylphenyl)methoxy, (2,3,4-trimethylphenyl)methoxy, (2,3,5-trimethylphenyl)methoxy, (2,3,6-trimethylphenyl)methoxy, (2,4,5-trimethylphenyl)methoxy, (2,4,6-trimethylphenyl)methoxy, (3,4,5-trimethylphenyl)methoxy, (2,3,4,5-tetramethylphenyl)methoxy, (2,3,4,6-tetramethylphenyl)methoxy, (2,3,5,6-tetramethylphenyl)methoxy, (pentamethylphenyl)methoxy, (ethylphenyl)methoxy, (n-propylphenyl)methoxy, (isopropylphenyl)methoxy, (n-butylphenyl)methoxy, (sec-butylphenyl)methoxy, (tert-butylphenyl)methoxy, (n-hexylphenyl)methoxy, (n-octylphenyl)methoxy, (n-decylphenyl)methoxy, naphthylmethoxy and anthracenylmethoxy groups. Of them, a preferable aralkyloxy group is an aralkyloxy group having 7 to 10 carbon atoms, and more preferable examples thereof can include a benzyloxy group. Moreover, the phrase "may have a halogen atom as a substituent" in the "aralkyloxy group which may have a halogen atom as a substituent" means that some or all hydrogen atoms in the aralkyloxy group may be substituted by a halogen atom. Examples of the halogen atom are as described above. When the aralkyloxy group has a halogen atom as a substituent, the number of its carbon atoms is preferably in the range of 7 to 20, more preferably in the range of 7 to 10.

In the substituted silyl group represented by $-Si(R^{10})_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20, the $R^{10}$ moieties are each independently a hydrogen atom; a hydrocarbyl group such as an alkyl group having 1 to 10 carbon atoms (e.g., methyl, ethyl, n-propyl, isopropyl, n-butyl, sec-butyl, tert-butyl, isobutyl, n-pentyl, n-hexyl, cyclohexyl, n-heptyl, n-octyl, n-nonyl and n-decyl groups) and an aryl group (e.g., a phenyl group); or a halogenated hydrocarbyl group obtained by substituting some or all hydrogen atoms in the hydrocarbyl group by a halogen atom, and the total number of the carbon atoms in the three $R^{10}$ moieties is in the range of 1 to 20. The total number of the carbon atoms in these three $R^{10}$ moieties is preferably in the range of 3 to 18. Examples of the substituted silyl group include: monosubstituted silyl groups having one hydrocarbyl or halogenated hydrocarbyl group, such as methylsilyl, ethylsilyl and phenylsilyl groups, and groups obtained by substituting some or all hydrogen atoms in the hydrocarbyl groups of these groups by a halogen atom; disubstituted silyl groups having two hydrocarbyl and/or halogenated hydrocarbyl groups, such as dimethylsilyl, diethylsilyl and diphenylsilyl groups, and groups obtained by substituting some or all hydrogen atoms in the hydrocarbyl groups of these groups by a halogen atom; and trisubstituted silyl group having three hydrocarbyl and/or halogenated hydrocarbyl groups, such as trimethylsilyl, triethylsilyl, tri-n-propylsilyl, triisopropylsilyl, tri-n-butylsilyl, tri-sec-butylsilyl, tri-tert-butylsilyl, triisobutylsilyl, tert-butyl-dimethylsilyl, tri-n-pentylsilyl, tri-n-hexylsilyl, tricyclohexylsilyl and triphenylsilyl groups, and groups obtained by substituting some or all hydrogen atoms in the hydrocarbyl groups of these groups by a halogen atom. Of them, trisubstituted silyl groups are preferable, and trimethylsilyl, tert-butyldimethylsilyl and triphenylsilyl groups, and groups obtained by substituting some or all hydrogen atoms in these groups by a halogen atom are more preferable.

In the disubstituted amino group represented by $-N(R^{11})_2$, wherein the two $R^{11}$ moieties each independently represent a hydrocarbyl group or a halogenated hydrocarbyl group, and the total number of the carbon atoms in the two $R^{11}$ moieties is 2 to 20, the $R^{11}$ moieties each independently represent a hydrocarbyl group or a halogenated hydrocarbyl group, and the total number of the carbon atoms in the two $R^{11}$ moieties is in the range of 2 to 20, more preferably in the range of 2 to 10. The hydrocarbyl group and the halogenated hydrocarbyl group are the same as those described as a hydrocarbyl group and a halogenated hydrocarbyl group for the substituted silyl group. Moreover, these two $R^{11}$ moieties may be bonded to each other to form a ring together with the nitrogen atom to which the two $R^{11}$ moieties are bonded. Examples of such a disubstituted amino group include dimethylamino, diethylamino, di-n-propylamino, diisopropylamino, di-n-butylamino, di-sec-butylamino, di-tert-butylamino, di-isobutylamino, tert-butylisopropylanaino, di-n-hexylamino, di-n-octylamino, di-n-decylamino, diphenylamino, bistrimethylsilylamino, bis-tert-butyldimethylsilylamino, pyrrolyl, pyrrolidinyl, piperidinyl, carbazolyl, dihydroindolyl and dihydroisoindolyl groups, and groups obtained by substituting some or all hydrogen atoms in these groups by a halogen atom. Of them, dimethylamino, diethylamino, pyrrolidinyl and piperidinyl groups, and groups obtained by substituting some or all hydrogen atoms in these groups by a halogen atom are preferable.

Of $R^1$, $R^2$, $R^3$ and $R^4$, two groups bonded to two adjoining carbon atoms may be bonded to each other to form a ring together with the carbon atoms to which the two groups are bonded, and of $R^5$, $R^6$, $R^7$, $R^8$ and $R^9$, two groups bonded to two adjoining carbon atoms may be bonded to each other to form a ring together with the carbon atoms to which the two groups are bonded. In this context, the ring is a saturated or unsaturated hydrocarbyl ring substituted by a hydrocarbyl group having 1 to 20 carbon atoms, etc. Examples thereof include cyclopropane, cyclopropene, cyclobutane, cyclobutene, cyclopentane, cyclopentene, cyclohexane, cyclohexene, cycloheptene, cycloheptene, cyclooctane, cyclooctene, benzene, naphthalene, anthracene rings.

In the transition metal complex (1), at least one of $R^5$, $R^6$, $R^7$, $R^8$ and $R^9$ is an alkoxy group having 1 to 20 carbon atoms which may have a halogen atom as a substituent, an aryloxy group having 6 to 20 carbon atoms which may have a halogen atom as a substituent, an aralkyloxy group having 7 to 20 carbon atoms which may have a halogen atom as a substituent, a substituted silyl group represented by $—Si(R^{10})_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20, or a disubstituted amino group represented by $—N(R^{11})_2$, wherein the two $R^{11}$ moieties each independently represent a hydrocarbyl group or a halogenated hydrocarbyl group, and the total number of the carbon atoms in the two $R^{11}$ moieties is 2 to 20, with a substituted silyl group represented by $—Si(R^{10})_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20, being preferable.

In the transition metal complex (1), $X^1$, $X^2$ and $X^3$ are each independently preferably a halogen atom, an alkyl group having 1 to 20 carbon atoms, an alkoxy group having 1 to 20 carbon atoms, an aryloxy group having 6 to 20 carbon atoms, or an aralkyl group having 7 to 20 carbon atoms, more preferably a halogen atom and an alkyl group having 1 to 20 carbon atoms.

In formula (1), $R^6$ is preferably a substituted silyl group represented by $—Si(R^{10})_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20.

Further, in formula (1), $R^6$ and $R^8$ are preferably a substituted silyl group represented by $—Si(R^{10})_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20.

Furthermore, also preferable is the transition metal complex wherein, in formula (1), $R^6$ is a substituted silyl group represented by $—Si(R^{10})_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20, and $R^8$ is an alkyl group having 1 to 20 carbon atoms which may have a halogen atom as a substituent.

In the transition metal complex (1), $R^1$, $R^2$, $R^3$ and $R^4$ are each independently preferably a hydrogen atom, a halogen atom, an alkyl group having 1 to 20 carbon atoms, an aryl group having 6 to 20 carbon atoms or an aralkyl group having 7 to 20 carbon atoms, more preferably an alkyl group having 1 to 20 carbon atoms, even more preferably a methyl group.

Examples of $R^1$, $R^2$, $R^3$ and $R^4$ can include the following substructures represented by a substructural formula (6):

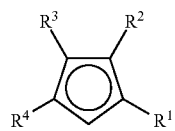

(6)

wherein $R^1$, $R^2$, $R^3$ and $R^4$ are as defined above:
cyclopentadienyl, methylcyclopentadienyl, ethylcyclopentadienyl, n-propylcyclopentadienyl, isopropylcyclopentadienyl, n-butylcyclopentadienyl, sec-butylcyclopentadienyl, tort-butylcyclopentadienyl, dimethylcyclopentadienyl, trimethylcyclopentadienyl, tetramethylcyclopentadienyl, phenylcyclopentadienyl, benzylcyclopentadienyl, indenyl, fluorenyl, tetrahydroindenyl, methyltetrahydroindenyl, dimethyltetrahydroindenyl and octahydrofluorenyl.

Of the cyclopentadienyl substructures exemplified above, a preferable cyclopentadienyl substructure is tetramethylcyclopentadienyl, etc.

Examples of a preferable combination of the moieties represented by $R^5$, $R^6$, $R^7$, $R^8$ and $R^9$ can include the following substructures represented by a substructural formula (7):

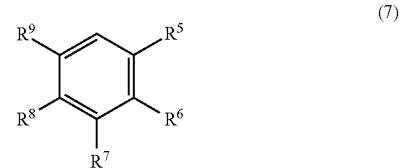

(7)

wherein $R^5$, $R^6$, $R^7$, $R^8$ and $R^9$ are as defined above:
trimethylsilylphenyl, methyl(trimethylsilyl)phenyl, dimethyl(trimethylsilyl)phenyl, trimethyl(trimethylsilyl)phenyl, tetramethyl(trimethylsilyl)phenyl, tert-butyl(trimethylsilyl)phenyl, di-tert-butyl(trimethylsilyl)phenyl, tert-butylmethyl(trimethylsilyl)phenyl, di(tert-butyl)methyl(trimethylsilyl)phenyl, chloro(trimethylsilyl)phenyl, dichloro(trimethylsilyl)phenyl, fluoro(trimethylsilyl)phenyl, bis(trifluoromethyl)(trimethylsilyl)phenyl, methoxy(trimethylsilyl)phenyl, bis(trimethylsilyl)phenyl, tris(trimethylsilyl)phenyl, methoxyphenyl, methoxy(methyl)phenyl, methoxy(dimethyl)phenyl,
methoxy(trimethyl)phenyl, methoxy(tetramethyl)phenyl, tert-butyl(methoxy)phenyl, di-tert-butyl(methoxy)phenyl, tert-butylmethyl(methoxy)phenyl, di(tert-butyl)methyl(methoxy)phenyl, chloro(methoxy)phenyl, dichloro(methoxy)phenyl, fluoro(methoxy)phenyl, bis(trifluoromethyl)(methoxy)phenyl, dimethoxyphenyl, trimethoxyphenyl,
dimethylaminophenyl, methyl(dimethylamino)phenyl, dimethyl(dimethylamino)phenyl, trimethyl(dimethylamino)phenyl, tetramethyl(dimethylamino)phenyl, tert-butyl(dimethylamino)phenyl, di-tert-butyl(dimethylamino)phenyl, tert-butylmethyl(dimethylamino)phenyl, di(tert-butyl)methyl(dimethylamino)phenyl, chloro(dimethylamino)phenyl, dichloro(dimethylamino)phenyl, fluoro(dimethylamino)phenyl, bis(trifluoromethyl)(dimethylamino)phenyl, bis(dimethylamino)phenyl, tris(dimethylamino)phenyl.

Of the substructures exemplified above, a preferable substructure is trimethylsilylphenyl, bis(trimethylsilyl)phenyl, methyl(trimethylsilyl)phenyl, dimethyl(trimethylsilyl)phenyl, etc.

Examples of the transition metal complex (1) include the following complexes:
titanium chloride complex such as [1-Tris(2-trimethylsilylphenyl)silyl-2,3,4,5-tetramethylcyclopentadienyl]titanium trichloride, [1-tris(3-trimethylsilylphenyl)silyl-2,3,4,5-tetramethylcyclopentadienyl]titanium trichloride, [1-tris(4-trimethylsilylphenyl)silyl-2,3,4,5-tetramethylcyclopentadienyl]titanium trichloride, [1-tris{2,3-bis(trimethylsilyl)phenyl}silyl-2,3,4,5-tetramethylcyclopentadienyl]titanium trichloride, [1-tris{2,4-bis(trimethylsilyl)phenyl}silyl-2,3,4,5-tetramethylcyclopentadienyl] titanium trichloride, [1-tris{2,5-bis(trimethylsilyl)phenyl}silyl-2,3,4,5-tetramethylcyclopentadienyl] titanium trichloride, [1-tris{2,6-bis(trimethylsilyl)phenyl}silyl-2,3,4,5-tetramethylcyclopentadienyl] titanium trichloride, [1-tris{3,5-bis(trimethylsilyl)phenyl}silyl-2,3,4,5-tetramethylcyclopentadienyl]

titanium trichloride, [1-tris{2,3,4-tris(trimethylsilyl)phenyl}silyl-2,3,4,5-tetramethylcyclopentadienyl]titanium trichloride, [1-tris{2,3,5-tris(trimethylsilyl)phenyl}silyl-2,3,4,5-tetramethylcyclopentadienyl]titanium trichloride, [1-tris{2,3,6-tris(trimethylsilyl)phenyl}silyl-2,3,4,5-tetramethylcyclopentadienyl]titanium trichloride, [1-tris{2,4,5-tris(trimethylsilyl)phenyl}silyl-2,3,4,5-tetramethylcyclopentadienyl]titanium trichloride, [1-tris{2,4,6-tris(trimethylsilyl)phenyl}silyl-2,3,4,5-tetramethylcyclopentadienyl]titanium trichloride, [1-tris{3,4,5-tris(trimethylsilyl)phenyl}silyl-2,3,4,5-tetramethylcyclopentadienyl]titanium trichloride, [1-tris{2,3,4,5-tetrakis(trimethylsilyl)phenyl}silyl-2,3,4,5-tetramethylcyclopentadienyl]titanium trichloride, [1-tris{2,3,4,6-tetrakis(trimethylsilyl)phenyl}silyl-2,3,4,5-tetramethylcyclopentadienyl]titanium trichloride, [1-tris{2,3,4,5,6-pentakis(trimethylsilyl)phenyl}silyl-2,3,4,5-tetramethylcyclopentadienyl]titanium trichloride,

[1-tris(2-methyl-3-trimethylsilyl-phenyl)silyl-2,3,4,5-tetramethylcyclopentadienyl]titanium trichloride, [1-tris(2-methyl-4-trimethylsilyl-phenyl)silyl-2,3,4,5-tetramethylcyclopentadienyl]titanium trichloride, [1-tris(2-methyl-5-trimethylsilyl-phenyl)silyl-2,3,4,5-tetramethylcyclopentadienyl]titanium trichloride, [1-tris(2-methyl-6-trimethylsilyl-phenyl)silyl-2,3,4,5-tetramethylcyclopentadienyl]titanium trichloride, [1-tris{2-methyl-3,4-bis(trimethylsilyl)-phenyl}silyl-2,3,4,5-tetramethylcyclopentadienyl]titanium trichloride, [1-tris{2-methyl-3,5-bis(trimethylsilyl)-phenyl}silyl-2,3,4,5-tetramethylcyclopentadienyl]titanium trichloride, [1-tris{2-methyl-3,6-bis(trimethylsilyl)-phenyl}silyl-2,3,4,5-tetramethylcyclopentadienyl]titanium trichloride, [1-tris{2-methyl-4,5-bis(trimethylsilyl)-phenyl}silyl-2,3,4,5-tetramethylcyclopentadienyl]titanium trichloride, [1-tris{2-methyl-4,6-bis(trimethylsilyl)-phenyl}silyl-2,3,4,5-tetramethylcyclopentadienyl]titanium trichloride, [1-tris{2-methyl-5,6-bis(trimethylsilyl)-phenyl}silyl-2,3,4,5-tetramethylcyclopentadienyl]titanium trichloride, [1-tris{2-methyl-3,4,5-tris(trimethylsilyl)-phenyl}silyl-2,3,4,5-tetramethylcyclopentadienyl]titanium trichloride, [1-tris{2-methyl-3,4,6-tris(trimethylsilyl)-phenyl}silyl-2,3,4,5-tetramethylcyclopentadienyl]titanium trichloride, [1-tris{2-methyl-4,5,6-tris(trimethylsilyl)-phenyl}silyl-2,3,4,5-tetramethylcyclopentadienyl]titanium trichloride, [1-tris{2-methyl-3,4,5,6-tetrakis(trimethylsilyl)-phenyl}silyl-2,3,4,5-tetramethylcyclopentadienyl]titanium trichloride,

[1-tris(3-methyl-2-trimethylsilyl-phenyl)silyl-2,3,4,5-tetramethylcyclopentadienyl]titanium trichloride, [1-tris(3-methyl-4-trimethylsilyl-phenyl)silyl-2,3,4,5-tetramethylcyclopentadienyl]titanium trichloride, [1-tris(3-methyl-5-trimethylsilyl-phenyl)silyl-2,3,4,5-tetramethylcyclopentadienyl]titanium trichloride, [1-tris(3-methyl-6-trimethylsilyl-phenyl)silyl-2,3,4,5-tetramethylcyclopentadienyl]titanium trichloride, [1-tris{3-methyl-2,4-bis(trimethylsilyl)-phenyl}silyl-2,3,4,5-tetramethylcyclopentadienyl]titanium trichloride, [1-tris{3-methyl-2,5-bis(trimethylsilyl)-phenyl}silyl-2,3,4,5-tetramethylcyclopentadienyl]titanium trichloride, [1-tris{3-methyl-2,6-bis(trimethylsilyl)-phenyl}silyl-2,3,4,5-tetramethylcyclopentadienyl]titanium trichloride, [1-tris{3-methyl-4,5-bis(trimethylsilyl)-phenyl}silyl-2,3,4,5-tetramethylcyclopentadienyl]titanium trichloride, [1-tris{3-methyl-4,6-bis(trimethylsilyl)-phenyl}silyl-2,3,4,5-tetramethylcyclopentadienyl]titanium trichloride, [1-tris{3-methyl-5,6-bis(trimethylsilyl)-phenyl}silyl-2,3,4,5-tetramethylcyclopentadienyl]titanium trichloride, [1-tris{3-methyl-2,4,5-tris(trimethylsilyl)-phenyl}silyl-2,3,4,5-tetramethylcyclopentadienyl]titanium trichloride, [1-tris{3-methyl-2,4,6-tris(trimethylsilyl)-phenyl}silyl-2,3,4,5-tetramethylcyclopentadienyl]titanium trichloride, [1-tris{3-methyl-4,5,6-tris(trimethylsilyl)-phenyl}silyl-2,3,4,5-tetramethylcyclopentadienyl]titanium trichloride, [1-tris{3-methyl-2,4,5,6-tetrakis(trimethylsilyl)-phenyl}silyl-2,3,4,5-tetramethylcyclopentadienyl]titanium trichloride,

[1-tris(4-methyl-2-trimethylsilyl-phenyl)silyl-2,3,4,5-tetramethylcyclopentadienyl]titanium trichloride, [1-tris(4-methyl-3-trimethylsilyl-phenyl)silyl-2,3,4,5-tetramethylcyclopentadienyl]titanium trichloride, [1-tris{4-methyl-2,3-bis(trimethylsilyl)-phenyl}silyl-2,3,4,5-tetramethylcyclopentadienyl]titanium trichloride, [1-tris{4-methyl-2,5-bis(trimethylsilyl)-phenyl}silyl-2,3,4,5-tetramethylcyclopentadienyl]titanium trichloride, [1-tris{4-methyl-2,6-bis(trimethylsilyl)-phenyl}silyl-2,3,4,5-tetramethylcyclopentadienyl]titanium trichloride, [1-tris{4-methyl-3,5-bis(trimethylsilyl)-phenyl}silyl-2,3,4,5-tetramethylcyclopentadienyl]titanium trichloride, [1-tris{4-methyl-2,3,5-tris(trimethylsilyl)-phenyl}silyl-2,3,4,5-tetramethylcyclopentadienyl]titanium trichloride, [1-tris{4-methyl-2,3,6-tris(trimethylsilyl)-phenyl}silyl-2,3,4,5-tetramethylcyclopentadienyl]titanium trichloride, [1-tris{4-methyl-2,3,5,6-tetrakis(trimethylsilyl)-phenyl}silyl-2,3,4,5-tetramethylcyclopentadienyl]titanium trichloride,

[1-tris(2,3-dimethyl-4-trimethylsilyl-phenyl)silyl-2,3,4,5-tetramethylcyclopentadienyl]titanium trichloride, [1-tris(2,3-dimethyl-5-trimethylsilyl-phenyl)silyl-2,3,4,5-tetramethylcyclopentadienyl]titanium trichloride, [1-tris(2,3-dimethyl-5-trimethylsilyl-phenyl)silyl-2,3,4,5-tetramethylcyclopentadienyl]titanium trichloride, [1-tris{2,3-dimethyl-4,5-bis(trimethylsilyl)-phenyl)silyl-2,3,4,5-tetramethylcyclopentadienyl]titanium trichloride, [1-tris{2,3-dimethyl-4,6-bis(trimethylsilyl)-phenyl)silyl-2,3,4,5-tetramethylcyclopentadienyl]titanium trichloride, [1-tris{2,3-dimethyl-5,6-bis(trimethylsilyl)-phenyl)silyl-2,3,4,5-tetramethylcyclopentadienyl]titanium trichloride, [1-tris{2,3-dimethyl-4,5,6-tris(trimethylsilyl)-phenyl)silyl-2,3,4,5-tetramethylcyclopentadienyl]titanium trichloride,

[1-tris(2,4-dimethyl-3-trimethylsilyl-phenyl)silyl-2,3,4,5-tetramethylcyclopentadienyl]titanium trichloride, [1-tris(2,4-dimethyl-5-trimethylsilyl-phenyl)silyl-2,3,4,5-tetramethylcyclopentadienyl]titanium trichloride, [1-tris(2,4-dimethyl-6-trimethylsilyl-phenyl)silyl-2,3,4,5-tetramethylcyclopentadienyl]titanium trichloride, [1-tris{2,4-dimethyl-3,5-bis(trimethylsilyl)-phenyl}silyl-2,3,4,5-tetramethylcyclopentadienyl]titanium trichloride, [1-tris{2,4-dimethyl-3,6-bis(trimethylsilyl)-phenyl}silyl-2,3,4,5-tetramethylcyclopentadienyl]titanium trichloride, [1-tris{2,4-dimethyl-5,6-bis(trimethylsilyl)-phenyl}silyl-2,3,4,5-tetramethylcyclopentadienyl]titanium trichloride, [1-tris{2,4-dimethyl-3,5,6-tris(trimethylsilyl)-phenyl}silyl-2,3,4,5-tetramethylcyclopentadienyl]titanium trichloride,

[1-tris(2,5-dimethyl-3-trimethylsilyl-phenyl)silyl-2,3,4,5-tetramethylcyclopentadienyl]titanium trichloride, [1-tris(2,5-dimethyl-4-trimethylsilyl-phenyl)silyl-2,3,4,5-tetramethylcyclopentadienyl]titanium trichloride, [1-tris(2,5-dimethyl-6-trimethylsilyl-phenyl)silyl-2,3,4,5-tetramethylcyclopentadienyl]titanium trichloride, [1-tris{2,5-dimethyl-3,4-bis(trimethylsilyl)-phenyl}silyl-2,3,4,5-tetramethylcyclopentadienyl]titanium trichloride,

[1-tris{2,5-dimethyl-3,6-bis(trimethylsilyl)-phenyl}silyl-2,3,4,5-tetramethylcyclopentadienyl]titanium trichloride, [1-tris{2,5-dimethyl-4,6-bis(trimethylsilyl)-phenyl}silyl-2,3,4,5-tetramethylcyclopentadienyl]titanium trichloride, [1-tris{2,5-dimethyl-3,4,6-tris(trimethyl silyl)-phenyl}silyl-2,3,4,5-tetramethylcyclopentadienyl]titanium trichloride,

[1-tris(2,6-dimethyl-3-trimethylsilyl-phenyl)silyl-2,3,4,5-tetramethylcyclopentadienyl]titanium trichloride, [1-tris(2,6-dimethyl-4-trimethylsilyl-phenyl)silyl-2,3,4,5-tetramethylcyclopentadienyl]titanium trichloride, [1-tris{2,6-dimethyl-3,4-bis(trimethylsilyl)-phenyl}silyl-2,3,4,5-tetramethylcyclopentadienyl]titanium trichloride, [1-tris{2,6-dimethyl-3,5-bis(trimethylsilyl)-phenyl}silyl-2,3,4,5-tetramethylcyclopentadienyl]titanium trichloride, [1-tris{2,6-dimethyl-3,4,5-tris(trimethylsilyl)-phenyl}silyl-2,3,4,5-tetramethylcyclopentadienyl]titanium trichloride,

[1-tris(3,4-dimethyl-2-trimethylsilyl-phenyl)silyl-2,3,4,5-tetramethylcyclopentadienyl]titanium trichloride, [1-tris(3,4-dimethyl-5-trimethylsilyl-phenyl)silyl-2,3,4,5-tetramethylcyclopentadienyl]titanium trichloride, [1-tris(3,4-dimethyl-6-trimethylsilyl-phenyl)silyl-2,3,4,5-tetramethylcyclopentadienyl]titanium trichloride, [1-tris{3,4-dimethyl-2,5-bis(trimethylsilyl)-phenyl}silyl-2,3,4,5-tetramethylcyclopentadienyl]titanium trichloride, [1-tris{3,4-dimethyl-2,6-bis(trimethylsilyl)-phenyl}silyl-2,3,4,5-tetramethylcyclopentadienyl]titanium trichloride, [1-tris{3,4-dimethyl-5,6-bis(trimethylsilyl)-phenyl}silyl-2,3,4,5-tetramethylcyclopentadienyl]titanium trichloride, [1-tris{3,4-dimethyl-2,5,6-tris(trimethylsilyl)-phenyl}silyl-2,3,4,5-tetramethylcyclopentadienyl]titanium trichloride,

[1-tris(3,5-dimethyl-2-trimethylsilyl-phenyl)silyl-2,3,4,5-tetramethylcyclopentadienyl]titanium trichloride, [1-tris(3,5-dimethyl-4-trimethylsilyl-phenyl)silyl-2,3,4,5-tetramethylcyclopentadienyl]titanium trichloride, [1-tris{3,5-dimethyl-2,4-bis(trimethylsilyl)-phenyl}silyl-2,3,4,5-tetramethylcyclopentadienyl]titanium trichloride, [1-tris{3,5-dimethyl-2,4,6-tris(trimethylsilyl)-phenyl}silyl-2,3,4,5-tetramethylcyclopentadienyl]titanium trichloride,

[1-tris(2-methoxyphenyl)silyl-2,3,4,5-tetramethylcyclopentadienyl]titanium trichloride, [1-tris(3-methoxy-phenyl)silyl-2,3,4,5-tetramethylcyclopentadienyl]titanium trichloride, [1-tris(4-methoxy-phenyl)silyl-2,3,4,5-tetramethylcyclopentadienyl]titanium trichloride, [1-tris{2,3-dimethoxy-phenyl}silyl-2,3,4,5-tetramethylcyclopentadienyl]titanium trichloride, [1-tris{2,4-dimethoxy-phenyl}silyl-2,3,4,5-tetramethylcyclopentadienyl]titanium trichloride, [1-tris{2,5-dimethoxy-phenyl}silyl-2,3,4,5-tetramethylcyclopentadienyl]titanium trichloride, [1-tris{2,6-dimethoxy-phenyl}silyl-2,3,4,5-tetramethylcyclopentadienyl]titanium trichloride, [1-tris{3,5-dimethoxy-phenyl}silyl-2,3,4,5-tetramethylcyclopentadienyl]titanium trichloride, [1-tris{2,3,4-trimethoxy-phenyl}silyl-2,3,4,5-tetramethylcyclopentadienyl]titanium trichloride, [1-tris{2,3,5-trimethoxy-phenyl}silyl-2,3,4,5-tetramethylcyclopentadienyl]titanium trichloride, [1-tris{2,3,6-trimethoxy-phenyl}silyl-2,3,4,5-tetramethylcyclopentadienyl]titanium trichloride, [1-tris{2,4,5-trimethoxy-phenyl}silyl-2,3,4,5-tetramethylcyclopentadienyl]titanium trichloride, [1-tris{2,4,6-trimethoxy-phenyl}silyl-2,3,4,5-tetramethylcyclopentadienyl]titanium trichloride, [1-tris{3,4,5-trimethoxy-phenyl}silyl-2,3,4,5-tetramethylcyclopentadienyl]titanium trichloride, [1-tris{2,3,4,5-tetramethoxy-phenyl}silyl-2,3,4,5-tetramethylcyclopentadienyl]titanium trichloride, [1-tris{2,3,4,6-tetramethoxy-phenyl}silyl-2,3,4,5-tetramethylcyclopentadienyl]titanium trichloride, [1-tris{2,3,4,5,6-pentamethoxy-phenyl}silyl-2,3,4,5-tetramethylcyclopentadienyl]titanium trichloride,

[1-tris(2-methyl-3-methoxy-phenyl)silyl-2,3,4,5-tetramethylcyclopentadienyl]titanium trichloride, [1-tris(2-methyl-4-methoxy-phenyl)silyl-2,3,4,5-tetramethylcyclopentadienyl]titanium trichloride, [1-tris(2-methyl-5-methoxy-phenyl)silyl-2,3,4,5-tetramethylcyclopentadienyl]titanium trichloride, [1-tris(2-methyl-6-methoxy-phenyl)silyl-2,3,4,5-tetramethylcyclopentadienyl]titanium trichloride, [1-tris{2-methyl-3,4-dimethoxy-phenyl}silyl-2,3,4,5-tetramethylcyclopentadienyl]titanium trichloride, [1-tris{2-methyl-3,5-dimethoxy-phenyl}silyl-2,3,4,5-tetramethylcyclopentadienyl]titanium trichloride, [1-tris{2-methyl-3,6-dimethoxy-phenyl}silyl-2,3,4,5-tetramethylcyclopentadienyl]titanium trichloride, [1-tris{2-methyl-4,5-dimethoxy-phenyl}silyl-2,3,4,5-tetramethylcyclopentadienyl]titanium trichloride, [1-tris{2-methyl-4,6-dimethoxy-phenyl}silyl-2,3,4,5-tetramethylcyclopentadienyl]titanium trichloride, [1-tris{2-methyl-5,6-dimethoxy-phenyl}silyl-2,3,4,5-tetramethylcyclopentadienyl]titanium trichloride, [1-tris{2-methyl-3,4,5-trimethoxy-phenyl}silyl-2,3,4,5-tetramethylcyclopentadienyl]titanium trichloride, [1-tris{2-methyl-3,4,6-trimethoxy-phenyl}silyl-2,3,4,5-tetramethylcyclopentadienyl]titanium trichloride, [1-tris{2-methyl-4,5,6-trimethoxy-phenyl}silyl-2,3,4,5-tetramethylcyclopentadienyl]titanium trichloride, [1-tris{2-methyl-3,4,5,6-tetramethoxy-phenyl}silyl-2,3,4,5-tetramethylcyclopentadienyl]titanium trichloride,

[1-tris(3-methyl-2-methoxy-phenyl)silyl-2,3,4,5-tetramethylcyclopentadienyl]titanium trichloride, [1-tris(3-methyl-4-methoxy-phenyl)silyl-2,3,4,5-tetramethylcyclopentadienyl]titanium trichloride, [1-tris(3-methyl-5-methoxy-phenyl)silyl-2,3,4,5-tetramethylcyclopentadienyl]titanium trichloride, [1-tris(3-methyl-6-methoxy-phenyl)silyl-2,3,4,5-tetramethylcyclopentadienyl]titanium trichloride, [1-tris{3-methyl-2,4-dimethoxy-phenyl}silyl-2,3,4,5-tetramethylcyclopentadienyl]titanium trichloride, [1-tris{3-methyl-2,5-dimethoxy-phenyl}silyl-2,3,4,5-tetramethylcyclopentadienyl]titanium trichloride, [1-tris{3-methyl-2,6-dimethoxy-phenyl}silyl-2,3,4,5-tetramethylcyclopentadienyl]titanium trichloride, [1-tris{3-methyl-4,5-dimethoxy-phenyl}silyl-2,3,4,5-tetramethylcyclopentadienyl]titanium trichloride, [1-tris{3-methyl-4,6-dimethoxy-phenyl}silyl-2,3,4,5-tetramethylcyclopentadienyl]titanium trichloride, [1-tris{3-methyl-5,6-dimethoxy-phenyl}silyl-2,3,4,5-tetramethylcyclopentadienyl]titanium trichloride, [1-tris{3-methyl-2,4,5-trimethoxy-phenyl}silyl-2,3,4,5-tetramethylcyclopentadienyl]titanium trichloride, [1-tris{3-methyl-2,4,6-trimethoxy-phenyl}silyl-2,3,4,5-tetramethylcyclopentadienyl]titanium trichloride, [1-tris{3-methyl-4,5,6-trimethoxy-phenyl}silyl-2,3,4,5-tetramethylcyclopentadienyl]titanium trichloride, [1-tris{3-methyl-2,4,5,6-tetramethoxy-phenyl}silyl-2,3,4,5-tetramethylcyclopentadienyl]titanium trichloride,

[1-tris(4-methyl-2-methoxy-phenyl)silyl-2,3,4,5-tetramethylcyclopentadienyl]titanium trichloride, [1-tris(4-methyl-3-methoxy-phenyl)silyl-2,3,4,5-tetramethylcyclopentadienyl]titanium trichloride, [1-tris{4-methyl-2,3-dimethoxy-phenyl}silyl-2,3,4,5-tetramethylcyclopentadienyl]titanium trichloride,

[1-tris{4-methyl-2,5-dimethoxy-phenyl}silyl-2,3,4,5-tetramethylcyclopentadienyl]titanium trichloride, [1-tris{4-methyl-2,6-dimethoxy-phenyl}silyl-2,3,4,5-tetramethylcyclopentadienyl]titanium trichloride, [1-tris{4-methyl-3,5-dimethoxy-phenyl}silyl-2,3,4,5-tetramethylcyclopentadienyl]titanium trichloride, [1-tris{4-methyl-2,3,5-trimethoxy-phenyl}silyl-2,3,4,5-tetramethylcyclopentadienyl]titanium trichloride, [1-tris{4-methyl-2,3,6-trimethoxy-phenyl}silyl-2,3,4,5-tetramethylcyclopentadienyl]titanium trichloride, [1-tris{4-methyl-2,3,5,6-tetramethoxy-phenyl}silyl-2,3,4,5-tetramethylcyclopentadienyl]titanium trichloride,

[1-tris(2,3-dimethyl-4-methoxy-phenyl)silyl-2,3,4,5-tetramethylcyclopentadienyl]titanium trichloride, [1-tris(2,3-dimethyl-5-methoxy-phenyl)silyl-2,3,4,5-tetramethylcyclopentadienyl]titanium trichloride, [1-tris(2,3-dimethyl-5-methoxy-phenyl)silyl-2,3,4,5-tetramethylcyclopentadienyl]titanium trichloride, [1-tris{2,3-dimethyl-4,5-dimethoxy-phenyl)silyl-2,3,4,5-tetramethylcyclopentadienyl]titanium trichloride, [1-tris{2,3-dimethyl-4,6-dimethoxy-phenyl)silyl-2,3,4,5-tetramethylcyclopentadienyl]titanium trichloride, [1-tris{2,3-dimethyl-5,6-dimethoxy-phenyl)silyl-2,3,4,5-tetramethylcyclopentadienyl]titanium trichloride, [1-tris{2,3-dimethyl-4,5,6-trimethoxy-phenyl)silyl-2,3,4,5-tetramethylcyclopentadienyl]titanium trichloride,

[1-tris(2,4-dimethyl-3-methoxy-phenyl)silyl-2,3,4,5-tetramethylcyclopentadienyl]titanium trichloride, [1-tris(2,4-dimethyl-5-methoxy-phenyl)silyl-2,3,4,5-tetramethylcyclopentadienyl]titanium trichloride, [1-tris(2,4-dimethyl-6-methoxy-phenyl)silyl-2,3,4,5-tetramethylcyclopentadienyl]titanium trichloride, [1-tris{2,4-dimethyl-3,5-dimethoxy-phenyl}silyl-2,3,4,5-tetramethylcyclopentadienyl]titanium trichloride, [1-tris{2,4-dimethyl-3,6-dimethoxy-phenyl}silyl-2,3,4,5-tetramethylcyclopentadienyl]titanium trichloride, [1-tris{2,4-dimethyl-5,6-dimethoxy-phenyl}silyl-2,3,4,5-tetramethylcyclopentadienyl]titanium trichloride, [1-tris{2,4-dimethyl-3,5,6-trimethoxy-phenyl}silyl-2,3,4,5-tetramethylcyclopentadienyl]titanium trichloride,

[1-tris(2,5-dimethyl-3-methoxy-phenyl)silyl-2,3,4,5-tetramethylcyclopentadienyl]titanium trichloride, [1-tris(2,5-dimethyl-4-methoxy-phenyl)silyl-2,3,4,5-tetramethylcyclopentadienyl]titanium trichloride, [1-tris(2,5-dimethyl-6-methoxy-phenyl)silyl-2,3,4,5-tetramethylcyclopentadienyl]titanium trichloride, [1-tris{2,5-dimethyl-3,4-dimethoxy-phenyl}silyl-2,3,4,5-tetramethylcyclopentadienyl]titanium trichloride, [1-tris{2,5-dimethyl-3,6-dimethoxy-phenyl}silyl-2,3,4,5-tetramethylcyclopentadienyl]titanium trichloride, [1-tris{2,5-dimethyl-4,6-dimethoxy-phenyl}silyl-2,3,4,5-tetramethylcyclopentadienyl]titanium trichloride, [1-tris{2,5-dimethyl-3,4,6-trimethoxy-phenyl}silyl-2,3,4,5-tetramethylcyclopentadienyl]titanium trichloride,

[1-tris(2,6-dimethyl-3-methoxy-phenyl)silyl-2,3,4,5-tetramethylcyclopentadienyl]titanium trichloride, [1-tris(2,6-dimethyl-4-methoxy-phenyl)silyl-2,3,4,5-tetramethylcyclopentadienyl]titanium trichloride, [1-tris{2,6-dimethyl-3,4-dimethoxy-phenyl}silyl-2,3,4,5-tetramethylcyclopentadienyl]titanium trichloride, [1-tris{2,6-dimethyl-3,5-dimethoxy-phenyl}silyl-2,3,4,5-tetramethylcyclopentadienyl]titanium trichloride, [1-tris{2,6-dimethyl-3,4,5-trimethoxy-phenyl}silyl-2,3,4,5-tetramethylcyclopentadienyl]titanium trichloride,

[1-tris(3,4-dimethyl-2-methoxy-phenyl)silyl-2,3,4,5-tetramethylcyclopentadienyl]titanium trichloride, [1-tris(3,4-dimethyl-5-methoxy-phenyl)silyl-2,3,4,5-tetramethylcyclopentadienyl]titanium trichloride, [1-tris(3,4-dimethyl-6-methoxy-phenyl)silyl-2,3,4,5-tetramethylcyclopentadienyl]titanium trichloride, [1-tris{3,4-dimethyl-2,5-dimethoxy-phenyl}silyl-2,3,4,5-tetramethylcyclopentadienyl]titanium trichloride, [1-tris{3,4-dimethyl-2,6-dimethoxy-phenyl}silyl-2,3,4,5-tetramethylcyclopentadienyl]titanium trichloride, [1-tris{3,4-dimethyl-5,6-dimethoxy-phenyl}silyl-2,3,4,5-tetramethylcyclopentadienyl]titanium trichloride, [1-tris{3,4-dimethyl-2,5,6-trimethoxy-phenyl}silyl-2,3,4,5-tetramethylcyclopentadienyl]titanium trichloride,

[1-tris(3,5-dimethyl-2-methoxy-phenyl)silyl-2,3,4,5-tetramethylcyclopentadienyl]titanium trichloride, [1-tris(3,5-dimethyl-4-methoxy-phenyl)silyl-2,3,4,5-tetramethylcyclopentadienyl]titanium trichloride, [1-tris{3,5-dimethyl-2,4-dimethoxy-phenyl}silyl-2,3,4,5-tetramethylcyclopentadienyl]titanium trichloride, [1-tris{3,5-dimethyl-2,4,6-trimethoxy-phenyl}silyl-2,3,4,5-tetramethylcyclopentadienyl]titanium trichloride,

[1-tris(2-dimethylamino-phenyl)silyl-2,3,4,5-tetramethylcyclopentadienyl]titanium trichloride, [1-tris(3-dimethylamino-phenyl)silyl-2,3,4,5-tetramethylcyclopentadienyl]titanium trichloride, [1-tris(4-dimethylamino-phenyl)silyl-2,3,4,5-tetramethylcyclopentadienyl]titanium trichloride, [1-tris{2,3-bis(dimethylamino)phenyl}silyl-2,3,4,5-tetramethylcyclopentadienyl]titanium trichloride, [1-tris{2,4-bis(dimethylamino)phenyl}silyl-2,3,4,5-tetramethylcyclopentadienyl]titanium trichloride, [1-tris{2,5-bis(dimethylamino)phenyl}silyl-2,3,4,5-tetramethylcyclopentadienyl]titanium trichloride, [1-tris{2,6-bis(dimethylamino)phenyl}silyl-2,3,4,5-tetramethylcyclopentadienyl]titanium trichloride, [1-tris{3,5-bis(dimethylamino)phenyl}silyl-2,3,4,5-tetramethylcyclopentadienyl]titanium trichloride, [1-tris{2,3,4-tris(dimethylamino)phenyl}silyl-2,3,4,5-tetramethylcyclopentadienyl]titanium trichloride, [1-tris{2,3,5-tris(dimethylamino)phenyl}silyl-2,3,4,5-tetramethylcyclopentadienyl]titanium trichloride, [1-tris{2,3,6-tris(dimethylamino)phenyl}silyl-2,3,4,5-tetramethylcyclopentadienyl]titanium trichloride, [1-tris{2,4,5-tris(dimethylamino)phenyl}silyl-2,3,4,5-tetramethylcyclopentadienyl]titanium trichloride, [1-tris{2,4,6-tris(dimethylamino)phenyl}silyl-2,3,4,5-tetramethylcyclopentadienyl]titanium trichloride, [1-tris{3,4,5-tris(dimethylamino)phenyl}silyl-2,3,4,5-tetramethylcyclopentadienyl]titanium trichloride, [1-tris{2,3,4,5-tetrakis(dimethylamino)phenyl}silyl-2,3,4,5-tetramethylcyclopentadienyl]titanium trichloride, [1-tris{2,3,4,6-tetrakis(dimethylamino)phenyl}silyl-2,3,4,5-tetramethylcyclopentadienyl]titanium trichloride, [1-tris{2,3,4,5,6-pentakis(dimethylamino)phenyl}silyl-2,3,4,5-tetramethylcyclopentadienyl]titanium trichloride,

[1-tris(2-methyl-3-dimethylamino-phenyl)silyl-2,3,4,5-tetramethylcyclopentadienyl]titanium trichloride, [1-tris(2-methyl-4-dimethylamino-phenyl)silyl-2,3,4,5-tetramethylcyclopentadienyl]titanium trichloride, [1-tris(2-methyl-5-dimethylamino-phenyl)silyl-2,3,4,5-tetramethylcyclopentadienyl]titanium trichloride, [1-tris(2-methyl-6-dimethylamino-phenyl)silyl-2,3,4,5-tetramethylcyclopentadienyl]titanium trichloride, [1-tris{2-methyl-3,4-bis(dimethylamino)-phenyl}silyl-2,3,4,5-tetramethylcyclopentadienyl]titanium trichloride, [1-tris{2-methyl-3,5-bis(dimethylamino)-phenyl}silyl-2,3,4,5-tetramethylcyclopentadienyl]titanium trichloride, [1-tris{2-methyl-3,6-bis(dimethylamino)-phenyl}silyl-2,3,4,5-tetramethylcyclopentadienyl]titanium trichloride, [1-tris{2-methyl-4,5-bis(dimethylamino)-phenyl}silyl-2, 3,4,5-tetramethylcyclopentadienyl]titanium trichloride, [1-tris{2-methyl-4,6-bis(dimethylamino)-phenyl}silyl-2,3,4,5-tetramethylcyclopentadienyl]titanium trichloride, [1-tris{2-methyl-5,6-bis(dimethylamino)-phenyl}silyl-2,3,4,5-tetramethylcyclopentadienyl]titanium trichloride, [1-tris{2-methyl-3,4,5-tris(dimethylamino)-phenyl}silyl-2,3,4,5-tetramethylcyclopentadienyl]titanium trichloride, [1-tris{2-methyl-3,4,6-tris(dimethylamino)-phenyl}silyl-2,3,4,5-tetramethylcyclopentadienyl]titanium trichloride, [1-tris{2-methyl-4,5,6-tris(dimethylamino)-phenyl}silyl-2,3,4,5-tetramethylcyclopentadienyl]titanium trichloride, [1-tris{2-methyl-3,4,5,6-tetrakis(dimethylamino)-phenyl}silyl-2,3,4,5-tetramethylcyclopentadienyl]titanium trichloride,

[1-tris(3-methyl-2-dimethylamino-phenyl)silyl-2,3,4,5-tetramethylcyclopentadienyl]titanium trichloride, [1-tris(3-methyl-4-dimethylamino-phenyl)silyl-2,3,4,5-tetramethylcyclopentadienyl]titanium trichloride, [1-tris(3-methyl-5-dimethylamino-phenyl)silyl-2,3,4,5-tetramethylcyclopentadienyl]titanium trichloride, [1-tris(3-methyl-6-dimethylamino-phenyl)silyl-2,3,4,5-tetramethylcyclopentadienyl]titanium trichloride, [1-tris{3-methyl-2,4-bis(dimethylamino)-phenyl}silyl-2,3,4,5-tetramethylcyclopentadienyl]titanium trichloride, [1-tris{3-methyl-2,5-bis(dimethylamino)-phenyl}silyl-2,3,4,5-tetramethylcyclopentadienyl]titanium trichloride, [1-tris{3-methyl-2,6-bis(dimethylamino)-phenyl}silyl-2,3,4,5-tetramethylcyclopentadienyl]titanium trichloride, [1-tris{3-methyl-4,5-bis(dimethylamino)-phenyl}silyl-2,3,4,5-tetramethylcyclopentadienyl]titanium trichloride, [1-tris{3-methyl-4,6-bis(dimethylamino)-phenyl}silyl-2,3,4,5-tetramethylcyclopentadienyl]titanium trichloride, [1-tris{3-methyl-5,6-bis(dimethylamino)-phenyl}silyl-2,3,4,5-tetramethylcyclopentadienyl]titanium trichloride, [1-tris{3-methyl-2,4,5-tris(dimethylamino)-phenyl}silyl-2,3,4,5-tetramethylcyclopentadienyl]titanium trichloride, [1-tris{3-methyl-2,4,6-tris(dimethylamino)-phenyl}silyl-2,3,4,5-tetramethylcyclopentadienyl]titanium trichloride, [1-tris{3-methyl-4,5,6-tris(dimethylamino)-phenyl}silyl-2,3,4,5-tetramethylcyclopentadienyl]titanium trichloride, [1-tris{3-methyl-2,4,5,6-tetrakis(dimethylamino)-phenyl}silyl-2,3,4,5-tetramethylcyclopentadienyl]titanium trichloride,

[1-tris(4-methyl-2-dimethylamino-phenyl)silyl-2,3,4,5-tetramethylcyclopentadienyl]titanium trichloride, [1-tris(4-methyl-3-dimethylamino-phenyl)silyl-2,3,4,5-tetramethylcyclopentadienyl]titanium trichloride, [1-tris{4-methyl-2,3-bis(dimethylamino)-phenyl}silyl-2,3,4,5-tetramethylcyclopentadienyl]titanium trichloride, [1-tris{4-methyl-2,5-bis(dimethylamino)-phenyl}silyl-2,3,4,5-tetramethylcyclopentadienyl]titanium trichloride, [1-tris{4-methyl-2,6-bis(dimethylamino)-phenyl}silyl-2,3,4,5-tetramethylcyclopentadienyl]titanium trichloride, [1-tris{4-methyl-3,5-bis(dimethylamino)-phenyl}silyl-2,3,4,5-tetramethylcyclopentadienyl]titanium trichloride, [1-tris{4-methyl-2,3,5-tris(dimethylamino)-phenyl}silyl-2,3,4,5-tetramethylcyclopentadienyl]titanium trichloride, [1-tris{4-methyl-2,3,6-tris(dimethylamino)-phenyl}silyl-2,3,4,5-tetramethylcyclopentadienyl]titanium trichloride, [1-tris{4-methyl-2,3,5,6-tetrakis(dimethylamino)-phenyl}silyl-2,3,4,5-tetramethylcyclopentadienyl]titanium trichloride,

[1-tris(2,3-dimethyl-4-dimethylamino-phenyl)silyl-2,3,4,5-tetramethylcyclopentadienyl]titanium trichloride, [1-tris(2,3-dimethyl-5-dimethylamino-phenyl)silyl-2,3,4,5-tetramethylcyclopentadienyl]titanium trichloride, [1-tris(2,3-dimethyl-5-dimethylamino-phenyl)silyl-2,3,4,5-tetramethylcyclopentadienyl]titanium trichloride, [1-tris{2,3-dimethyl-4,5-bis(dimethylamino)-phenyl)silyl-2,3,4,5-tetramethylcyclopentadienyl]titanium trichloride, [1-tris{2,3-dimethyl-4,6-bis(dimethylamino)-phenyl)silyl-2,3,4,5-tetramethylcyclopentadienyl]titanium trichloride, [1-tris{2,3-dimethyl-5,6-bis(dimethylamino)-phenyl)silyl-2,3,4,5-tetramethylcyclopentadienyl]titanium trichloride, [1-tris{2,3-dimethyl-4,5,6-tris(dimethylamino)-phenyl)silyl-2,3,4,5-tetramethylcyclopentadienyl]titanium trichloride,

[1-tris(2,4-dimethyl-3-dimethylamino-phenyl)silyl-2,3,4,5-tetramethylcyclopentadienyl]titanium trichloride, [1-tris(2,4-dimethyl-5-dimethylamino-phenyl)silyl-2,3,4,5-tetramethylcyclopentadienyl]titanium trichloride, [1-tris(2,4-dimethyl-6-dimethylamino-phenyl)silyl-2,3,4,5-tetramethylcyclopentadienyl]titanium trichloride, [1-tris{2,4-dimethyl-3,5-bis(dimethylamino)-phenyl}silyl-2,3,4,5-tetramethylcyclopentadienyl]titanium trichloride, [1-tris{2,4-dimethyl-3,6-bis(dimethylamino)-phenyl}silyl-2,3,4,5-tetramethylcyclopentadienyl]titanium trichloride, [1-tris{2,4-dimethyl-5,6-bis(dimethylamino)-phenyl}silyl-2,3,4,5-tetramethylcyclopentadienyl]titanium trichloride, [1-tris{2,4-dimethyl-3,5,6-tris(dimethylamino)-phenyl}silyl-2,3,4,5-tetramethylcyclopentadienyl]titanium trichloride,

[1-tris(2,5-dimethyl-3-dimethylamino-phenyl)silyl-2,3,4,5-tetramethylcyclopentadienyl]titanium trichloride, [1-tris(2,5-dimethyl-4-dimethylamino-phenyl)silyl-2,3,4,5-tetramethylcyclopentadienyl]titanium trichloride, [1-tris(2,5-dimethyl-6-dimethylamino-phenyl)silyl-2,3,4,5-tetramethylcyclopentadienyl]titanium trichloride, [1-tris{2,5-dimethyl-3,4-bis(dimethylamino)-phenyl}silyl-2,3,4,5-tetramethylcyclopentadienyl]titanium trichloride, [1-tris{2,5-dimethyl-3,6-bis(dimethylamino)-phenyl}silyl-2,3,4,5-tetramethylcyclopentadienyl]titanium trichloride, [1-tris{2,5-dimethyl-4,6-bis(dimethylamino)-phenyl}silyl-2,3,4,5-tetramethylcyclopentadienyl]titanium trichloride, [1-tris{2,5-dimethyl-3,4,6-tris(dimethylamino)-phenyl}silyl-2,3,4,5-tetramethylcyclopentadienyl]titanium trichloride,

[1-tris(2,6-dimethyl-3-dimethylamino-phenyl)silyl-2,3,4,5-tetramethylcyclopentadienyl]titanium trichloride, [1-tris(2,6-dimethyl-4-dimethylamino-phenyl)silyl-2,3,4,5-tetramethylcyclopentadienyl]titanium trichloride, [1-tris{2,6-dimethyl-3,4-bis(dimethylamino)-phenyl}silyl-2,3,4,5-tetramethylcyclopentadienyl]titanium trichloride, [1-tris{2,6-dimethyl-3,5-bis(dimethylamino)-phenyl}silyl-2,3,4,5-tetramethylcyclopentadienyl]titanium trichloride, [1-tris{2,6-dimethyl-3,4,5-tris(dimethylamino)-phenyl}silyl-2,3,4,5-tetramethylcyclopentadienyl]titanium trichloride,

[1-tris(3,4-dimethyl-2-dimethylamino-phenyl)silyl-2,3,4,5-tetramethylcyclopentadienyl]titanium trichloride, [1-tris(3,4-dimethyl-5-dimethylamino-phenyl)silyl-2,3,4,5-tetramethylcyclopentadienyl]titanium trichloride, [1-tris(3,4-dimethyl-6-dimethylamino-phenyl)silyl-2,3,4,5-tetramethylcyclopentadienyl]titanium trichloride, [1-tris{3,4-dimethyl-2,5-bis(dimethylamino)-phenyl}silyl-2,3,4,5-tetramethylcyclopentadienyl]titanium trichloride, [1-tris{3,4-dimethyl-2,6-bis(dimethylamino)-phenyl}silyl-2,3,4,5-tetramethylcyclopentadienyl]titanium trichloride, [1-tris{3,4-dimethyl-5,6-bis(dimethylamino)-phenyl}silyl-2,3,4,5-tetramethylcyclopentadienyl]titanium trichloride, [1-tris{3,4-dimethyl-2,5,6-tris(dimethylamino)-phenyl}silyl-2,3,4,5-
tetramethylcyclopentadienyl]titanium trichloride,
[1-tris(3,5-dimethyl-2-dimethylamino-phenyl)silyl-2,3,4,5-
tetramethylcyclopentadienyl]titanium trichloride, [1-tris
(3,5-dimethyl-4-dimethylamino-phenyl)silyl-2,3,4,5-tetramethylcyclopentadienyl]titanium trichloride, [1-tris{3,
5-dimethyl-2,4-bis(dimethylamino)-phenyl}silyl-2,3,4,5-
tetramethylcyclopentadienyl]titanium trichloride and
[1-tris{3,5-dimethyl-2,4,6-tris(dimethylamino)-
phenyl}silyl-2,3,4,5-tetramethylcyclopentadienyl]titanium trichloride.

Moreover, examples of the transition metal complex (1) also include titanium chloride complexes obtained by substituting "cyclopentadienyl", "2-methylcyclopentadienyl", "3-methylcyclopentadienyl", "2,3-dimethylcyclopentadienyl", "2,4-dimethylcyclopentadienyl", "2,5-dimethylcyclopentadienyl", "2,3,5-trimethylcyclopentadienyl", "2-ethylcyclopentadienyl", "3-ethylcyclopentadienyl", "2-n-propylcyclopentadienyl", "3-n-propylcyclopentadienyl", "2-isopropylcyclopentadienyl", "3-isopropylcyclopentadienyl", "2-n-butylcyclopentadienyl", "3-n-butylcyclopentadienyl", "2-sec-butylcyclopentadienyl", "3-sec-butylcyclopentadienyl", "2-tert-butylcyclopentadienyl", "3-tert-butylcyclopentadienyl", "2-phenylcyclopentadienyl", "3-phenylcyclopentadienyl", "2-benzylcyclopentadienyl", "3-benzylcyclopentadienyl", "indenyl", "2-methylindenyl", "fluorenyl", "tetrahydroindenyl", "2-methyltetrahydroindenyl" or "octahydrofluorenyl" for "2,3,4,5-tetramethylcyclopentadienyl" in the titanium chloride complexes exemplified above.

Moreover, examples of the transition metal complex (1) also include: transition metal chloride complexes such as zirconium chloride complexes obtained by substituting "zirconium" for "titanium" in the complexes exemplified above, and hafnium chloride complexes obtained by substituting "hafnium" therefor; titanium halide complexes such as titanium fluoride complexes obtained by substituting "fluoride" for "chloride" in the complexes, titanium bromide complexes obtained by substituting "bromide" therefor and titanium iodide complexes obtained by substituting "iodide" therefor; titanium hydride complexes obtained by substituting "hydride" therefor; alkylated titanium complexes such as a methylated titanium complex obtained by substituting "methyl" therefor; arylated titanium complexes such as a phenylated titanium complex obtained by substituting "phenyl" therefor; aralkylated titanium complexes such as a benzylated titanium complex obtained by substituting "benzyl" therefor; titanium alkoxide complexes such as a titanium methoxide complex obtained by substituting "methoxide" therefor, a titanium n-butoxide complex obtained by substituting "n-butoxide" therefor and a titanium isopropoxide complex obtained by substituting "isopropoxide" therefor; titanium aryloxide complexes such as a titanium phenoxide complex obtained by substituting "phenoxide" therefor; titanium aralkyloxide complexes such as a titanium benzyloxide complex obtained by substituting "benzyloxide" therefor; and titanium amide complexes such as a titanium dimethylamide complex obtained by substituting "dimethylamide" therefor and a titanium diethylamide complex obtained by substituting "diethylamide" therefor.

Examples of the transition metal complex represented by formula (1) preferably include [1-tris(2-trimethylsilylphenyl)silyl-2,3,4,5-tetramethylcyclopentadienyl]titanium trichloride, [1-tris(3-trimethylsilylphenyl)silyl-2,3,4,5-tetramethylcyclopentadienyl]titanium trichloride, [1-tris(4-trimethylsilylphenyl)silyl-2,3,4,5-tetramethylcyclopentadienyl]titanium trichloride, [1-tris(5-methyl-3-trimethylsilylphenyl)silyl-2,3,4,5-tetramethylcyclopentadienyl]titanium trichloride, [1-tris(3,5-dimethyl-4-trimethylsilylphenyl)silyl-2,3,4,5-tetramethylcyclopentadienyl]titanium trichloride, [1-tris{3,5-bis(trimethylsilyl)phenyl}silyl-2,3,4,5-tetramethylcyclopentadienyl]titanium trichloride, [1-tris(3-methoxyphenyl)silyl-2,3,4,5-tetramethylcyclopentadienyl]titanium trichloride, [1-tris(4-methoxyphenyl)silyl-2,3,4,5-tetramethylcyclopentadienyl]titanium trichloride, [1-tris(5-methyl-3-methoxyphenyl)silyl-2,3,4,5-tetramethylcyclopentadienyl]titanium trichloride, [1-tris(3,5-dimethyl-4-methoxyphenyl)silyl-2,3,4,5-tetramethylcyclopentadienyl]titanium trichloride, [1-tris{3,5-dimethoxyphenyl}silyl-2,3,4,5-tetramethylcyclopentadienyl]titanium trichloride, and [1-tris(3-dimethylaminophenyl)silyl-2,3,4,5-tetramethylcyclopentadienyl]titanium trichloride.

<Method for Producing a Transition Metal Complex (1)>

The transition metal complex (1) can be produced by, for example, a production method comprising the steps of:
reacting a substituted cyclopentadiene compound (hereinafter, referred to as a "substituted cyclopentadiene compound (2)") represented by formula (2):

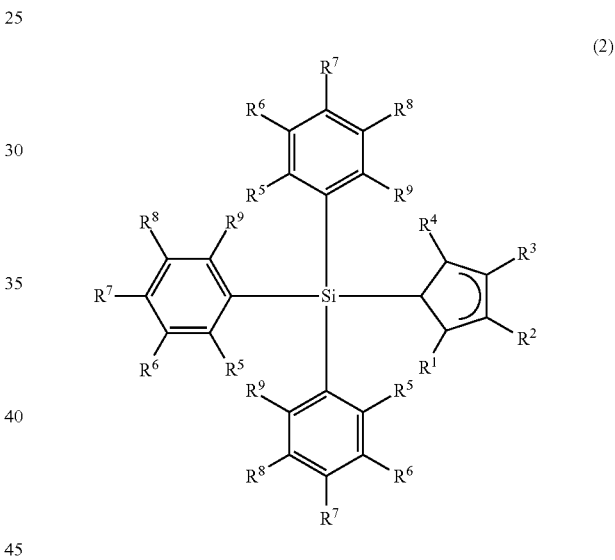

wherein $R^1$, $R^2$, $R^3$, $R^4$, $R^5$, $R^6$, $R^7$, $R^8$ and $R^9$ are as defined above,
with a base in the presence of an amine compound; and
reacting the reaction product of the substituted cyclopentadiene compound (2) and the base with a transition metal compound represented by formula (3) (hereinafter, referred to as a "transition metal compound (3)"):

wherein M, $X^1$, $X^2$ and $X^3$ are as defined above; and $X^4$ represents a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent, an aryloxy group having 6 to 20 carbon atoms which may have a halogen atom as a substituent, an aralkyl group having 7 to 20 carbon atoms which may have a halogen atom as a substituent, an aralkyloxy group having 7 to 20 carbon atoms which may have a halogen atom as a substituent, a substituted silyl group represented by —Si($R^{10}$)$_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20, or a disubstituted amino group represented by —N($R^{11}$)$_2$, wherein the two $R^{11}$ moieties each independently represent a hydrocarbyl group or a halogenated hydrocarbyl group, and the total number of the carbon atoms in the two $R^{11}$ moieties is 2 to 20, and m represents 0 or 1. Hereinafter, the step of reacting the substituted cyclopentadiene compound (2) with a base in the presence of an amine compound may be referred to as a "1st reaction step", and the step of reacting the reaction product of the substituted cyclopentadiene compound (2) and the base with a transition metal compound (3) may be referred to as a "2nd reaction step".

Isomers of the substituted cyclopentadiene compound (2) differing in the double bond position of the cyclopentadiene ring include the following structural isomers:

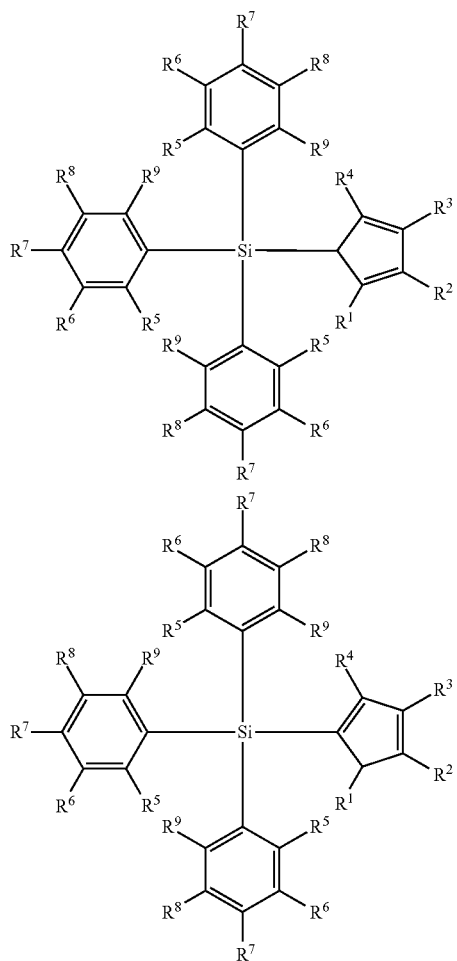

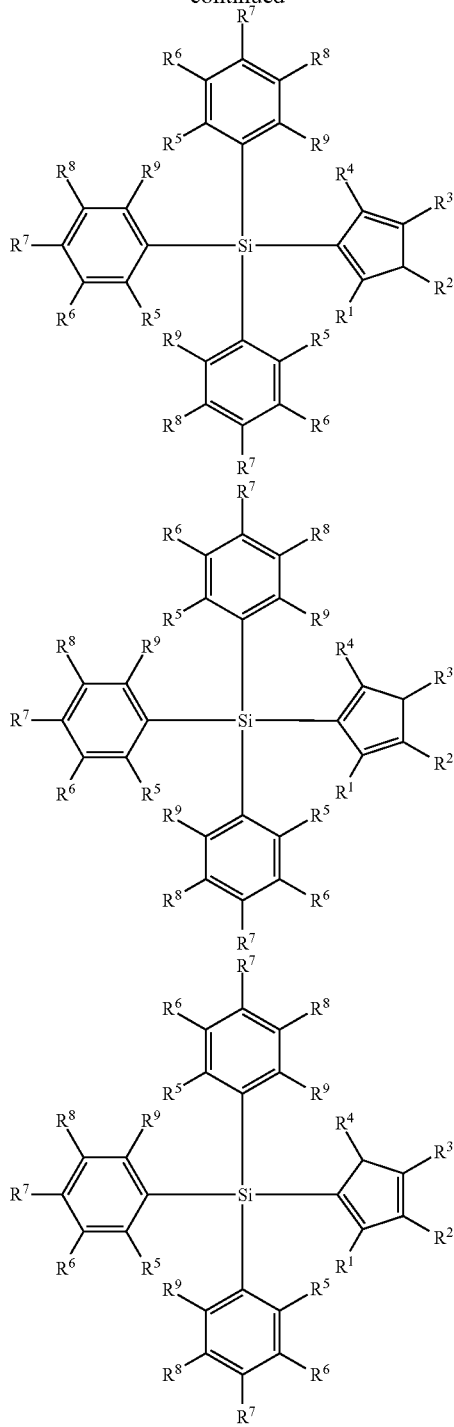

The substituted cyclopentadiene compound (2) has isomers differing in the double bond position of each cyclopentadiene ring. In the present invention, it represents any of them or a mixture of them.

In the transition metal compound (3), the substituent $X^4$ is as defined above, and specific examples thereof can include the same as those exemplified for $X^1$, $X^2$ and $X^3$.

Examples of the transition metal compound (3) include: titanium halide such as titanium tetrachloride, titanium trichloride, titanium tetrabromide and titanium tetraiodide; amidotitanium such as tetrakis(dimethylamino)titanium, dichlorobis(dimethylamino)titanium, trichloro(dimethylamino)titanium and tetrakis(diethylamino)titanium; and alkoxytitanium such as tetraisopropoxytitanium, tetra-n-butoxytitanium, dichlorodiisopropoxytitanium and trichloroisopropoxytitanium. Moreover, examples of the transition metal compound (3) include compounds obtained by substituting "zirconium" or "hafnium" for "titanium" in these compounds. Of them, a preferable transition metal compound (3) is titanium tetrachloride.

Examples of the base reacted with the substituted cyclopentadiene compound (2) in the 1st reaction step include organic alkali metal compounds typified by organic lithium compounds such as methyllithium, ethyllithium, n-butyllithium, sec-butyllithium, tert-butyllithium, lithiumtrimethylsilyl acetylide, lithium acetylide, trimethylsilylmethyllithium, vinyllithium, phenyllithium and allyllithium.

The amount of the base used may be in the range of 0.5 to 5 moles per mole of the substituted cyclopentadiene compound (2).

In the reaction of the substituted cyclopentadiene compound (2) with the base in the 1st reaction step, an amine compound is used. Examples of such an amine compound include: primary amine compounds such as methylamine, ethylamine, n-propylamine, isopropylamine, n-butylamine, tert-butylamine, n-octylamine, n-decylamine, aniline and ethylenediamine; secondary amine compounds such as dimethylamine, diethylamine, di-n-propylamine, diisopropylamine, di-n-butylamine, di-tert-butylamine, di-n-octylamine, di-n-decylamine, pyrrolidine, hexamethyldisilazane and diphenylamine; and tertiary amine compounds such as trimethylamine, triethylamine, tri-n-propylamine, tri-n-butylamine, diisopropylethylamine, tri-n-octylamine, tri-n-decylamine, triphenylamine, N,N-dimethylaniline, N,N,N',N'-tetramethylethylenediamine, N-methylpyrrolidine and 4-dimethylaminopyridine. The amount of such an amine compound used is preferably 10 moles or smaller, more preferably in the range of 0.5 to 10 moles, even more preferably in the range of 1 to 5 moles, per mole of the base.

In the 1st reaction step, the reaction of the substituted cyclopentadiene compound (2) with the base is preferably performed in the presence of a solvent. Moreover, when the solvent is used, the substituted cyclopentadiene compound (2) and the base are reacted in the solvent and then a transition metal compound (3) can be added into this reaction mixture to thereby further react the transition metal compound (3) with the reaction product of the substituted cyclopentadiene compound (2) and the base. Solids may be deposited in the reaction mixture obtained by reacting the substituted cyclopentadiene compound (2) and the base. In this case, the solvent may be further added until the deposited solid is dissolved; or the deposited solid may be temporarily separated by filtration or the like, and the solvent may be added to the separated solid for dissolution or suspension, followed by the addition of a transition metal compound (3). Moreover, when the solvent is used, the substituted cyclopentadiene compound (2), the base, the amine compound and the transition metal compound (3) can also be added simultaneously to the solvent to thereby perform the 1st reaction step and the 2nd reaction step almost simultaneously.

The solvent used in the 1st reaction step or in the 1st and 2nd reaction steps is an inert solvent that does not significantly hinder the progress of the reaction associated with these steps. Examples of such a solvent include aprotic solvents such as: aromatic hydrocarbyl solvents such as benzene and toluene; aliphatic hydrocarbyl solvents such as hexane and heptane; ether solvents such as diethyl ether, tetrahydrofuran and 1,4-dioxane; amide solvents such as hexamethylphosphoric amide and dimethylformamide; polar solvents such as acetonitrile, propionitrile, acetone, diethyl ketone, methyl isobutyl ketone and cyclohexanone; and halogen solvents such as dichloromethane, dichloroethane, chlorobenzene and dichlorobenzene. These solvents can be used alone or as a mixture of two or more thereof, and the amount thereof used is preferably 1 to 200 parts by weight, more preferably 3 to 50 parts by weight, per part by weight of the substituted cyclopentadiene compound (2).

The amount of the transition metal compound (3) used is preferably in the range of 0.5 to 3 moles, more preferably in the range of 0.7 to 1.5 moles, per mole of the substituted cyclopentadiene compound (2).

The reaction temperature of the 1st and 2nd reaction steps needs only to be a temperature between −100° C. and the boiling point of the solvent inclusive and is preferably in the range of from −80 to +100° C.

From the reaction mixture thus obtained through the 1st and 2nd reaction steps, the produced transition metal complex (1) can be taken by various purification methods known in the art. For example, the transition metal complex (1) of interest can be obtained by a method in which after the 1st and 2nd reaction steps, the formed precipitates are filtered off, and the filtrate is then concentrated to deposit a transition metal complex (1), which is then collected by filtration.

The compound having the transition metal complex (1) wherein any of $X^1$, $X^2$ and $X^3$ is an alkyl group having 1 to 20 carbon atoms which may have a halogen atom as a substituent, an alkoxy group having 1 to 20 carbon atoms which may have a halogen atom as a substituent, an aryl group having 6 to 20 carbon atoms which may have a halogen atom as a substituent, an aryloxy group having 6 to 20 carbon atoms which may have a halogen atom as a substituent, an aralkyl group having 7 to 20 carbon atoms which may have a halogen atom as a substituent, or an aralkyloxy group having 7 to 20 carbon atoms which may have a halogen atom as a substituent can also be obtained by the reaction of the compound having the transition metal complexes (1) wherein. $X^1$, $X^2$ and $X^3$ are a halogen atom with a lithium compound, a sodium compound, a potassium compound or a magnesium compound having the corresponding alkyl group, alkoxy group, aryl group, aryloxy group, aralkyl group and aralkyloxy group.

<Substituted Cyclopentadiene Compound (2)>

In the substituted cyclopentadiene compound (2), the substituents $R^1$, $R^2$, $R^3$, $R^4$, $R^5$, $R^6$, $R^7$, $R^8$ and $R^9$ are as defined above.

Examples of the substituted cyclopentadiene compound (2) include the following compounds.

1-tris(2-trimethylsilylphenyl)silyl-2,3,4,5-tetramethylcyclopentadiene, 1-tris(3-trimethylsilylphenyl)silyl-2,3,4,5-tetramethylcyclopentadiene, 1-tris(4-trimethylsilylphenyl)silyl-2,3,4,5-tetramethylcyclopentadiene, 1-tris{2,3-bis(trimethylsilyl)phenyl}silyl-2,3,4,5-tetramethylcyclopentadiene, 1-tris{2,4-bis(trimethylsilyl)phenyl}silyl-2,3,4,5-tetramethylcyclopentadiene, 1-tris{2,5-bis(trimethylsilyl)phenyl}silyl-2,3,4,5-tetramethylcyclopentadiene, 1-tris{2,6-bis(trimethylsilyl)phenyl}silyl-2,3,4,5-tetramethylcyclopentadiene, 1-tris{3,5-bis(trimethylsilyl)phenyl}silyl-2,3,4,5-tetramethylcyclopentadiene, 1-tris{2,3,4-tris(trimethylsilyl)phenyl}silyl-2,3,4,5-tetramethylcyclopentadiene, 1-tris{2,3,5-tris(trimethylsilyl)phenyl}silyl-2,3,4,5-tetramethylcyclopentadiene, 1-tris{2,3,6-tris(trimethylsilyl)phenyl}silyl-2,3,4,5-tetramethylcyclopentadiene, 1-tris{2,4,5-tris(trimethylsilyl)phenyl}silyl-2,3,4,5-tetramethylcyclopentadiene, 1-tris{2,4,6-tris(trimethylsilyl)phenyl}silyl-2,3,4,5-tetramethylcyclopentadiene, 1-tris{3,4,5-tris(trimethylsilyl)phenyl}silyl-2,3,4,5-tetramethylcyclopentadiene, 1-tris{2,3,4,5-tetrakis(trimethylsilyl)phenyl}silyl-2,3,4,5-tetramethylcyclopentadiene, 1-tris{2,3,4,6-tetrakis(trimethylsilyl)phenyl}silyl-2,3,4,5-tetramethylcyclopentadiene, 1-tris{2,3,4,5,6-pentakis(trimethylsilyl)phenyl}silyl-2,3,4,5-tetramethylcyclopentadiene, 1-tris(2-methyl-3-trimethylsilyl-phenyl)silyl-2,3,4,5-tetramethylcyclopentadiene, 1-tris(2-methyl-4-trimethylsilyl-phenyl)silyl-2,3,4,5-tetramethylcyclopentadiene, 1-tris(2-methyl-5-trimethylsilyl-phenyl)silyl-2,3,4,5-tetramethylcyclopentadiene, 1-tris(2-methyl-6-trimethylsilyl-phenyl)silyl-2,3,4,5-tetramethylcyclopentadiene, 1-tris{2-methyl-3,4-bis(trimethylsilyl)-phenyl}silyl-2,3,4,5-tetramethylcyclopentadiene, 1-tris{2-methyl-3,5-bis(trimethylsilyl)-phenyl}silyl-2,3,4,5-tetramethylcyclopentadiene, 1-tris{2-methyl-3,6-bis(trimethylsilyl)-phenyl}silyl-2,3,4,5-tetramethylcyclopentadiene, 1-tris{2-methyl-4,5-bis(trimethylsilyl)-phenyl}silyl-2,3,4,5-tetramethylcyclopentadiene, 1-tris{2-methyl-4,6-bis(trimethylsilyl)-phenyl}silyl-2,3,4,5-tetramethylcyclopentadiene, 1-tris{2-methyl-5,6-bis(trimethylsilyl)-phenyl}silyl-2,3,4,5-tetramethylcyclopentadiene, 1-tris{2-methyl-3,4,5-tris(trimethylsilyl)-phenyl}silyl-2,3,4,5-tetramethylcyclopentadiene, 1-tris{2-methyl-3,4,6-tris(trimethylsilyl)-phenyl}silyl-2,3,4,5-tetramethylcyclopentadiene, 1-tris{2-methyl-4,5,6-tris(trimethylsilyl)-phenyl}silyl-2,3,4,5-tetramethylcyclopentadiene, 1-tris{2-methyl-3,4,5,6-tetrakis(trimethylsilyl)-phenyl}silyl-2,3,4,5-tetramethylcyclopentadiene, 1-tris(3-methyl-2-trimethylsilyl-phenyl)silyl-2,3,4,5-tetramethylcyclopentadiene, 1-tris(3-methyl-4-trimethylsilyl-phenyl)silyl-2,3,4,5-tetramethylcyclopentadiene, 1-tris(3-methyl-5-trimethylsilyl-phenyl)silyl-2,3,4,5-tetramethylcyclopentadiene, 1-tris(3-methyl-6-trimethylsilyl-phenyl)silyl-2,3,4,5-tetramethylcyclopentadiene, 1-tris{3-methyl-2,4-bis(trimethylsilyl)-phenyl}silyl-2,3,4,5-tetramethylcyclopentadiene, 1-tris{3-methyl-2,5-bis(trimethylsilyl)-phenyl}silyl-2,3,4,5-tetramethylcyclopentadiene, 1-tris{3-methyl-2,6-bis(trimethylsilyl)-phenyl}silyl-2,3,4,5-tetramethylcyclopentadiene, 1-tris{3-methyl-4,5-bis(trimethylsilyl)-phenyl}silyl-2,3,4,5-tetramethylcyclopentadiene, 1-tris{3-methyl-4,6-bis(trimethylsilyl)-phenyl}silyl-2,3,4,5-tetramethylcyclopentadiene, 1-tris{3-methyl-5,6-bis(trimethylsilyl)-phenyl}silyl-2,3,4,5-tetramethylcyclopentadiene, 1-tris{3-methyl-2,4,5-tris(trimethylsilyl)-phenyl}silyl-2,3,4,5-tetramethylcyclopentadiene, 1-tris{3-methyl-2,4,6-tris(trimethylsilyl)-phenyl}silyl-2,3,4,5-tetramethylcyclopentadiene, 1-tris{3-methyl-4,5,6-tris(trimethylsilyl)-phenyl}silyl-2,3,4,5-tetramethylcyclopentadiene, 1-tris{3-methyl-2,4,5,6-tetrakis(trimethylsilyl)-phenyl}silyl-2,3,4,5-tetramethylcyclopentadiene, 1-tris(4-methyl-2-trimethylsilyl-phenyl)silyl-2,3,4,5-tetramethylcyclopentadiene, 1-tris(4-methyl-3-trimethylsilyl-phenyl)silyl-2,3,4,5-tetramethylcyclopentadiene, 1-tris{4-methyl-2,3-bis(trimethylsilyl)-phenyl}silyl-2,3,4,5-tetramethylcyclopentadiene, 1-tris{4-methyl-2,5-bis(trimethylsilyl)-phenyl}silyl-2,3,4,5-tetramethylcyclopentadiene, 1-tris bis(trimethylsilyl)-phenyl)silyl-2,3,4,5-tetramethylcyclopentadiene, 1-tris{4-methyl-3,5-bis(trimethylsilyl)-phenyl}silyl-2,3,4,5-tetramethylcyclopentadiene, 1-tris{4-methyl-2,3,5-tris(trimethylsilyl)-phenyl}silyl-2,3,4,5-tetramethylcyclopentadiene, 1-tris{4-methyl-2,3,6-tris(trimethylsilyl)-phenyl}silyl-2,3,4,5-tetramethylcyclopentadiene, 1-tris{4-methyl-2,3,5,6-tetrakis(trimethylsilyl)-phenyl}silyl-2,3,4,5-tetramethylcyclopentadiene, 1-tris(2,3-dimethyl-4-trimethylsilyl-phenyl)silyl-2,3,4,5-tetramethylcyclopentadiene, 1-tris(2,3-dimethyl-5-trimethylsilyl-phenyl)silyl-2,3,4,5-tetramethylcyclopentadiene, 1-tris(2,3-dimethyl-5-trimethylsilyl-phenyl)silyl-2,3,4,5-tetramethylcyclopentadiene, 1-tris{2,3-dimethyl-4,5-bis(trimethylsilyl)-phenyl)silyl-2,3,4,5-tetramethylcyclopentadiene, 1-tris{2,3-dimethyl-4,6-bis(trimethylsilyl)-phenyl)silyl-2,3,4,5-tetramethylcyclopentadiene, 1-tris{2,3-dimethyl-5,6-bis(trimethylsilyl)-phenyl)silyl-2,3,4,5-tetramethylcyclopentadiene, 1-tris{2,3-dimethyl-4,5,6-tris(trimethylsilyl)-phenyl)silyl-2,3,4,5-tetramethylcyclopentadiene, 1-tris(2,4-dimethyl-3-trimethyl silyl-phenyl)silyl-2,3,4,5-tetramethylcyclopentadiene, 1-tris(2,4-dimethyl-5-trimethylsilyl-phenyl)silyl-2,3,4,5-tetramethylcyclopentadiene, 1-tris(2,4-dimethyl-6-trimethylsilyl-phenyl)silyl-2,3,4,5-tetramethylcyclopentadiene, 1-tris{2,4-dimethyl-3,5-bis(trimethylsilyl)-phenyl}silyl-2,3,4,5-tetramethylcyclopentadiene, 1-tris{2,4-dimethyl-3,6-bis(trimethylsilyl)-phenyl}silyl-2,3,4,5-tetramethylcyclopentadiene, 1-tris{2,4-dimethyl-5,6-bis(trimethylsilyl)-phenyl}silyl-2,3,4,5-tetramethylcyclopentadiene, 1-tris{2,4-dimethyl-3,5,6-tris(trimethylsilyl)-phenyl}silyl-2,3,4,5-tetramethylcyclopentadiene, 1-tris(2,5-dimethyl-3-trimethylsilyl-phenyl)silyl-2,3,4,5-tetramethylcyclopentadiene, 1-tris(2,5-dimethyl-4-trimethylsilyl-phenyl)silyl-2,3,4,5-tetramethylcyclopentadiene, 1-tris(2,5-dimethyl-6-trimethylsilyl-phenyl)silyl-2,3,4,5-tetramethylcyclopentadiene, 1-tris{2,5-dimethyl-3,4-bis(trimethylsilyl)-phenyl}silyl-2,3,4,5-tetramethylcyclopentadiene, 1-tris{2,5-dimethyl-3,6-bis(trimethylsilyl)-phenyl}silyl-2,3,4,5-tetramethylcyclopentadiene, 1-tris{2,5-dimethyl-4,6-bis(trimethylsilyl)-phenyl}silyl-2,3,4,5-tetramethylcyclopentadiene, 1-tris{2,5-dimethyl-3,4,6-tris(trimethylsilyl)-phenyl}silyl-2,3,4,5-tetramethylcyclopentadiene, 1-tris(2,6-dimethyl-3-trimethylsilyl-phenyl)silyl-2,3,4,5-tetramethylcyclopentadiene, 1-tris(2,6-dimethyl-4-trimethylsilyl-phenyl)silyl-2,3,4,5-tetramethylcyclopentadiene, 1-tris{2,6-dimethyl-3,4-bis(trimethylsilyl)-phenyl}silyl-2,3,4,5-tetramethylcyclopentadiene, 1-tris{2,6-dimethyl-3,5-bis(trimethylsilyl)-phenyl}silyl-2,3,4,5-tetramethylcyclopentadiene, 1-tris{2,6-dimethyl-3,4,5-tris(trimethylsilyl)-phenyl}silyl-2,3,4,5-tetramethylcyclopentadiene, 1-tris(3,4-dimethyl-2-trimethylsilyl-phenyl)silyl-2,3,4,5-tetramethylcyclopentadiene, 1-tris(3,4-dimethyl-5-trimethylsilyl-phenyl)silyl-2,3,4,5-tetramethylcyclopentadiene, 1-tris(3,4-dimethyl-6-trimethylsilyl-phenyl)silyl-2,3,4,5-tetramethylcyclopentadiene, 1-tris{3,4-dimethyl-2,5-bis(trimethylsilyl)-phenyl}silyl-2,3,4,5-tetramethylcyclopentadiene, 1-tris{3,4-dimethyl-2,6-bis(trimethylsilyl)-phenyl}silyl-2,3,4,5-tetramethylcyclopentadiene, 1-tris{3,4-dimethyl-5,6-bis(trimethylsilyl)-phenyl}silyl- 2,3,4,5-tetramethylcyclopentadiene, 1-tris{3,4-dimethyl-2,5,6-tris(trimethylsilyl)-phenyl}silyl-2,3,4,5-tetramethylcyclopentadiene, 1-tris(3,5-dimethyl-2-trimethylsilyl-phenyl)silyl-2,3,4,5-tetramethylcyclopentadiene, 1-tris(3,5-dimethyl-4-trimethylsilyl-phenyl)silyl-2,3,4,5-tetramethylcyclopentadiene, 1-tris{3,5-dimethyl-2,4-bis(trimethylsilyl)-phenyl}silyl-2,3,4,5-tetramethylcyclopentadiene, 1-tris{3,5-dimethyl-2,4,6-tris(trimethylsilyl)-phenyl}silyl-2,3,4,5-tetramethylcyclopentadiene, 1-tris(2-methoxyphenyl)silyl-2,3,4,5-tetramethylcyclopentadiene, 1-tris(3-methoxy-phenyl)silyl-2,3,4,5-tetramethylcyclopentadiene, 1-tris(4-methoxy-phenyl)silyl-2,3,4,5-tetramethylcyclopentadiene, 1-tris{2,3-dimethoxy-phenyl}silyl-2,3,4,5-tetramethylcyclopentadiene, 1-tris{2,4-dimethoxy-phenyl}silyl-2,3,4,5-tetramethylcyclopentadiene, 1-tris{2,5-dimethoxy-phenyl}silyl-2,3,4,5-tetramethylcyclopentadiene, 1-tris{2,6-dimethoxy-phenyl}silyl-2,3,4,5-tetramethylcyclopentadiene, 1-tris{3,5-dimethoxy-phenyl}silyl-2,3,4,5-tetramethylcyclopentadiene, 1-tris{2,3,4-trimethoxy-phenyl}silyl-2,3,4,5-tetramethylcyclopentadiene, 1-tris{2,3,5-trimethoxy-phenyl}silyl-2,3,4,5-tetramethylcyclopentadiene, 1-tris{2,3,6-trimethoxy-phenyl}silyl-2,3,4,5-tetramethylcyclopentadiene, 1-tris{2,4,5-trimethoxy-phenyl}silyl-2,3,4,5-tetramethylcyclopentadiene, 1-tris{2,4,6-trimethoxy-phenyl}silyl-2,3,4,5-tetramethylcyclopentadiene, 1-tris{3,4,5-trimethoxy-phenyl}silyl-2,3,4,5-tetramethylcyclopentadiene, 1-tris{2,3,4,5-tetramethoxy-phenyl}silyl-2,3,4,5-tetramethylcyclopentadiene, 1-tris{2,3,4,6-tetramethoxy-phenyl}silyl-2,3,4,5-tetramethylcyclopentadiene, 1-tris{2,3,4,5,6-pentamethoxy-phenyl}silyl-2,3,4,5-tetramethylcyclopentadiene, 1-tris(2-methyl-3-methoxy-phenyl)silyl-2,3,4,5-tetramethylcyclopentadiene, 1-tris(2-methyl-4-methoxy-phenyl)silyl-2,3,4,5-tetramethylcyclopentadiene, 1-tris(2-methyl-5-methoxy-phenyl)silyl-2,3,4,5-tetramethylcyclopentadiene, 1-tris(2-methyl-6-methoxy-phenyl)silyl-2,3,4,5-tetramethylcyclopentadiene, 1-tris{2-methyl-3,4-dimethoxy-phenyl}silyl-2,3,4,5-tetramethylcyclopentadiene, 1-tris{2-methyl-3,5-dimethoxy-phenyl}silyl-2,3,4,5-tetramethylcyclopentadiene, 1-tris{2-methyl-3,6-dimethoxy-phenyl}silyl-2,3,4,5-tetramethylcyclopentadiene, 1-tris{2-methyl-4,5-dimethoxy-phenyl}silyl-2,3,4,5-tetramethylcyclopentadiene, 1-tris{2-methyl-4,6-dimethoxy-phenyl}silyl-2,3,4,5-tetramethylcyclopentadiene, 1-tris{2-methyl-5,6-dimethoxy-phenyl}silyl-2,3,4,5-tetramethylcyclopentadiene, 1-tris{2-methyl-3,4,5-trimethoxy-phenyl}silyl-2,3,4,5-tetramethylcyclopentadiene, 1-tris{2-methyl-3,4,6-trimethoxy-phenyl}silyl-2,3,4,5-tetramethylcyclopentadiene, 1-tris{2-methyl-4,5,6-trimethoxy-phenyl}silyl-2,3,4,5-tetramethylcyclopentadiene, 1-tris{2-methyl-3,4,5,6-tetramethoxy-phenyl}silyl-2,3,4,5-tetramethylcyclopentadiene, 1-tris(3-methyl-2-methoxy-phenyl)silyl-2,3,4,5-tetramethylcyclopentadiene, 1-tris(3-methyl-4-methoxy-phenyl)silyl-2,3,4,5-tetramethylcyclopentadiene, 1-tris(3-methyl-5-methoxy-phenyl)silyl-2,3,4,5-tetramethylcyclopentadiene, 1-tris(3-methyl-6-methoxy-phenyl)silyl-2,3,4,5-tetramethylcyclopentadiene, 1-tris{3-methyl-2,4-dimethoxy-phenyl}silyl-2,3,4,5-tetramethylcyclopentadiene, 1-tris{3-methyl-2,5-dimethoxy-phenyl}silyl-2,3,4,5-tetramethylcyclopentadiene, 1-tris{3-methyl-2,6-dimethoxy-phenyl}silyl-2,3,4,5-tetramethylcyclopentadiene, 1-tris{3-methyl-4,5-dimethoxy-phenyl}silyl-2,3,4,5-tetramethylcyclopentadiene, 1-tris{3-methyl-4,6-dimethoxy-phenyl}silyl-2,3,4,5-tetramethylcyclopentadiene, 1-tris{3-methyl-5,6-dimethoxy-phenyl}silyl-2,3,4,5-tetramethylcyclopentadiene, 1-tris{3-methyl-2,4,5-trimethoxy-phenyl}silyl-2,3,4,5-tetramethylcyclopentadiene, 1-tris{3-methyl-2,4,6-trimethoxy-phenyl}silyl-2,3,4,5-tetramethylcyclopentadiene, 1-tris{3-methyl-4,5,6-trimethoxy-phenyl}silyl-2,3,4,5-tetramethylcyclopentadiene, 1-tris{3-methyl-2,4,5,6-tetramethoxy-phenyl}silyl-2,3,4,5-tetramethylcyclopentadiene, 1-tris(4-methyl-2-methoxy-phenyl)silyl-2,3,4,5-tetramethylcyclopentadiene, 1-tris(4-methyl-3-methoxy-phenyl)silyl-2,3,4,5-tetramethylcyclopentadiene, 1-tris{4-methyl-2,3-dimethoxy-phenyl}silyl-2,3,4,5-tetramethylcyclopentadiene, 1-tris{4-methyl-2,5-dimethoxy-phenyl}silyl-2,3,4,5-tetramethylcyclopentadiene, 1-tris{4-methyl-2,6-dimethoxy-phenyl}silyl-2,3,4,5-tetramethylcyclopentadiene, 1-tris{4-methyl-3,5-dimethoxy-phenyl}silyl-2,3,4,5-tetramethylcyclopentadiene, 1-tris{4-methyl-2,3,5-trimethoxy-phenyl}silyl-2,3,4,5-tetramethylcyclopentadiene, 1-tris{4-methyl-2,3,6-trimethoxy-phenyl}silyl-2,3,4,5-tetramethylcyclopentadiene, 1-tris{4-methyl-2,3,5,6-tetramethoxy-phenyl}silyl-2,3,4,5-tetramethylcyclopentadiene, 1-tris(2,3-dimethyl-4-methoxy-phenyl)silyl-2,3,4,5-tetramethylcyclopentadiene, 1-tris(2,3-dimethyl-5-methoxy-phenyl)silyl-2,3,4,5-tetramethylcyclopentadiene, 1-tris(2,3-dimethyl-5-methoxy-phenyl)silyl-2,3,4,5-tetramethylcyclopentadiene, 1-tris{2,3-dimethyl-4,5-dimethoxy-phenyl)silyl-2,3,4,5-tetramethylcyclopentadiene, 1-tris{2,3-dimethyl-4,6-dimethoxy-phenyl)silyl-2,3,4,5-tetramethylcyclopentadiene, 1-tris{2,3-dimethyl-5,6-dimethoxy-phenyl)silyl-2,3,4,5-tetramethylcyclopentadiene, 1-tris{2,3-dimethyl-4,5,6-trimethoxy-phenyl)silyl-2,3,4,5-tetramethylcyclopentadiene, 1-tris(2,4-dimethyl-3-methoxy-phenyl)silyl-2,3,4,5-tetramethyl cyclopentadiene, 1-tris(2,4-dimethyl-5-methoxy-phenyl)silyl-2,3,4,5-tetramethylcyclopentadiene, 1-tris(2,4-dimethyl-6-methoxy-phenyl)silyl-2,3,4,5-tetramethylcyclopentadiene, 1-tris{2,4-dimethyl-3,5-dimethoxy-phenyl}silyl-2,3,4,5-tetramethylcyclopentadiene, 1-tris{2,4-dimethyl-3,6-dimethoxy-phenyl}silyl-2,3,4,5-tetramethylcyclopentadiene, 1-tris{2,4-dimethyl-5,6-dimethoxy-phenyl}silyl-2,3,4,5-tetramethylcyclopentadiene, 1-tris{2,4-dimethyl-3,5,6-trimethoxy-phenyl}silyl-2,3,4,5-tetramethylcyclopentadiene, 1-tris(2,5-dimethyl-3-methoxy-phenyl)silyl-2,3,4,5-tetramethylcyclopentadiene, 1-tris(2,5-dimethyl-4-methoxy-phenyl)silyl-2,3,4,5-tetramethylcyclopentadiene, 1-tris(2,5-dimethyl-6-methoxy-phenyl)silyl-2,3,4,5-tetramethylcyclopentadiene, 1-tris{2,5-dimethyl-3,4-dimethoxy-phenyl}silyl-2,3,4,5-tetramethylcyclopentadiene, 1-tris{2,5-dimethyl-3,6- dimethoxy-phenyl}silyl-2,3,4,5-tetramethylcyclopentadiene, 1-tris{2,5-dimethyl-4,6-dimethoxy-phenyl}silyl-2,3,4,5-tetramethylcyclopentadiene, 1-tris{2,5-dimethyl-3,4,6-trimethoxy-phenyl}silyl-2,3,4,5-tetramethylcyclopentadiene, 1-tris(2,6-dimethyl-3-methoxy-phenyl)silyl-2,3,4,5-tetramethylcyclopentadiene, 1-tris(2,6-dimethyl-4-methoxy-phenyl)silyl-2,3,4,5-tetramethylcyclopentadiene, 1-tris{2,6-dimethyl-3,4-dimethoxy-phenyl}silyl-2,3,4,5-tetramethylcyclopentadiene, 1-tris{2,6-dimethyl-3,5-dimethoxy-1-phenyl}silyl-2,3,4,5-tetramethylcyclopentadiene, 1-tris{2,6-dimethyl-3,4,5-trimethoxy-phenyl}silyl-2,3,4,5-tetramethylcyclopentadiene, 1-tris(3,4-dimethyl-2-methoxy-phenyl)silyl-2,3,4,5-tetramethylcyclopentadiene, 1-tris(3,4-dimethyl-5-methoxy-phenyl)silyl-2,3,4,5-tetramethylcyclopentadiene, 1-tris(3,4-dimethyl-6-methoxy-phenyl)silyl-2,3,4,5-tetramethylcyclopentadiene, 1-tris{3,4-dimethyl-2,5-dimethoxy-phenyl}silyl-2,3,4,5-tetramethylcyclopentadiene, 1-tris{3,4-dimethyl-2,6-dimethoxy-phenyl}silyl-2,3,4,5-tetramethylcyclopentadiene, 1-tris{3,4-dimethyl-5,6-dimethoxy-phenyl}silyl-2,3,4,5-tetramethylcyclopentadiene, 1-tris{3,4-dimethyl-2,5,6-trimethoxy-phenyl}silyl-2,3,4,5-tetramethylcyclopentadiene, 1-tris(3,5-dimethyl-2-methoxy-phenyl)silyl-2,3,4,5-tetramethylcyclopentadiene, 1-tris(3,5-dimethyl-4-methoxy-phenyl)silyl-2,3,4,5-tetramethylcyclopentadiene, 1-tris{3,5-dimethyl-2,4-dimethoxy-phenyl}silyl-2,3,4,5-tetramethylcyclopentadiene, 1-tris{3,5-dimethyl-2,4,6-trimethoxy-phenyl}silyl-2,3,4,5-tetramethylcyclopentadiene, 1-tris(2-dimethylamino-phenyl)silyl-2,3,4,5-tetramethylcyclopentadiene, 1-tris(3-dimethylamino-phenyl)silyl-2,3,4,5-tetramethylcyclopentadiene, 1-tris(4-dimethylamino-phenyl)silyl-2,3,4,5-tetramethylcyclopentadiene, 1-tris{2,3-bis(dimethylamino)phenyl}silyl-2,3,4,5-tetramethylcyclopentadiene, 1-tris{2,4-bis(dimethylamino)phenyl}silyl-2,3,4,5-tetramethylcyclopentadiene, 1-tris{2,5-bis(dimethylamino)phenyl}silyl-2,3,4,5-tetramethylcyclopentadiene, 1-tris{2,6-bis(dimethylamino)phenyl}silyl-2,3,4,5-tetramethylcyclopentadiene, 1-tris{3,5-bis(dimethylamino)phenyl}silyl-2,3,4,5-tetramethylcyclopentadiene, 1-tris{2,3,4-tris(dimethylamino)phenyl}silyl-2,3,4,5-tetramethylcyclopentadiene, 1-tris{2,3,5-tris(dimethylamino)phenyl}silyl-2,3,4,5-tetramethylcyclopentadiene, 1-tris{2,3,6-tris(dimethylamino)phenyl}silyl-2,3,4,5-tetramethylcyclopentadiene, 1-tris{2,4,5-tris(dimethylamino)phenyl}silyl-2,3,4,5-tetramethylcyclopentadiene, 1-tris{2,4,6-tris(dimethylamino)phenyl}silyl-2,3,4,5-tetramethylcyclopentadiene, 1-tris{3,4,5-tris(dimethylamino)phenyl}silyl-2,3,4,5-tetramethylcyclopentadiene, 1-tris{2,3,4,5-tetrakis(dimethylamino)phenyl}silyl-2,3,4,5-tetramethylcyclopentadiene, 1-tris{2,3,4,6-tetrakis(dimethylamino)phenyl}silyl-2,3,4,5-tetramethylcyclopentadiene, 1-tris{2,3,4,5,6-pentakis(dimethylamino)phenyl}silyl-2,3,4,5-tetramethylcyclopentadiene, 1-tris(2-methyl-3-dimethylamino-phenyl)silyl-2,3,4,5-tetramethylcyclopentadiene, 1-tris(2-methyl-4-dimethylamino-phenyl)silyl-2,3,4,5-tetramethylcyclopentadiene, 1-tris(2-methyl-5-dimethylamino-phenyl)silyl-2,3,4,5-tetramethylcyclopentadiene, 1-tris(2-methyl-6-dimethylamino-phenyl)silyl-2,3,4,5-tetramethylcyclopentadiene, 1-tris{2-methyl-3,4-bis(dimethylamino)-phenyl}silyl-2,3,4,5-tetramethylcyclopentadiene, 1-tris{2-methyl-3,5-bis(dimethylamino)-phenyl}silyl-2,3,4,5-tetramethylcyclopentadiene, 1-tris{2-methyl-3,6-bis(dimethylamino)-phenyl}silyl-2,3,4,5-tetramethylcyclopentadiene, 1-tris{2-methyl-4,5-bis(dimethylamino)-phenyl}silyl-2,3,4,5-tetramethyl cyclopentadiene, 1-tris{2-methyl-4,6-bis(dimethylamino)-phenyl}silyl-2,3,4,5-tetramethylcyclopentadiene, 1-tris{2-methyl-5,6-bis(dimethylamino)-phenyl}silyl-2,3,4,5-tetramethylcyclopentadiene, 1-tris{2-methyl-3,4,5-tris(dimethylamino)-phenyl}silyl-2,3,4,5-tetramethylcyclopentadiene, 1-tris{2-methyl-3,4,6-tris(dimethylamino)-phenyl}silyl-2,3,4,5-tetramethylcyclopentadiene, 1-tris{2-methyl-4,5,6-tris(dimethylamino)-phenyl}silyl-2,3,4,5-tetramethylcyclopentadiene, 1-tris{2-methyl-3,4,5,6-tetrakis(dimethylamino)-phenyl}silyl-2,3,4,5-tetramethyl cyclopentadiene, 1-tris(3-methyl-2-dimethylamino-phenyl)silyl-2,3,4,5-tetramethylcyclopentadiene, 1-tris(3-methyl-4-dimethylamino-phenyl)silyl-2,3,4,5-tetramethylcyclopentadiene, 1-tris(3-methyl-5-dimethylamino-phenyl)silyl-2,3,4,5-tetramethylcyclopentadiene, 1-tris(3-methyl-6-dimethylamino-phenyl)silyl-2,3,4,5-tetramethylcyclopentadiene, 1-tris{3-methyl-2,4-bis(dimethylamino)-phenyl}silyl-2,3,4,5-tetramethylcyclopentadiene, 1-tris{3-methyl-2,5-bis(dimethylamino)-phenyl}silyl-2,3,4,5-tetramethylcyclopentadiene, 1-tris{3-methyl-2,6-bis(dimethylamino)-phenyl}silyl-2,3,4,5-tetramethylcyclopentadiene, 1-tris{3-methyl-4,5-bis(dimethylamino)-phenyl}silyl-2,3,4,5-tetramethylcyclopentadiene, 1-tris{3-methyl-4,6-bis(dimethylamino)-phenyl}silyl-2,3,4,5-tetramethylcyclopentadiene, 1-tris{3-methyl-5,6-bis(dimethylamino)-phenyl}silyl-2,3,4,5-tetramethylcyclopentadiene, 1-tris{3-methyl-2,4,5-tris(dimethylamino)-phenyl}silyl-2,3,4,5-tetramethylcyclopentadiene, 1-tris{3-methyl-2,4,6-tris(dimethylamino)-phenyl}silyl-2,3,4,5-tetramethylcyclopentadiene, 1-tris{3-methyl-4,5,6-tris(dimethylamino)-phenyl}silyl-2,3,4,5-tetramethylcyclopentadiene, 1-tris{3-methyl-2,4,5,6-tetrakis(dimethylamino)-phenyl}silyl-2,3,4,5-tetramethylcyclopentadiene, 1-tris(4-methyl-2-dimethylamino-phenyl)silyl-2,3,4,5-tetramethylcyclopentadiene, 1-tris(4-methyl-3-dim ethylamino-phenyl)silyl-2,3,4,5-tetramethylcyclopentadiene, 1-tris{4-methyl-2,3-bis(dimethylamino)-phenyl}silyl-2,3,4,5-tetramethylcyclopentadiene, 1-tris{4-methyl-2,5-bis(dimethylamino)-phenyl}silyl-2,3,4,5-tetramethylcyclopentadiene, 1-tris{4-methyl-2,6-bis(dimethylamino)-phenyl}silyl-2,3,4,5-tetramethylcyclopentadiene, 1-tris{4-methyl-3,5-bis(dimethylamino)-phenyl}silyl-2,3,4,5-tetramethylcyclopentadiene, 1-tris{4-methyl-2,3,5-tris(dimethylamino)-phenyl}silyl-2,3,4,5-tetramethylcyclopentadiene, 1-tris{4-methyl-2,3,6-tris(dimethylamino)-phenyl}silyl-2,3,4,5-tetramethylcyclopentadiene, 1-tris{4-methyl-2,3,5,6-tetrakis(dimethylamino)-phenyl}silyl-2,3,4,5-tetramethylcyclopentadiene, 1-tris(2,3-dimethyl-4-dimethylamino-phenyl)silyl-2,3,4,5-tetramethylcyclopentadiene, 1-tris(2,3-dimethyl-5-dimethylamino-phenyl)silyl-2,3,4,5-tetramethylcyclopentadiene, 1-tris(2,3-dimethyl-5-dimethylamino-phenyl)silyl-2,3,4,5-tetramethylcyclopentadiene, 1-tris{2,3-dimethyl-4,5-bis(dimethylamino)-phenyl)silyl-2,3,4,5-tetramethylcyclopentadiene, 1-tris{2,3-dimethyl-4,6-bis(dimethylamino)-phenyl)silyl-2,3,4,5-tetramethylcyclopentadiene, 1-tris{2,3-dimethyl-5,6-bis(dimethylamino)-phenyl)silyl-2,3,4,5-tetramethylcyclopentadiene, 1-tris{2,3-dimethyl-4,5,6-tris(dimethylamino)-phenyl)silyl-2,4-tetramethylcyclopentadiene, 1-tris(2,4-dimethyl-3-dimethylamino-phenyl)silyl-2,3,4,5-tetramethylcyclopentadiene, 1-tris(2,4-dimethyl-5-dimethylamino-phenyl)silyl-2,3,4,5-tetramethylcyclopentadiene, 1-tris(2,4-dimethyl-6-dimethylamino-phenyl)silyl-2,3,4,5-tetramethylcyclopentadiene, 1-tris{2,4-dimethyl-3,5-bis(dimethylamino)-phenyl}silyl-2,3,4,5-tetramethylcyclopentadiene, 1-tris{2,4-dimethyl-3,6-bis(dimethylamino)-phenyl}silyl-2,3,4,5-tetramethylcyclopentadiene, 1-tris{2,4-dimethyl-5,6-bis(dimethylamino)-phenyl}silyl-2,3,4,5-tetramethylcyclopentadiene, 1-tris{2,4-dimethyl-3,5,6-tris(dimethylamino)-phenyl}silyl-2,3,4,5-tetramethylcyclopentadiene, 1-tris(2,5-dimethyl-3-dimethylamino-phenyl)silyl-2,3,4,5-tetramethylcyclopentadiene, 1-tris(2,5-dimethyl-4-dimethylamino-phenyl)silyl-2,3,4,5-tetramethylcyclopentadiene, 1-tris(2,5-dimethyl-6-dimethylamino-phenyl)silyl-2,3,4,5-tetramethylcyclopentadiene, 1-tris{2,5-dimethyl-3,4-bis(dimethylamino)-phenyl}silyl-2,3,4,5-tetramethylcyclopentadiene, 1-tris{2,5-dimethyl-3,6-bis(dimethylamino)-phenyl}silyl-2,3,4,5-tetramethylcyclopentadiene, 1-tris{2,5-dimethyl-4,6-bis(dimethylamino)-phenyl}silyl-2,3,4,5-tetramethylcyclopentadiene, 1-tris{2,5-dimethyl-3,4,6-tris(dimethylamino)-phenyl}silyl-2,3,4,5-tetramethylcyclopentadiene, 1-tris(2,6-dimethyl-3-dimethylamino-phenyl)silyl-2,3,4,5-tetramethylcyclopentadiene, 1-tris(2,6-dimethyl-4-dimethylamino-phenyl)silyl-2,3,4,5-tetramethylcyclopentadiene, 1-tris{2,6-dimethyl-3,4-bis(dimethylamino)-phenyl}silyl-2,3,4,5-tetramethylcyclopentadiene, 1-tris{2,6-dimethyl-3,5-bis(dimethylamino)-phenyl}silyl-2,3,4,5-tetramethylcyclopentadiene, 1-tris{2,6-dimethyl-3,4,5-tris(dimethylamino)-phenyl}silyl-2,3,4,5-tetramethylcyclopentadiene, 1-tris(3,4-dimethyl-2-dimethylamino-phenyl)silyl-2,3,4,5-tetramethylcyclopentadiene, 1-tris(3,4-dimethyl-5-dimethylamino-phenyl)silyl-2,3,4,5-tetramethylcyclopentadiene, 1-tris(3,4-dimethyl-6-dimethylamino-phenyl)silyl-2,3,4,5-tetramethylcyclopentadiene, 1-tris{3,4-dimethyl-2,5-bis(dimethylamino)-phenyl}silyl-2,3,4,5-tetramethylcyclopentadiene, 1-tris{3,4-dimethyl-2,6-bis(dimethylamino)-phenyl}silyl-2,3,4,5-tetramethylcyclopentadiene, 1-tris{3,4-dimethyl-5,6-bis(dimethylamino)-phenyl}silyl-2,3,4,5-tetramethylcyclopentadiene, 1-tris{3,4-dimethyl-2,5,6-tris(dimethylamino)-phenyl}silyl-2,3,4,5-tetramethylcyclopentadiene, 1-tris(3,5-dimethyl-2-dimethylamino-phenyl)silyl-2,3,4,5-tetramethylcyclopentadiene, 1-tris(3,5-dimethyl-4-dimethylamino-phenyl)silyl-2,3,4,5-tetramethylcyclopentadiene, 1-tris{3,5-dimethyl-2,4-bis(dimethylamino)-phenyl}silyl-2,3,4,5-tetramethylcyclopentadiene and 1-tris{3,5-dimethyl-2,4,6-tris(dimethylamino)-phenyl}silyl-2,3,4,5-tetramethylcyclopentadiene.

Moreover, examples of the substituted cyclopentadiene compound also include: substituted cyclopentadiene compounds obtained by substituting "cyclopentadiene", "2-methylcyclopentadiene", "3-methylcyclopentadiene", "2,3-dimethylcyclopentadiene", "2,4-dimethylcyclopentadiene", "2,5-dimethylcyclopentadiene", "2,3,5-trimethyl cyclopentadiene", "2-ethylcyclopentadiene", "3-ethylcyclopentadiene", "2-n-propylcyclopentadiene", "3-n-propylcyclopentadiene", "2-isopropylcyclopentadiene", "3-isopropylcyclopentadiene", "2-n-butylcyclopentadiene", "3-n-butylcyclopentadiene", "2-sec-butylcyclopentadiene", "3-sec-butylcyclopentadiene", "2-tert-butylcyclopentadiene", "3-tert-butylcyclopentadiene", "2-phenylcyclopentadiene", "3-phenylcyclopentadiene", "2-benzylcyclopentadiene", "3-benzylcyclopentadiene", "indene", "2-methylindene", "fluorene", "tetrahydro indene", "2-methyl tetrahydro indene" or "octahydrofluorene" for "2,3,4,5-tetramethylcyclopentadiene" in the substituted cyclopentadiene compounds exemplified above.

The substituted cyclopentadiene compounds exemplified above may have isomers differing in the double bond position of the cyclopentadiene ring. A mixture of these isomers may also be used.

<Methods for Producing Substituted Cyclopentadiene Compound (2)>

The substituted cyclopentadiene compound represented by formula (2) can be produced by a method comprising the steps of:

reacting the substituted cyclopentadiene compound represented by formula (4) (hereinafter, abbreviated to a "substituted cyclopentadiene compound (4)") with a base; and reacting the reaction product of the substituted cyclopentadiene compound (4) and the base with a halogenated silyl compound represented by formula (5).

The substituted cyclopentadiene compound represented by formula (4) is as follows:

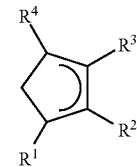

(4)

wherein $R^1$, $R^2$, $R^3$ and $R^4$ are as defined above, and the moiety

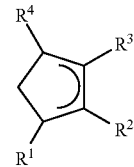

represents

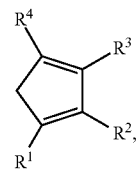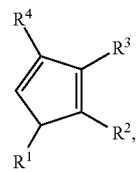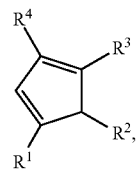

-continued

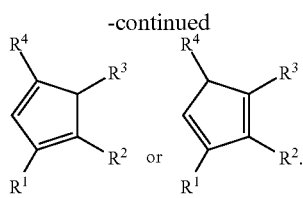

Examples of the substituted cyclopentadiene compound (4) include the following compounds:
cyclopentadiene, methylcyclopentadiene, 1,2-dimethylcyclopentadiene, 1,3-dimethylcyclopentadiene, 1,2,3-trimethyl cyclopentadiene, 1,3,4-trimethyl cyclopentadiene, 1,2,3,4-tetramethylcyclopentadiene, ethylcyclopentadiene, 1,2-diethylcyclopentadiene, 1,3-diethylcyclopentadiene, 1,2,3-triethylcyclopentadiene, 1,3,4-triethylcyclopentadiene, 1,2,3,4-tetrethylcyclopentadiene, n-propylcyclopentadiene, isopropylcyclopentadiene, n-butylcyclopentadiene, sec-butylcyclopentadiene, tert-butylcyclopentadiene, n-pentylcyclopentadiene, neopentyl cyclopentadiene, n-hexylcyclopentadiene, n-octylcyclopentadiene, phenylcyclopentadiene, naphthyl cyclopentadiene, trimethyl silylcyclopentadiene, triethylsilylcyclopentadiene, tort-butyldimethylsilylcyclopentadiene, indene, 2-methylindene, tetrahydroindene, 2-methyltetrahydroindene, 3-methyltetrahydroindene, 2,3-dimethyltetrahydroindene, 2-ethyltetrahydroindene, 2-n-propyltetrahydroindene, 2-isopropyltetrahydroindene, 2-n-butyltetrahydroindene, 2-sec-butyltetrahydroindene, 2-tert-butyltetrahydroindene, 2-n-pentyltetrahydroindene, 2-neopentyltetrahydroindene, 2-amyltetrahydroindene, 2-n-hexyltetrahydroindene, 2-cyclohexyltetrahydroindene, 2-n-octyltetrahydroindene, 2-n-decyltetrahydroindene, 2-phenyltetrahydroindene, 2-benzyltetrahydroindene, 2-naphthyltetrahydroindene, 2-methoxytetrahydroindene, 2-phenoxytetrahydroindene, 2-benzyloxytetrahydroindene, 2-dimethylaminotetrahydroindene, 2-trimethylsilyltetrahydroindene, fluorene and octahydrofluorene.

The substituted cyclopentadiene compounds (4) exemplified above may have isomers differing in the double bond position of each cyclopentadiene ring. A mixture of these isomers may be used.

The halogenated silyl compound represented by formula (5) (hereinafter, abbreviated to a "halogenated silyl compound (5)") is as follows:

(5)

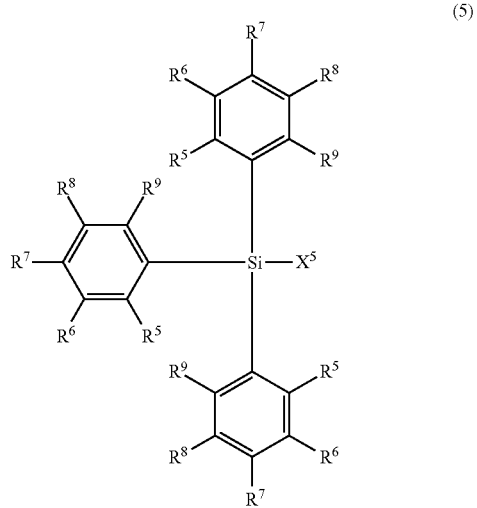

wherein $R^5$, $R^6$, $R^7$, $R^8$ and $R^9$ are as defined above, and $X^5$ is a halogen atom.

Examples of the halogenated silyl compound (5) include the following compounds:
chlorotris(2-trimethylsilylphenyl)silane, chlorotris(3-trimethylsilylphenyl)silane, chlorotris(4-trimethylsilylphenyl) silane, chlorotris{2,3-bis(trimethylsilyl)phenyl}silane, chlorotris{2,4-bis(trimethylsilyl)phenyl}silane, chlorotris{2,5-bis(trimethylsilyl)phenyl}silane, chlorotris{2,6-bis(trimethylsilyl)phenyl}silane, chlorotris{3,4-bis(trimethylsilyl)phenyl}silane, chlorotris {3,5-bis(trimethyl silyl)phenyl}silane, chlorotris{2,3,4-tris(trimethylsilyl) phenyl}silane, chlorotris{2,3,5-tris(trimethylsilyl) phenyl}silane, chlorotris{2,3,6-tris(trimethylsilyl) phenyl}silane, chlorotris{2,4,5-tris(trimethylsilyl) phenyl}silane, chlorotris{2,4,6-tris(trimethylsilyl) phenyl}silane, chlorotris{3,4,5-tris(trimethyl silyl) phenyl}silane, chlorotris{2,3,4,5-tetrakis(trimethylsilyl) phenyl}silane, chlorotris{2,3,4,6-tetrakis(trimethylsilyl) phenyl}silane, chlorotris{2,3,4,5,6-pentakis (trimethylsilyl)phenyl}silane,
chlorotris(2-methyl-3-trimethyl silyl-phenyl)silane, chlorotris(2-methyl-4-trimethylsilyl-phenyl)silane, chlorotris(2-methyl-5-trimethylsilyl-phenyl)silane, chlorotris(2-methyl-6-trimethylsilyl-phenyl)silane, chlorotris{2-methyl-3,4-bis(trimethylsilyl)phenyl}silane, chlorotris{2-methyl-3,5-bis(trimethylsilyl)phenyl}silane, chlorotris{2-methyl-3,6-bis(trimethylsilyl)phenyl}silane, chlorotris{2-methyl-4,5-bis(trimethylsilyl)phenyl}silane, chlorotris{2-methyl-4,6-bis(trimethylsilyl)phenyl}silane, chlorotris{2-methyl-5,6-bis(trimethylsilyl)phenyl}silane, chlorotris{2-methyl-3,4,5-tris(trimethylsilyl)phenyl}silane, chlorotris{2-methyl-3,4,6-tris(trimethylsilyl)phenyl}silane, chlorotris{2-methyl-4,5,6-tris(trimethylsilyl) phenyl}silane, chlorotris{2-methyl-3,4,5,6-tetrakis(trimethylsilyl)phenyl}silane,
chlorotris(3-methyl-2-trimethylsilyl-phenyl)silane, chlorotris(3-methyl-4-trimethylsilyl-phenyl)silane, chlorotris(3-methyl-5-trimethylsilyl-phenyl)silane, chlorotris(3-methyl-6-trimethylsilyl-phenyl)silane, chlorotris{3-methyl-2,4-bis(trimethylsilyl)phenyl}silane, chlorotris{3-methyl-2,5-bis(trimethylsilyl)phenyl}silane, chlorotris{3-methyl-2,6-bis(trimethyl silyl)phenyl}silane, chlorotris{3-methyl-4,5-bis(trimethylsilyl)phenyl}silane, chlorotris{3-methyl-4,6-bis(trimethylsilyl)phenyl}silane, chlorotris{3-methyl-5,6-bis(trimethylsilyl)phenyl}silane, chlorotris{3-methyl-2,4,5-tris(trimethylsilyl)phenyl}silane, chlorotris{3-methyl-2,4,6-tris(trimethylsilyl) phenyl}silane, chlorotris{3-methyl-4,5,6-tris(trimethylsilyl)phenyl}silane, chlorotris{3-methyl-2,4,5,6-tetrakis (trimethylsilyl)phenyl}silane,
chlorotris(4-methyl-2-trimethylsilyl-phenyl)silane, chlorotris(4-methyl-3-trimethylsilyl-phenyl)silane, chlorotris{4-methyl-2,3-bis(trimethylsilyl)phenyl}silane, chlorotris{4-methyl-2,5-bis(trimethylsilyl)phenyl}silane, chlorotris{4-methyl-2,6-bis(trimethylsilyl)phenyl}silane, chlorotris{4-methyl-3,5-bis(trimethylsilyl)phenyl}silane, chlorotris{4-methyl-2,3,5-tris(trimethylsilyl)phenyl}silane, chlorotris{4-methyl-2,3,6-tris(trimethylsilyl) phenyl}silane, chlorotris{4-methyl-2,3,5,6-tetrakis(trimethylsilyl)phenyl}silane,
chlorotris(2,3-dimethyl-4-trimethylsilyl-phenyl)silane, chlorotris(2,3-dimethyl-5-trimethylsilyl-phenyl)silane, chlorotris(2,3-dimethyl-6-trimethylsilyl-phenyl)silane, chlorotris{2,3-dimethyl-4,5-bis(trimethylsilyl)-phenyl}silane, chlorotris{2,3-dimethyl-4,6-bis(trimethylsilyl)-phenyl}silane, chlorotris{2,3-dimethyl-5,6-bis(trimethylsilyl)-phenyl}silane, chlorotris{2,3-dimethyl-4,5, 6-tris(trimethylsilyl)-phenyl}silane,
chlorotris(2,4-dimethyl-3-trimethylsilyl-phenyl)silane, chlorotris(2,4-dimethyl-5-trimethylsilyl-phenyl)silane, chlorotris(2,4-dimethyl-6-trimethylsilyl-phenyl)silane, chlorotris{2,4-dimethyl-2,5-bis(trimethylsilyl)-phenyl}silane, chlorotris{2,4-dimethyl-2,6-bis(trimethylsilyl)-phenyl}silane, chlorotris{2,4-dimethyl-5,6-bis(trimethylsilyl)-phenyl}silane, chlorotris{2,4-dimethyl-2,5,6-tris(trimethylsilyl)-phenyl}silane, chlorotris(2,5-dimethyl-3-trimethylsilyl-phenyl)silane, chlorotris(2,5-dimethyl-4-trimethylsilyl-phenyl)silane, chlorotris(2,5-dimethyl-6-trimethylsilyl-phenyl)silane, chlorotris{2,5-dimethyl-3,4-bis(trimethylsilyl)-phenyl}silane, chlorotris{2,5-dimethyl-3,6-bis(trimethylsilyl)-phenyl}silane, chlorotris{2,5-dimethyl-4,6-bis(trimethylsilyl)-phenyl}silane, chlorotris{2,5-dimethyl-3,4,6-tris(trimethylsilyl)-phenyl}silane, chlorotris(2,6-dimethyl-3-trimethylsilyl-phenyl)silane, chlorotris(2,6-dimethyl-4-trimethylsilyl-phenyl)silane, chlorotris{2,6-dimethyl-3,4-bis(trimethylsilyl)-phenyl}silane, chlorotris{2,6-dimethyl-3,5-bis(trimethylsilyl)-phenyl}silane, chlorotris{2,6-dimethyl-3,4,5-tris(trimethylsilyl)-phenyl}silane, chlorotris(3,4-dimethyl-2-trimethylsilyl-phenyl)silane, chlorotris(3,4-dimethyl-5-trimethylsilyl-phenyl)silane, chlorotris(3,4-dimethyl-6-trimethylsilyl-phenyl)silane, chlorotris{3,4-dimethyl-2,5-bis(trimethylsilyl)-phenyl}silane, chlorotris{3,4-dimethyl-2,6-bis(trimethylsilyl)-phenyl}silane, chlorotris{3,4-dimethyl-5,6-bis(trimethylsilyl)-phenyl}silane, chlorotris{3,4-dimethyl-2,5,6-tris(trimethylsilyl)-phenyl}silane, chlorotris(3,5-dimethyl-2-trimethylsilyl-phenyl)silane, chlorotris(3,5-dimethyl-4-trimethylsilyl-phenyl)silane, chlorotris{3,5-dimethyl-2,4-bis(trimethylsilyl)-phenyl}silane, chlorotris{3,5-dimethyl-2,4,6-tris(trimethylsilyl)-phenyl}silane, chlorotris(2-methoxyphenyl)silane, chlorotris(3-methoxyphenyl)silane, chlorotris(4-methoxyphenyl)silane, chlorotris{2,3-dimethoxyphenyl}silane, chlorotris{2,4-dimethoxyphenyl}silane, chlorotris{2,5-dimethoxyphenyl}silane, chlorotris{2,6-dimethoxyphenyl}silane, chlorotris{3,4-dimethoxyphenyl}silane, chlorotris{3,5-dimethoxyphenyl}silane, chlorotris{2,3,4-trimethoxyphenyl}silane, chlorotris{2,3,5-trimethoxyphenyl}silane, chlorotris{2,3,6-trimethoxyphenyl}silane, chlorotris{2,4,5-trimethoxyphenyl}silane, chlorotris{2,4,6-trimethoxyphenyl}silane, chlorotris{3,4,5-trimethoxyphenyl}silane, chlorotris{2,3,4,5-tetramethoxyphenyl}silane, chlorotris{2,3,4,6-tetramethoxyphenyl}silane, chlorotris{2,3,4,5,6-pentamethoxyphenyl}silane, chlorotris(2-methyl-3-methoxyphenyl)silane, chlorotris(2-methyl-4-methoxyphenyl)silane, chlorotris(2-methyl-5-methoxyphenyl)silane, chlorotris(2-methyl-6-methoxyphenyl)silane, chlorotris{2-methyl-3,4-dimethoxyphenyl}silane, chlorotris{2-methyl-3,5-dimethoxyphenyl}silane, chlorotris{2-methyl-3,6-dimethoxyphenyl}silane, chlorotris{2-methyl-4,5-dimethoxyphenyl}silane, chlorotris{2-methyl-4,6-dimethoxyphenyl}silane, chlorotris{2-methyl-5,6-dimethoxyphenyl}silane, chlorotris{2-methyl-3,4,5-trimethoxyphenyl}silane, chlorotris{2-methyl-3,4,6-trimethoxyphenyl}silane, chlorotris{2-methyl-4,5,6-trimethoxyphenyl}silane, chlorotris{2-methyl-3,4,5,6-tetramethoxyphenyl}silane, chlorotris(3-methyl-2-methoxyphenyl)silane, chlorotris(3-methyl-4-methoxyphenyl)silane, chlorotris(3-methyl-5-methoxyphenyl)silane, chlorotris(3-methyl-6-methoxyphenyl)silane, chlorotris{3-methyl-2,4-dimethoxyphenyl}silane, chlorotris{3-methyl-2,5-dimethoxyphenyl}silane, chlorotris{3-methyl-2,6-dimethoxyphenyl}silane, chlorotris{3-methyl-4,5-dimethoxyphenyl}silane, chlorotris{3-methyl-4,6-dimethoxyphenyl}silane, chlorotris{3-methyl-5,6-dimethoxyphenyl}silane, chlorotris{3-methyl-2,4,5-trimethoxyphenyl}silane, chlorotris{3-methyl-2,4,6-trimethoxyphenyl}silane, chlorotris{3-methyl-4,5,6-trimethoxyphenyl}silane, chlorotris{3-methyl-2,4,5,6-tetramethoxyphenyl}silane, chlorotris(4-methyl-2-methoxyphenyl)silane, chlorotris(4-methyl-3-methoxyphenyl)silane, chlorotris{4-methyl-2,3-dimethoxyphenyl}silane, chlorotris{4-methyl-2,5-dimethoxyphenyl}silane, chlorotris{4-methyl-2,6-dimethoxyphenyl}silane, chlorotris{4-methyl-3,5-dimethoxyphenyl}silane, chlorotris{4-methyl-2,3,5-trimethoxyphenyl}silane, chlorotris{4-methyl-2,3,6-trimethoxyphenyl}silane, chlorotris{4-methyl-2,3,5,6-tetramethoxyphenyl}silane, chlorotris(2-dimethylaminophenyl)silane, chlorotris(3-dimethylaminophenyl)silane, chlorotris(4-dimethylaminophenyl)silane, chlorotris{2,3-bis(dimethylamino)phenyl}silane, chlorotris{2,4-bis(dimethylamino)phenyl}silane, chlorotris{2,5-bis(dimethylamino)phenyl}silane, chlorotris{2,6-bis(dimethylamino)phenyl}silane, chlorotris{3,4-bis(dimethylamino)phenyl}silane, chlorotris{3,5-bis(dimethylamino)phenyl}silane, chlorotris{2,3,4-tris(dimethylamino)phenyl}silane, chlorotris{2,3,5-tris(dimethylamino)phenyl}silane, chlorotris{2,3,6-tris(dimethylamino)phenyl}silane, chlorotris{2,4,5-tris(dimethylamino)phenyl}silane, chlorotris{2,4,6-tris(dimethylamino)phenyl}silane, chlorotris{3,4,5-tris(dimethylamino)phenyl}silane, chlorotris{2,3,4,5-tetrakis(dimethylamino)phenyl}silane, chlorotris{2,3,4,6-tetrakis(dimethylamino)phenyl}silane, chlorotris{2,3,4,5,6-pentakis(dimethylamino)phenyl}silane, chlorotris(2-methyl-3-dimethylaminophenyl)silane, chlorotris(2-methyl-4-dimethylaminophenyl)silane, chlorotris(2-methyl-5-dimethylaminophenyl)silane, chlorotris(2-methyl-6-dimethylaminophenyl)silane, chlorotris{2-methyl-3,4-bis(dimethylamino)phenyl}silane, chlorotris{2-methyl-3,5-bis(dimethylamino)phenyl}silane, chlorotris{2-methyl-3,6-bis(dimethylamino)phenyl}silane, chlorotris{2-methyl-4,5-bis(dimethylamino)phenyl}silane, chlorotris{2-methyl-4,6-bis(dimethylamino)phenyl}silane, chlorotris{2-methyl-5,6-bis(dimethylamino)phenyl}silane, chlorotris{2-methyl-3,4,5-tris(dimethylamino)phenyl}silane, chlorotris{2-methyl-3,4,6-tris(dimethylamino)phenyl}silane, chlorotris{2-methyl-4,5,6-tris(dimethylamino)phenyl}silane, chlorotris{2-methyl-3,4,5,6-tetrakis(dimethylamino)phenyl}silane, chlorotris(3-methyl-2-dimethylaminophenyl)silane, chlorotris(3-methyl-4-dimethylaminophenyl)silane, chlorotris(3-methyl-5-dimethylaminophenyl)silane, chlorotris(3-methyl-6-dimethylaminophenyl)silane, chlorotris{3-methyl-2,4-bis(dimethylamino)phenyl}silane, chlorotris{3-methyl-2,5-bis(dimethylamino)phenyl}silane, chlorotris{3-methyl-2,6-bis(dimethylamino)phenyl}silane, chlorotris{3-methyl-4,5-bis(dimethylamino)phenyl}silane, chlorotris{3-methyl-4,6-bis(dimethylamino)phenyl}silane, chlorotris{3-methyl-5,6-bis(dimethylamino)phenyl}silane, chlorotris{3-methyl-2,4,5-tris(dimethylamino)phenyl}silane, chlorotris{3-methyl-2,4,6-tris(dimethylamino)phenyl}silane, chlorotris{3- methyl-4,5,6-tris(dimethylamino)phenyl}silane, chlorotris{3-methyl-2,4,5,6-tetrakis(dimethylamino)phenyl}silane, chlorotris(4-methyl-2-dimethylaminophenyl)silane, chlorotris(4-methyl-3-dimethylaminophenyl)silane, chlorotris{4-methyl-2,3-bis(dimethylamino)phenyl}silane, chlorotris{4-methyl-2,5-bis(dimethylamino)phenyl}silane, chlorotris{4-methyl-2,6-bis(dimethylamino)phenyl}silane, chlorotris{4-methyl-3,5-bis(dimethylamino)phenyl}silane, chlorotris{4-methyl-2,3,5-tris(dimethylamino)phenyl}silane, chlorotris{4-methyl-2,3,6-tris(dimethylamino)phenyl}silane and chlorotris{4-methyl-2,3,5,6-tetrakis(dimethylamino)phenyl}silane.

Compounds obtained by substituting "fluoro", "bromo" or "iodo" for "chloro" in these compounds exemplified above are also included therein.

Examples of the base reacted with the substituted cyclopentadiene compound (4) include: alkali metal hydride such as lithium hydride, sodium hydride and potassium hydride; alkaline earth metal hydride such as calcium hydride; and organic alkali metal compounds typified by organic lithium compounds such as methyllithium, ethyllithium, n-butyllithium, sec-butyllithium, tert-butyllithium, lithiumtrimethylsilyl acetylide, lithium acetylide, trimethylsilylmethyllithium, vinyllithium, phenyllithium and allyllithium. The amount thereof used is usually in the range of 0.5- to 3-fold by mol, preferably 0.9- to 2-fold by mol, with respect to the substituted cyclopentadiene compound (4). A usual commercially available mineral oil-containing product can be used directly as sodium hydride or potassium hydride. Of course, the mineral oil may be removed, for use, by washing with a hydrocarbyl solvent such as hexane.

In the step of reacting the substituted cyclopentadiene compound (4) with a base, an amine compound may be used. Examples of such an amine compound include: primary anilines such as aniline, chloroaniline, bromoaniline, fluoroaniline, dichloroaniline, dibromoaniline, difluoroaniline, trichloroaniline, tribromoaniline, trifluoroaniline, tetrachloroaniline, tetrabromoaniline, tetrafluoroaniline, pentachloroaniline, pentafluoroaniline, nitroaniline, dinitroaniline, hydroxyaniline, phenylenediamine, anisidine, dimethoxyaniline, trimethoxyaniline, ethoxyaniline, diethoxyaniline, triethoxyaniline, n-propoxyaniline, isopropoxyaniline, n-butoxyaniline, sec-butoxyaniline, isobutoxyaniline, t-butoxyaniline, phenoxyaniline, methylaniline, ethylaniline, n-propylaniline, isopropylaniline, n-butylaniline, sec-butylaniline, isobutylaniline, t-butylaniline, dimethylaniline, diethylaniline, di-n propylaniline, diisopropylaniline, di-n-butylaniline, di-sec-butylaniline, diisobutylaniline, di-t-butylaniline, trimethylaniline, triethylaniline, diisopropylaniline, phenylaniline, benzylaniline, aminobenzoic acid, methyl aminobenzoate, ethyl aminobenzoate, n-propyl aminobenzoate, isopropyl aminobenzoate, n-butyl aminobenzoate, isobutyl aminobenzoate, sec-butyl aminobenzoate and t-butyl aminobenzoate, and other primary amines including naphthylamine, naphthylmethylamine, benzylamine, propylamine, butylamine, pentylamine, hexylamine, cyclohexylamine, heptylamine, octylamine, 2-aminopyridine, 3-aminopyridine and 4-aminopyridine;

secondary amines such as N-methylaniline, N-ethylaniline, diphenylamine, N-methylchloroaniline, N-methylbromoaniline, N-methylfluoroaniline, N-methylanisidine, N-methylmethylaniline, N-methylethylaniline, N-methyl-n-propylaniline, N-methyl isopropylaniline, diethylamine, dipropylamine, diisopropylamine, dipentylamine, dihexylamine, dicyclohexylamine, diheptylamine, dioctylamine, morpholine, piperidine, 2,2,6,6-tetramethylpiperidine, pyrrolidine, 2-methylaminopyridine, 3-methylaminopyridine and 4-methylaminopyridine; and tertiary amines such as N,N-dimethylaniline, N,N-dimethylchloroaniline, N,N-dimethylbromoaniline, N,N-dimethylfluoroaniline, N,N-dimethylanisidine, N,N-dimethylethylaniline, N,N-dimethyl-n-propylaniline, N,N-dimethylisopropylaniline, 1,4-diazabicyclo[2.2.2]octane, 1,5-diazabicyclo[4.3.0]non-5-ene, 1,8-diazabicyclo[5.4.0]undec-7-ene, 2-dimethylaminopyridine, 3-dimethylaminopyridine, 4-dimethylaminopyridine, trimethylamine, triethylamine, tri-n-propylamine, tri-n-butylamine, diisopropylethylamine, tri-n-octylamine, tri-n-decylamine and triphenylamine. Preferably primary or secondary amines, more preferably primary amines are used.

The amount of such an amine compound used is usually in the range of 0.001- to 2-fold by mol, preferably 0.01- to 0.5-fold by mol, with respect to the base. The reaction is usually performed in a solvent inert to the reaction. Examples of such a solvent include aprotic solvents such as: aromatic hydrocarbyl solvents such as benzene, toluene and xylene; aliphatic hydrocarbyl solvents such as pentane, hexane, heptane, octane and cyclohexane; ether solvents such as diethyl ether, methyl t-butyl ether, tetrahydrofuran and 1,4-dioxane; amide solvents such as hexamethylphosphoric amide, dimethylformamide, dimethylacetamide and N-methylpyrrolidone; and halogen solvents such as chlorobenzene and dichlorobenzene. These solvents are used alone or as a mixture of two or more thereof, and the amount thereof used is usually in the range of 1- to 200-fold by weight, preferably 3- to 30-fold by weight, with respect to each cyclopentadiene.

For the reaction, for example, the substituted cyclopentadiene compound (4), the base and the amine compound may be mixed simultaneously in a solvent, or the base and the amine compound are mixed in advance and then the substituted cyclopentadiene compound (4) may be added to the mixture. The reaction temperature is not particularly limited, and a temperature region that eliminates the need of low temperature equipment is industrially preferable and is, for example, in the range of from 0 to 70° C., preferably from 10 to 60° C. This reaction efficiently produces a metal salt of the substituted cyclopentadiene compound (4). The metal salt of the substituted cyclopentadiene compound (4) thus obtained may be used directly in the form of the reaction mixture or may be taken from the reaction mixture. The former case usually suffices.

The reaction for obtaining the substituted cyclopentadiene compound (2) is usually performed in a solvent inert to the reaction. Examples of such a solvent include aprotic solvents such as: aromatic hydrocarbyl solvents such as benzene, toluene and xylene; aliphatic hydrocarbyl solvents such as pentane, hexane, heptane, octane and cyclohexane; ether solvents such as diethyl ether, methyl t-butyl ether, tetrahydrofuran and 1,4-dioxane; amide solvents such as hexamethylphosphoric amide, dimethylformamide, dimethylacetamide and N-methylpyrrolidone; and halogen solvents such as chlorobenzene and dichlorobenzene. These solvents are used alone or as a mixture of two or more thereof, and the amount thereof used is usually in the range of 1- to 200-fold by weight, preferably 3- to 30-fold by weight, with respect to the substituted cyclopentadiene compound (4). This reaction is usually performed, for example, by mixing the base, the amine compound and the substituted cyclopentadiene compound (4) in a solvent and then adding the halogenated silyl compound (5) to the mixture. However, even when a method is adopted in which these components are mixed simultaneously, the substituted cyclopentadiene compound (2) of interest is produced. The reaction temperature is not particularly limited, and a temperature region that eliminates the need of low temperature equipment is industrially advantageous and is, for example, in the range of from 0 to 70° C., preferably from 10 to 60° C.

The amount of the substituted cyclopentadiene compound (4) used is usually in the range of 0.5- to 5-fold by mol, preferably 0.8- to 3-fold by mol, with respect to the halogenated silyl compound (5).

After completion of the reaction, water, an aqueous sodium bicarbonate solution, an aqueous sodium carbonate solution, an aqueous ammonium chloride solution or an aqueous solution of hydrochloric acid or the like is added to the obtained reaction mixture. Then, organic and aqueous layers are separated to obtain a solution of the substituted cyclopentadiene compound (2) as the organic layer. When a water-compatible solvent is used in the reaction or when the amount of the solvent used in the reaction is too small to easily separate organic and aqueous layers, a water-insoluble organic solvent such as toluene, ethyl acetate or chlorobenzene may be added to the reaction mixture as appropriate, followed by separation into organic and aqueous layers. The obtained organic layer is concentrated to obtain the substituted cyclopentadiene compound (2). The obtained substituted cyclopentadiene compound (8-1) may be purified, if necessary, by a method such as distillation and column chromatography treatment.

<Activating Co-Catalyst Component>

Examples of the activating co-catalyst component include the following compound (A) and compound (B). Compound (A) and compound (B) may be used in combination.

compound (A): one or more aluminum compounds selected from the compound group consisting of the following compounds (A1), (A2) and (A3):

(A1): an organic aluminum compound represented by formula $(E^1)_a Al(G)_{3-a}$, (A2): cyclic aluminoxane having a structure represented by formula $\{-Al(E^2)-O-\}_b$, and (A3): linear aluminoxane having a structure represented by formula $E^3\{-Al(E^3)-O-\}_c Al(E^3)_2$, wherein $E^1$, $E^2$ and $E^3$ represent a hydrocarbyl group having 1 to 8 carbon atoms; G represents a hydrogen atom or a halogen atom; a represents an integer of 1 to 3; b represents an integer of 2 or more; c represents an integer of 1 or more; in the case that more than one $E^1$ moieties exist, the $E^1$ moieties may be the same as or different from each other; in the case that more than one G moieties exist, the G moieties may be the same as or different from each other; a plurality of $E^2$ moieties may be the same as or different from each other; and a plurality of $E^3$ moieties may be the same as or different from each other.

compound (B): one or more boron compounds selected from the compound group consisting of the following compounds (B1), (B2) and (B3):

(B1): a boron compound represented by formula $BQ^1Q^2Q^3$, (B2): a boron compound represented by formula $T^+(BQ^4Q^5Q^6Q^7)^-$, and (B3): a borate compound represented by formula $(L-H)^+ (BQ^8Q^9Q^{10}Q^{11})^-$, wherein B represents a trivalent boron; $Q^1$, $Q^2$, $Q^3$, $Q^4$, $Q^5$, $Q^6$, $Q^7$, $Q^8$, $Q^9$, $Q^{10}$ and $Q^{11}$ are the same as or different from each other and each independently represent a halogen atom, a hydrocarbyl group having 1 to 20 carbon atoms which may have a halogen atom as a substituent, a hydrocarbylsilyl group having 1 to 20 carbon atoms which may have a halogen atom as a substituent, an alkoxy group having 1 to 20 carbon atoms which may have a halogen atom as a substituent or a dihydrocarbylamino group having 2 to 20 carbon atoms which may have a halogen atom as a substituent; $T^+$ represents an inorganic or organic cation; and $(L-H)^+$ represents Broensted acid.

In the compounds (A1) to (A3), examples of the hydrocarbyl group having 1 to 8 carbon atoms in $E^1$, $E^2$ and $E^3$, include alkyl groups having 1 to 8 carbon atoms. Examples of the alkyl groups having 1 to 8 carbon atoms include methyl, ethyl, normal propyl, isopropyl, normal butyl, isobutyl, normal pentyl and neopentyl groups.

Examples of the organic aluminum compound (A1) represented by formula $(E^1)_a Al(G)_{3-a}$ include trialkylaluminum, dialkylaluminum chloride, alkylaluminum dichloride and dialkylaluminum hydride. Examples of the trialkylaluminum include trimethylaluminum, triethylaluminum, tripropylaluminum, triisobutylaluminum and trihexylaluminum. Examples of the dialkylaluminum chloride include dimethylaluminum chloride, diethylaluminum chloride, dipropylaluminum chloride, diisobutylaluminum chloride and dihexylaluminum chloride. Examples of the alkylaluminum dichloride include methylaluminum dichloride, ethylaluminum dichloride, propylaluminum dichloride, isobutylaluminum dichloride and hexylaluminum dichloride. Examples of the dialkylaluminum hydride include dimethylaluminum hydride, diethylaluminum hydride, dipropylaluminum hydride, diisobutylaluminum hydride and dihexylaluminum hydride.

Examples of $E^2$ and $E^3$ in (A2): cyclic aluminoxane having a structure represented by formula $\{-Al(E^2)-O-\}_b$ and (A3): linear aluminoxane having a structure represented by formula $E^3\{-Al(E^3)-O-\}_c Al(E^3)_2$ include alkyl groups such as methyl, ethyl, normal propyl, isopropyl, normal butyl, isobutyl, normal pentyl and neopentyl groups, b is an integer of 2 or more, and c is an integer of 1 or more. Preferably, $E^2$ and $E^3$ are each independently a methyl group or an isobutyl group, b is 2 to 40, and c is 1 to 40.

These aluminoxanes are prepared by various methods. The methods are not particularly limited, and they may be prepared according to methods known in the art. For example, a solution containing trialkylaluminum (e.g., trimethylaluminum) dissolved in an appropriate organic solvent (e.g., benzene or aliphatic hydrocarbyl) is contacted with water to prepare the aluminoxanes. Another preparation method can involve, for example, contacting trialkylaluminum (e.g., trimethylaluminum) with metal salt (e.g., copper sulfate hydrate) containing crystalline water.

In the compounds (B1) to (B3), $Q^1$, $Q^2$, $Q^3$, $Q^4$, $Q^5$, $Q^6$, $Q^7$, $Q^8$, $Q^9$, $Q^{10}$ and are preferably a halogen atom or a hydrocarbyl group having 1 to 20 carbon atoms which may be substituted by a halogen atom. Examples of the inorganic cation in $T^+$ include ferrocenium cation, alkyl-substituted ferrocenium cation and silver cation. Examples of the organic cation include triphenylmethyl cation. Examples of $(BQ^4Q^5Q^6Q^7)^-$ and $(BQ^8Q^9Q^{10}Q^{11})^-$ include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,3,4-trifluorophenyl)borate, phenyltris(pentafluorophenyl)borate, tetrakis(3,5-bistrifluoromethylphenyl)borate. Examples of the Broensted acid represented by $(L-H)^+$ include trialkyl-substituted ammonium, N,N-dialkylanilinium, dialkylammonium and triarylphosphonium.

Examples of the boron compound (B1) represented by formula $BQ^1Q^2Q^3$ include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane and phenylbis(pentafluorophenyl)borane.

Examples of the borate compound (B2) represented by formula $T^+(BQ^4Q^5Q^6Q^7)^-$ include ferrocenium tetrakis(pentafluorophenyl)borate, 1,1'-bis-trimethylsilylferrocenium tetrakis(pentafluorophenyl)borate, silver tetrakis(pentafluorophenyl)borate, triphenylmethyl tetrakis(pentafluorophenyl)borate and triphenylmethyl tetrakis(3,5-bistrifluoromethylphenyl)borate.

Examples of the borate compound (B3) represented by formula $(L-H)(BQ^8Q^9Q^{10}Q^{11})^-$ include triethylammonium tetrakis(pentafluorophenyl)borate, tripropylammonium tetrakis(pentafluorophenyl)borate, tri(normal butyl)ammonium tetrakis(pentafluorophenyl)borate, tri(normal butyl)ammonium tetrakis(3,5-bistrifluoromethylphenyl)borate, N,N-dimethylanilinium tetrakis(pentafluorophenyl)borate, N,N-bis-trimethylsilylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-bis-trimethylsilylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate, tri(bis-trimethylsilylphenyl)phosphonium tetrakis(pentafluorophenyl)borate and tri(dimethylphenyl)phosphonium tetrakis(pentafluorophenyl)borate.

<Catalyst for Trimerization>

The catalyst for trimerization of the present invention is a catalyst for trimerization obtained by contacting the transition metal complex (1) with an activating co-catalyst component and is a catalyst capable of producing 1-hexene by ethylene trimerization. The transition metal complex (1) and the activating co-catalyst component may each be referred to as a catalytic component.

Examples of such an activating co-catalyst component can include the compounds (A) and (B) described above. Moreover, these compounds (A) and (B) may be used in combination.

In the amount of each catalytic component used, a molar ratio between the compound (A) (in terms of the aluminum atom) and the transition metal complex (1) used as a catalytic component (compound (A) (in terms of the aluminum atom)/transition metal complex (1)) is usually 0.01 to 10000, preferably 5 to 5000. Moreover, a molar ratio between the compound (B) and the transition metal complex (1) used as a catalytic component (compound (B)/transition metal complex (1)) is usually 0.01 to 100, preferably 0.5 to 10.

When each catalytic component is used in a solution state, the concentration of the transition metal complex (1) used as a catalytic component is usually 0.0001 to 5 mmol/L, preferably 0.001 to 1 mmol/L. The concentration of the compound (A) is usually 0.01 to 500 mmol/L, preferably 0.1 to 100 mmol/L, in terms of the aluminum atom. The concentration of the compound (B) is usually 0.0001 to 5 mmol/L, preferably 0.001 to 1 mmol/L.

The method for contacting each catalytic component is not particularly limited. The transition metal complex (1) may be brought into contact with the activating co-catalyst component in advance to prepare a catalyst for trimerization, which is then supplied to a reactor. Alternatively, these catalytic components may be supplied to a reactor in any order and brought into contact with each other in the reactor.

<Method for Producing 1-hexene>

The method for producing 1-hexene according to the present invention is a method for producing 1-hexene from ethylene and is a method for producing 1-hexene by the trimerization reaction of ethylene in, the presence of the catalyst for trimerization.

The trimerization reaction is not particularly limited and may be, for example, trimerization reaction using aliphatic hydrocarbyl (e.g., butane, pentane, hexane, heptane and octane), aromatic hydrocarbyl (e.g., benzene and toluene) or halogenated hydrocarbyl (e.g., methylene dichloride and chlorobenzene) as a solvent, trimerization reaction in a slurry state, or trimerization reaction in ethylene in a gas state.

The trimerization reaction can be performed by any of batch, semi-continuous and continuous methods.

The pressure of ethylene in the trimerization reaction is usually in the range of normal pressure to 10 MPa, preferably in the range of normal pressure to 5 MPa.

The temperature of the trimerization reaction can usually be in the range of from −50° C. to +220° C. and is preferably in the range of from 0° C. to 170° C., more preferably in the range of from 50° C. to 120° C.

The time of the trimerization reaction can generally be determined appropriately according to the reaction apparatus of interest and can be in the range of 1 minute to 20 hours.

EXAMPLES

The present invention will be described by way of Examples and Comparative Examples below.

<Production of Transition Metal Complex>

Physical properties were measured by the following methods.

(1) Proton Nuclear Magnetic Resonance Spectrum ($^1$H-NMR)

Apparatus: DPX300 manufactured by Bruker BioSpin.
Sample cell: Tube (5 mm in diameter)
Measurement solvent: $CDCl_3$
Sample concentration: about 10 mg/0.5 mL
Measurement temperature: Room temperature (about 25° C.)
Measurement parameter: Probe (5 mm in diameter), OBNUC $^1$H, PULPROG zg30, accumulated number 16 times or more
Repeat time: ACQTM 2.7 seconds, PD 1 second
Internal standard: $CDCl_3$ (7.26 ppm)

(2) Carbon nuclear magnetic resonance spectrum ($^{13}$C-NMR)

Apparatus: DPX300 manufactured by Bruker BioSpin.
Sample cell: Tube (5 mm in diameter)
Measurement solvent: $CDCl_3$
Sample concentration: about 10 mg/0.5 mL
Measurement temperature: Room temperature (about 25° C.)
Measurement parameter: Probe (5 mm in diameter), OBNUC $^{13}$C, PULPROG zgpg30, accumulated number 256 times or more
Repeat time: ACQTM 1.36 seconds, PD 2 seconds
Internal standard: $CDCl_3$ (77.0 ppm)

(3) Electron ionization mass spectrometry (EI-MS)

Apparatus: JMS-T100GC manufactured by JEOL Ltd.
Ionization voltage: 70 eV
Ion source temperature: 230° C.
Acceleration voltage: 7 kV
MASS RANGE: m/z 35-1200

(4) Field Desorption Mass Spectrometry (FD-MS)

Apparatus: JEOL Ltd., JMS-700
Acceleration voltage: 8 kV
Cathode: 0 kV
Carbon emitter
MASS RANGE: m/z 10-2000

Example 1

Synthesis of [1-tris(3-trimethylsilyl-phenyl)silyl-2,3, 4,5-tetramethylcyclopentadienyl]titanium trichloride (hereinafter referred to as "complex 1")

Synthesis of chlorotris(3-trimethylsilylphenyl)silane

Under a nitrogen atmosphere, diethyl ether (100 mL) was added to 1-bromo-3-trimethylsilylbenzene (20.00 g, 87.27 mmol). The resultant mixture was cooled to −78° C., a 1.65 M hexane solution of n-butyllithium (53.73 mL, 88.65 mmol) was added dropwise. The mixture was warmed to 0° C. and stirring was performed for 2 hours at the same temperature. The obtained mixture was transferred at −78° C. to a solution of tetrachlorosilane (4.71 g, 27.70 mmol) dissolved in diethyl ether (33 mL). After stirring was performed at −78° C. for 50 minutes, the mixture was gradually warmed to room temperature. After completion of the reaction, the solvent was removed under reduced pressure. Thereafter, hexane was added to the residue, and insoluble materials were removed by filtration. Removal of the solvent from the filtrate under reduced pressure gave chlorotris(3-trimethylsilylphenyl)silane quantitatively.

$^1$H-NMR (CDCl$_3$, δ ppm): 0.20 (s, 27H), 7.36 (t, J=7.3 Hz, 3H), 7.60 (d, J=8.4 Hz, 6H), 7.79 (s, 3H)
$^{13}$C-NMR (CDCl$_3$, δ ppm): −1.02, 127.44, 132.25, 135.75, 135.80, 140.15, 140.22
Mass spec (EI-MS, m/z): 510 (M$^+$)

Synthesis of 1-tris(3-trimethylsilylphenyl)silyl-2,3,4, 5-tetramethylcyclopentadiene Under a nitrogen atmosphere, potassium hydride dispersed in mineral oil was washed with hexane to remove the mineral oil. Thereafter, the resultant potassium hydride (1.20 g, 30.00 mmol) and tetrahydrofuran (43 mL) were mixed. The resultant mixture was heated to 50° C. and a solution of 1,2,3,4-tetramethylcyclopenta-1,3-diene (2.69 g, 22.00 mmol) dissolved in tetrahydrofuran (9 mL) was added dropwise. Stirring was performed at 50° C. for 3 hours and 30 minutes. To this solution, a solution of chlorotris(3-trimethylsilylphenyl)silane (10.23 g, 20.00 mmol) dissolved in tetrahydrofuran (43 mL) was added dropwise. Stirring was performed at 50° C. for 8 hours. The resultant mixture was added dropwise at 0° C. to a 10% aqueous sodium carbonate solution (40 ml). Toluene (60 mL) was added to separate an organic phase, and the organic phase was washed with water (60 mL) twice, and further washed with saturated brine (60 mL). The organic phase was dried over sodium sulfate and then filtrated. The solvent was removed under reduced pressure. Purification was performed by silica gel column chromatography to obtain 1-tris(3,5-trimethylsilylphenyl)silyl-2,3,4,5-tetramethylcyclopentadiene (7.08 g, yield 59.3%).

$^1$H-NMR (CDCl$_3$, δ ppm): 0.20 (s, 27H), 1.51 (s, 6H), 1.54 (s, 6H), 3.76 (s, 1H), 7.19-7.33 (m, 3H), 7.46-7.60 (m, 6H), 7.77 (s, 3H)
Mass spec (EI-MS, nah): 596 (M)

"Synthesis of Complex 1"

Under a nitrogen atmosphere, to a toluene solution (20 mL) of 1-tris(3-trimethylsilylphenyl)silyl-2,3,4,5-tetramethylcyclopentadiene (0.88 g, 1.47 mmol) and triethylamine (0.75 g, 7.37 mmol), a 1.65 M hexane solution of n-butyllithium (0.98 mL, 1.62 mmol) was added dropwise at −78° C. After the mixture was gradually warmed to room temperature, stirring was performed at 50° C. for 7 hours. The resultant mixture was cooled to −45° C. and a solution of titanium tetrachloride (0.31 g, 1.62 mmol) dissolved in toluene (2 mL) was added dropwise at the same temperature. After the mixture was gradually warmed to room temperature, stirring was performed at room temperature overnight. After completion of the reaction, the solvent was removed under reduced pressure. Thereafter, heptane was added to the residue, and insoluble materials were removed by filtration. The solvent was removed from the filtrate under reduced pressure. Pentane was added to the resultant solid, and insoluble materials were removed by filtration. Removal of the solvent from the filtrate under reduced pressure, gave a mixture of complex 1 and 2,2'-bis{tris(3-trimethylsilylphenyl)silyl}1,1',3,3',4,4',5,5'-octamethyl-5,5'-bi-1,3-cyclopentadienyl as orange solids. The content of complex 1 determined by $^1$H-NMR using ferrocene as an internal standard was 11.7 wt % (76.4 mg, yield 6.9%).

$^1$H-NMR (CDCl$_3$, δ ppm): 0.18 (s, 27H), 1.99 (s, 6H), 2.33 (s, 6H), 7.16-7.35 (m, 3H), 7.42-7.61 (m, 6H), 7.76 (s, 3H)
Mass spec (EI-MS, m/z): 750 (M$^-$)

Example 2

Synthesis of [1-tris(5-methyl-3-trimethylsilyl-phenyl)silyl-2,3,4,5-tetramethylcyclopentadienyl]titanium trichloride (hereinafter referred to as "complex 2")

Synthesis of chlorotris(5-methyl-3-trimethylsilyl-phenyl)silane

Under a nitrogen atmosphere, 5-methyl-3-trimethylsilyl-1-bromobenzene (20.06 g, 82.49 mmol) and diethyl ether (200 mL) were mixed. The resultant mixture was cooled to −78° C. and a 1.65 M hexane solution of n-butyllithium (50.00 mL, 82.49 mmol) was added dropwise. After the mixture was warmed to 0° C., stirring was performed at this temperature for 3 hours. The resultant mixture was added at −78° C. to a solution of tetrachlorosilane (4.45 g, 26.19 mmol) dissolved in diethyl ether (44 mL). After stirring was performed at −78° C. for 10 minutes, the mixture was gradually warmed to room temperature. After completion of the reaction, the solvent was removed under reduced pressure. Thereafter, hexane was added to the residue, and hexane-insoluble parts were removed by filtration through celite. The solvent was removed from the filtrate under reduced pressure to obtain chlorotris(5-methyl-3-trimethylsilyl-phenyl)silane (13.10 g, yield 90.4%) as a light yellow oil.

$^1$H-NMR (CDCl$_3$, δ ppm): 0.24 (s, 27H), 2.37 (s, 9H), 7.45 (s, 3H), 7.48 (s, 3H), 7.64 (s, 3H)
$^{13}$C-NMR (CDCl$_3$, δ ppm): −0.98, 21.72, 132.25, 136.41, 136.49, 136.62, 137.37, 139.94
Mass Spec (EI-MS, m/z): 552 (M$^+$)

Synthesis of 1-tris(5-methyl-3-trimethylsilyl-phenyl) silyl-2,3,4,5-tetramethylcyclopentadiene Under a nitrogen atmosphere, potassium hydride (0.88 g, 21.82 mmol in terms of potassium hydride) dispersed in mineral oil was washed with hexane. Tetrahydrofuran (38 mL) was added and this mixture was warmed to 50° C. A solution of 1,2,3,4-tetramethylcyclopenta-1,3-diene (2.00 g, 16.37 mmol) dissolved in tetrahydrofuran (8 mL) was added dropwise and stirred at 50° C. for one hour. To this solution, a solution of chlorotris(5-methyl-3-trimethylsilyl-phenyl)silane (7.81 g, 14.11 mmol) dissolved in tetrahydrofuran (38 mL) was added dropwise and stirred at 65° C. for 3 hours. The resultant mixture was added dropwise at 0° C. to a solution of a 10% sodium hydrogen carbonate (38 mL) and a 10% sodium carbonate (38 mL). Toluene (38 mL) was added to separate an organic phase, and the organic phase was dried over sodium sulfate and then filtrated. The solvent was removed under reduced pressure. Purification was performed by silica gel column chromatography to obtain 1-tris(5-methyl-3-trimethylsilyl-phenyl)silyl-2,3,4,5-tetramethylcyclopentadiene (5.40 g, yield 59.9%).

$^1$H-NMR (CDCl$_3$, δ ppm): 0.22 (s, 27H), 1.53 (s, 6H), 1.56 (s, 6H), 2.29 (s, 9H), 3.78 (s, 1H), 7.31 (s, 3H), 7.37 (s, 3H), 7.63 (s, 3H)

$^{13}$C-NMR (CDCl$_3$, δ ppm): −0.90, 11.25, 15.05, 21.77, 51.38, 133.22, 133.52, 134.83, 135.65, 136.92, 136.99, 138.06, 138.79

Mass Spec (EI-MS, m/z): 638 (M$^+$)

"Synthesis of Complex 2"

Under a nitrogen atmosphere, to a toluene solution (55 mL) of 1-tris(5-methyl-3-trimethylsilyl-phenyl)silyl-2,3,4,5-tetramethylcyclopentadiene (1.84 g, 2.88 mmol) and triethylamine (1.46 g, 14.40 mmol), a 1.63 M hexane solution of n-butyllithium (2.12 mL, 3.46 mmol) was added dropwise at −78° C. The mixture was gradually warmed to room temperature and stirring was performed at 50° C. for 8 hours. The obtained mixture was cooled to −50° C. and a solution of titanium(IV) chloride (0.60 g, 3.17 mmol) dissolved in toluene (6 mL) was added dropwise thereto at the same temperature. The mixture was warmed again and stirring was performed overnight at room temperature. After completion of the reaction, the solvent was removed under reduced pressure. Thereafter, heptane was added to the residue, and insoluble materials were removed by filtration. The solvent was removed from the filtrate under reduced pressure. The supernatant obtained by adding pentane was concentrated under reduced pressure, and a mixture of complex 2 and 2,2'-bis{tris(5-methyl-3-trimethylsilyl-phenyl)silyl}-1,1',3,3',4,4',5,5'-octamethyl-5,5'-bi-1,3-cyclopentadienyl was obtained as orange solids. The content of complex 2 determined by $^1$H-NMR using ferrocene as an internal standard was 18.1 wt % (146.0 mg, yield 6.4%).

$^1$H-NMR (CDCl$_3$, δppm): 0.19 (s, 27H), 2.02 (s, 6H), 2.30 (s, 9H), 2.35 (s, 6H), 7.38 (s, 3H), 7.41 (s, 3H), 7.59 (s, 3H)

$^{13}$C-NMR (CDCl$_3$, δppm): −1.17, 14.32, 17.63, 21.61, 131.94, 135.51, 136.11, 137.05, 137.78, 139.21, 139.44, 142.43, 145.83

Mass Spec (EI-MS, m/z): 792 (M$^-$)

Example 3

Synthesis of [1-tris{3,5-bis(trimethylsilyl)phenyl}silyl-2,3,4,5-tetramethylcyclopentadienyl] titanium trichloride (hereinafter referred to as "complex 3")

Synthesis of chlorotris{3,5-bis(trimethylsilyl)phenyl}silane

Under a nitrogen atmosphere, diethyl ether (250 mL) was added to 3,5-bis(trimethylsilyl)-1-bromobenzene (25.03 g, 83.05 mmol). The resultant mixture was cooled to −78° C., a 1.65 M hexane solution of n-butyllithium (50.34 mL, 83.05 mmol) was added dropwise. The mixture was warmed to 0° C. and stirring was performed for 3 hours at the same temperature. The obtained mixture was transferred at −78° C. to a solution of tetrachlorosilane (4.55 g, 26.79 mmol) dissolved in diethyl ether (46 mL). After stirring at −78° C. for 10 minutes, the mixture was gradually warmed to room temperature. After completion of the reaction, the solvent was removed under reduced pressure. Thereafter, hexane was added to the residue, and hexane-soluble fraction was removed by Celite filtration. The hexane-insoluble fraction was extracted with toluene. The solvent was removed from the obtained toluene extract under reduced pressure. Pentane was added and the resultant solid was filtrated and washed with a small amount of pentane, and then, dried under reduced pressure to obtain chlorotris{3,5-bis(trimethylsilyl)phenyl}silane (13.55 g, yield 69.6%) as a white solid.

$^1$H-NMR (CDCl$_3$, δppm): 0.24 (s, 54H), 7.77 (t, J=1.3 Hz, 3H), 7.83 (d, J=1.3 Hz, 6H)

$^{13}$C-NMR (CDCl$_3$, δppm): −1.11, 131.15, 138.72 and 140.30, 140.46

Mass Spec (EI-MS, m/z): 726 (M$^+$)

Synthesis of 1-tris{3,5-bis(trimethylsilyl)phenyl}silyl-2,3,4,5-tetramethylcyclopentadiene Under a nitrogen atmosphere, to potassium hydride dispersed in mineral oil (1.19 g, 29.78 mmol in terms of potassium hydride), tetrahydrofuran (108 mL) was added. This mixture was warmed to 50° C. and a solution of 1,2,3,4-tetramethylcyclopenta-1,3-diene (2.73 g, 22.34 mmol) dissolved in tetrahydrofuran (27 mL) was added dropwise. Stirring was performed at 50° C. for 1 hour. To this solution, a solution of chlorotris{3,5-bis(trimethysilyl)phenyl}silane (13.55 g, 18.62 mmol) dissolved in tetrahydrofuran (27 mL) was added dropwise and stirred at 50° C. for 5 hours. The resultant mixture was added dropwise at 0° C. to a solution of 10% sodium hydrogen carbonate (68 ml) and 10% sodium carbonate (68 mL). Toluene (68 mL) was added to separate an organic phase. After dried over sodium sulfate, the organic phase was filtrated. The solvent was removed under reduced pressure. Hexane was added and the obtained white solid was filtrated to obtain 1-tris{3,5-bis(trimethylsilyl)phenyl}silyl-2,3,4,5-tetramethylcyclopentadiene (7.01 g, yield 46.2%).

$^1$H-NMR (CDCl$_3$, δppm): 0.23 (s, 54H), 1.47 (s, 6H), 1.53 (s, 6H), 3.83 (s, 1H), 7.64 (t, J=1.3 Hz, 3H), 7.80 (d, J=1.3 Hz, 6H)

$^{13}$C-NMR (CDCl$_3$, δppm): −0.97, 11.16, 14.98, 51.01, 132.27, 132.80, 136.71, 137.62, 138.81, 140.98

Mass Spec (FD-MS, m/z): 813 (M$^+$)

"Synthesis of complex 3"

Under a nitrogen atmosphere, to a toluene solution (30 mL) of 1-tris{3,5-bis(trimethylsilyl)phenyl}silyl-2,3,4,5-tetramethylcyclopentadiene (1.48 g, 1.82 mmol) and triethylamine (0.92 g, 9.08 mmol), a 1.65 M hexane solution of n-butyllithium (1.32 mL, 2.18 mmol) was added dropwise at −78° C. The mixture was gradually warmed to room temperature and stirring was performed at 50° C. for 8 hours. The obtained mixture was cooled to −78° C. and a solution of titanium(IV) chloride (0.38 g, 2.00 mmol) dissolved in toluene (2 mL) was added dropwise at the same temperature. The mixture was warmed again and stirring was performed overnight at room temperature. After completion of the reaction, the solvent was removed under reduced pressure. Thereafter, heptane was added to the residue, and insoluble materials were removed by filtration. The solvent was removed from the filtrate under reduced pressure. Pentane was added, and the obtained solid was filtrated and washed with a small amount of pentane and dried under reduced pressure to obtain complex 3 (0.10 g, yield 5.7%) as a yellow ocherous solid.

$^1$H-NMR (CDCl$_3$, δppm): 0.19 (s, 54H), 1.95 (s, 6H), 2.34 (s, 6H), 7.71 (s, 3H), 7.77 (s, 6H)

$^{13}$C-NMR (CDCl$_3$, δppm): −1.10, 14.18, 17.40, 65.86, 130.98, 138.47, 139.58, 142.16, 142.53, 145.70

Mass Spec (EI-MS, m/z): 966 (M$^-$)

Example 4

Synthesis of [1-tris(3-trimethylsilyl-phenyl)silyl-2,3,4,5-tetramethylcyclopentadienyl]titanium trichloride (hereinafter referred to as "complex 1")

Synthesis of [1-tris(3-trimethylsilyl-phenyl)silyl-2,3,4,5-tetramethylcyclopentadienyl]titaniumtriisopropoxide Under a nitrogen atmosphere, potassium hydride dispersed in mineral oil was washed with hexane to remove the mineral oil. Thereafter the resultant potassium hydride (0.13 g, 3.25 mmol) and tetrahydrofuran (34 mL) were mixed. To the mixture a solution of 1-tris(3-trimethylsilyl-phenyl)silyl-2,3,4,5-tetramethylcyclopentadiene (1.49 g, 2.50 mmol) dissolved in tetrahydrofuran (11 mL) was added dropwise and stirred at 50° C. for 6 hours. The resultant mixture was cooled to room temperature and filtrated to remove insoluble materials. The obtained filtrate was cooled to −78° C. and a solution of chlorotriisopropoxytitanium (0.65 g, 2.50 mmol) dissolved in tetrahydrofuran (7 mL) was added dropwise at the same temperature. The mixture was gradually warmed to room temperature and stirring was performed at room temperature overnight. After completion of the reaction, the solvent was removed under reduced pressure. Thereafter, pentane was added to the residue, and insoluble materials were removed by filtration. Removal of the solvent from the filtrate under reduced pressure quantitatively gave [1-tris(3-trimethylsilyl-phenyl)silyl-2,3,4,5-tetramethylcyclopentadienyl]titaniumisopropoxide as an orange oil.

$^1$H-NMR (CDCl$_3$, δppm): 0.15 (s, 27H), 1.09 (d, J=6.2 Hz, 18H), 1.66 (s, 6H), 1.99 (s, 6H), 4.53 (sep, J=6.2 Hz, 3H), 7.31 (t, J=7.3 Hz, 3H), 7.50 (d, J=7.3 Hz, 3H), 7.61 (s, 3H), 7.82 (d, 7.3 Hz, 3H)

$^{13}$C-NMR (CDCl$_3$, δppm): −1.13, 11.65, 15.01, 26.44, 75.63, 112.20, 126.60, 131.54, 133.70, 135.54, 136.12, 137.70, 138.44, 141.38

Mass Spec (EI-MS, m/z): 820 (M$^+$)

"Synthesis of complex 1"

Under a nitrogen atmosphere, to a toluene solution (42 mL) of [1-tris(3-trimethylsilyl-phenyl)silyl-2,3,4,5-tetramethylcyclopentadienyl]titaniumtriisopropoxide (2.05 g, 2.50 mmol), a solution of silicon tetrachloride (4.25 g, 25.00 mmol) dissolved in toluene (21 mL) was added dropwise at 0° C. The mixture was gradually warmed to room temperature and stirring was performed at room temperature for 3 hours. After completion of the reaction, the solvent was removed under reduced pressure. Heptane was added to the residue, and insoluble materials were removed by filtration. The solvent was removed from the filtrate under reduced pressure and recrystallization was performed from pentane to obtain complex 1 as an orange solid (0.30 g, yield 15.8%).

$^1$H-NMR (CDCl$_3$, δppm): 0.21 (s, 27H), 2.01 (s, 6H), 2.35 (s, 6H), 7.34 (t, J=7.3 Hz, 3H), 7.53 (dt, J=7.3, 1.4 Hz, 3H), 7.59 (dt, J=7.3, 1.4 Hz, 3H), 7.86 (s, 3H)

$^{13}$C-NMR (CDCl$_3$, δppm): −1.19, 14.32, 17.59, 127.14, 132.00, 134.89, 136.08, 137.06, 139.83, 142.08, 142.44, 145.76

Mass Spec (EI-MS, m/z): 750 (M$^-$)

Example 5

Synthesis of [1-tris(5-methyl-3-trimethylsilyl-phenyl)silyl-2,3,4,5-tetramethylcyclopentadienyl]titanium trichloride (hereinafter, referred to as "complex 2")

Synthesis of [1-tris(5-methyl-3-trimethylsilyl-phenyl)silyl-2,3,4,5-tetramethylcyclopentadienyl]titanium triisopropoxide Under a nitrogen atmosphere, potassium hydride dispersed in mineral oil was washed with hexane to remove the mineral oil. Thereafter, the resultant potassium hydride (0.29 g, 7.24 mmol) and tetrahydrofuran (36 mL) were mixed. This mixture was warmed to 50° C. and a solution of 1-tris(5-methyl-3-trimethylsilyl-phenyl)silyl-2,3,4,5-tetramethylcyclopentadiene (3.56 g, 5.57 mmol) dissolved in tetrahydrofuran (19 mL) was added dropwise and stirred at 50° C. for 6 hours. The resultant mixture was cooled to room temperature and insoluble materials were removed by filtration. The resultant filtrate was cooled to −78° C. and a solution of chlorotriisopropoxytitanium (1.45 g, 5.57 mmol) dissolved in tetrahydrofuran (10 mL) was added dropwise at the same temperature. After the mixture was gradually warmed to room temperature, stirring was performed at room temperature overnight. After completion of the reaction, the solvent was removed under reduced pressure. Thereafter, pentane was added to the residue, and insoluble materials were removed by filtration. The solvent was removed from the filtrate under reduced pressure to quantitatively obtain [1-tris(5-methyl-3-trimethylsilyl-phenyl)silyl-2,3,4,5-tetramethylcyclopentadienyl]titanium triisopropoxide as a light yellow solid.

$^1$H-NMR (CDCl$_3$, δ ppm): 0.14 (s, 27H), 1.08 (d, J=6.2 Hz, 18H), 1.67 (s, 6H), 1.98 (s, 6H), 2.32 (s, 9H), 4.50 (quin, J=6.2 Hz, 3H), 7.29 (s, 3H), 7.37 (s, 3H), 7.62 (s, 3H)

$^{13}$C-NMR (CDCl$_3$, δ ppm): −1.12, 11.62, 15.03, 21.70, 26.52, 75.66, 112.59, 126.69, 131.28, 134.41, 135.28, 135.52, 138.17, 138.94

Mass Spec (EI-MS, m/z): 862 (M$^+$)

"Synthesis of Complex 2"

Under a nitrogen atmosphere, to a toluene solution (96 mL) of [1-tris(5-methyl-3-trimethylsilyl-phenyl)silyl-2,3,4,5-tetramethylcyclopentadienyl]titanium triisopropoxide (4.81 g, 5.57 mmol), a solution of silicon tetrachloride (9.47 g, 55.71 mmol) dissolved in toluene (56 mL) was added dropwise at 0° C. After the mixture was gradually warmed to room temperature, stirring was performed at room temperature for 3 hours. After completion of the reaction, the solvent was removed under reduced pressure. Thereafter, heptane was added to the residue, and insoluble materials were removed by filtration. The solvent was removed from the filtrate under reduced pressure and recrystallization from pentane gave complex 2 (1.07 g, yield 24.4%) as an orange solid.

$^1$H-NMR(CDCl$_3$, δ ppm): 0.19 (s, 27H), 2.02 (s, 6H), 2.30 (s, 9H), 2.35 (s, 6H), 7.38 (s, 3H), 7.41 (s, 3H), 7.59 (s, 3H)

$^{13}$C-NMR (CDCl$_3$, δ ppm): −1.17, 14.32, 17.63, 21.61, 131.94, 135.51, 136.11, 137.05, 137.78, 139.21, 139.44, 142.43, 145.83

Mass Spec (EI-MS, m/z): 792 (M$^-$)

Example 6

Synthesis of [1-tris(5-methyl-3-trimethylsilyl-phenyl)silyl-2,3,4,5-tetramethylcyclopentadienyl]trimethyltitanium (hereinafter, referred to as "complex 4")

Under a nitrogen atmosphere, to a diethyl ether solution (22 mL) of [1-tris(5-methyl-3-trimethylsilyl-phenyl)silyl-2, 3,4,5-tetramethylcyclopentadienyl]titanium trichloride (complex 2) (446 mg, 0.56 mmol), a 3.00 M diethyl ether solution of methylmagnesium iodide (0.94 mL, 2.81 mmol) was added dropwise at −20° C. The mixture was gradually warmed to room temperature while stirring. After completion of the reaction, the solvent was removed under reduced pressure. Thereafter, hexane was added to the residue, and insoluble materials were removed by filtration. The solvent was removed from the filtrate under reduced pressure. Recrystallization from pentane gave complex 4 (370 mg, yield 89.9%) as a light yellow solid.

$^1$H-NMR (CD$_2$Cl$_2$, δ ppm): 0.19 (s, 27H), 0.94 (s, 9H), 1.58 (s, 6H), 1.95 (s, 6H), 2.28 (s, 9H), 7.35 (s, 6H), 7.50 (s, 3H)

$^{13}$C-NMR (CD$_2$Cl$_2$, δ ppm): 1.05, 12.38, 15.39, 21.68, 63.59, 118.06, 129.34, 130.47, 134.76, 135.29, 136.29, 138.09, 139.40

<Production of 1-hexene>

(1) Trimerization Activity

Trimerization activity was analyzed by using gas chromatography (Shimadzu GC-2010, DB-1 column).

(2) Synthesis of Known Transition Metal Complex

[Dimethylphenylsilylcyclopentadienyl]titanium trichloride (hereinafter, referred to as "complex 5") was synthesized by following a known method (J. Organomet. Chem. 1999, 592, 84-94). [1-(1-methyl-1-(3,5-dimethylphenyl)ethyl)-3-trimethylsilylcyclopentadienyl]titanium trichloride (hereinafter, referred to as "complex 6") was synthesized by following a known method (Organometallics 2002, 21, 5122-5135).

Example 7

An autoclave (0.4 liter) equipped with a stirrer was dried under reduced pressure and purged with argon. Toluene (60 mL) and a toluene solution (0.88 mL) of methylaluminoxane (TMAO-s manufactured by Tosoh Finechem Corp.) having an Al concentration of 9.0 wt % (3.5 mmol/mL) were supplied to the autoclave and the interior temperature of the system was increased to 40° C. Thereafter, ethylene was introduced so as to obtain a partial pressure of 0.5 MPa to stabilize the system. To this, 0.60 mL of a toluene solution of the complex 1 mixture obtained in Example 1 (complex 1 concentration: 1 μmol/mL) was added. A reaction was performed at 40° C. for 30 minutes while continuously supplying ethylene gas so as to maintain the whole pressure at a constant value. Ethanol (1.0 mL) was added so as to stop the reaction. Thereafter, ethylene was purged and the content of the autoclave was decalcificated with ethanol-hydrochloric acid and then filtrated. 1-Hexene and polymers were obtained. The trimerization activity was 10.70×10$^6$ g/mol complex/h and the polymerization activity was 0.26×10$^6$ g/mol complex/h.

Example 8

An autoclave (0.4 liter) equipped with a stirrer was dried under reduced pressure and purged with argon. Toluene (60 mL) and a toluene solution (0.88 mL) of methylaluminoxane (TMAO-s manufactured by Tosoh Finechem Corp.) having an Al concentration of 9.0 wt % (3.5 mmol/mL) were supplied to the autoclave and the interior temperature of the system was increased to 40° C. Thereafter, ethylene was introduced so as to obtain a partial pressure of 0.5 MPa to stabilize the system. To this, 0.60 mL, of a toluene solution of the complex 2 mixture obtained in Example 2 (complex 2 concentration: 1 μmol/mL) was added. A reaction was performed at 40° C. for 30 minutes while continuously supplying ethylene gas so as to maintain the whole pressure at a constant value. Ethanol (1.0 mL) was added so as to stop the reaction. Thereafter, ethylene was purged and the content of the autoclave was decalcificated with ethanol-hydrochloric acid and then filtrated. 1-Hexene and polymers were obtained. The trimerization activity was 7.39×10$^6$ g/mol complex/h and the polymerization activity was 0.10×10$^6$ g/mol complex/h.

Example 9

An autoclave (0.4 liter) equipped with a stirrer was dried under reduced pressure and purged with argon. Toluene (90 mL) and a toluene solution (0.74 mL) of methylaluminoxane (TMAO-s manufactured by Tosoh Finechem Corp.) having an Al concentration of 9.0 wt % (3.4 mmol/mL) were supplied to the autoclave and the interior temperature of the system was increased to 80° C. Thereafter, ethylene was introduced so as to obtain a partial pressure of 0.5 MPa to stabilize the system. To this, 1.0 mL of a toluene solution of complex 1 obtained in Example 4 (1 μmol/mL) was added. A reaction was performed at 80° C. for 30 minutes while continuously supplying ethylene gas so as to maintain the whole pressure at a constant value. Ethanol (1.0 mL) was added so as to stop the reaction. Thereafter, ethylene was purged and the content of the autoclave was decalcificated with ethanol-hydrochloric acid and then filtrated. 1-Hexene and polymers were obtained. The trimerization activity was 1.55×10$^6$ g/mol complex/h and the polymerization activity was 0.02×10$^6$ g/mol complex/h.

Example 10

An autoclave (0.4 liter) equipped with a stirrer was dried under reduced pressure and purged with argon. Toluene (90 mL) and a toluene solution (0.74 mL) of methylaluminoxane (TMAO-s manufactured by Tosoh Finechem Corp.) having an Al concentration of 9.0 wt % (3.4 mmol/mL) were supplied to the autoclave and the interior temperature of the system was increased to 80° C. Thereafter, ethylene was introduced so as to obtain a partial pressure of 0.5 MPa to stabilize the system. To this, 1.0 mL of a toluene solution of complex 2 obtained in Example 5 (1 μmol/mL) was added. A reaction was performed at 80° C. for 30 minutes while continuously supplying ethylene gas so as to maintain the whole pressure at a constant value. Ethanol (1.0 mL) was added so as to stop the reaction. Thereafter, ethylene was purged and the content of the autoclave was decalcificated with ethanol-hydrochloric acid and then filtrated. 1-Hexene and polymers were obtained. The trimerization activity was 2.85×10$^6$ g/mol complex/h and the polymerization activity was 0.03×10$^6$ g/mol complex/h.

Example 11

An autoclave (0.4 liter) equipped with a stirrer was dried under reduced pressure and purged with argon. Toluene (60 mL) and a toluene solution (0.83 mL) of methylaluminoxane (TMAO-s manufactured by Tosoh Finechem Corp.) having an Al concentration of 9.4 wt % (3.6 mmol/mL) were supplied to the autoclave and the interior temperature of the system was increased to 40° C. Thereafter, ethylene was introduced so as to obtain a partial pressure of 0.5 MPa to stabilize the system. Separately from this, complex 4 obtained in Example 6 was dissolved in a TIBA toluene solution adjusted to 10 mmol/L so as to give a complex concentration of 1 mmol/L. 0.60 mL of this toluene solution was added to the autoclave. A reaction was performed at 40° C. for 30 minutes while continuously supplying ethylene gas so as to maintain the whole pressure at a constant value. After ethanol (1.0 mL) was added so as to stop the reaction. Thereafter, ethylene was purged and the content of the autoclave was decalcificated with ethanol-hydrochloric acid and then filtrated. 1-Hexene and polymers were obtained. The trimerization activity was 7.52×10⁶ g/mol complex/h and the polymerization activity was 0.11×10⁶ g/mol complex/h.

Comparative Example 1

The same operation was performed as in Example 7 except that complex 5 was used in place of complex 1. As a result, 1-hexene and polymers were obtained. The trimerization activity was 0.35×10⁶ g/mol complex/h and the polymerization activity was 0.13×10⁶ g/mol complex/h.

Comparative Example 2

The same operation was performed as in Example 7 except that complex 6 was used in place of complex 1. As a result, 1-hexene and polymers were obtained. The trimerization activity was 4.17×10⁶ g/mol complex/h and the polymerization activity was 0.06×10⁶ g/mol complex/h.

Comparative Example 3

The same operation was performed as in Example 9 except that complex 5 was used in place of complex 1. As a result, 1-hexene and polymers were obtained. The trimerization activity was 0.06×10⁶ g/mol complex/h and the polymerization activity was 0.02×10⁶ g/mol complex/h.

Comparative Example 4

The same operation was performed as in Example 9 except that complex 6 was used in place of complex 1. As a result, 1-hexene and polymers were obtained. The trimerization activity was 0.43×10⁶ g/mol complex/h and the polymerization activity was 0.07×10⁶ g/mol complex/h.

The invention claimed is:
1. A transition metal complex represented by formula (1):

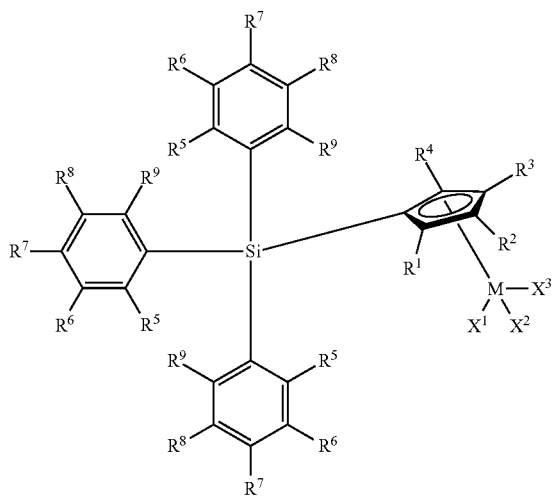

(1)

wherein
M represents a transition metal atom of Group 4 of the Periodic Table of the Elements;
$X^1$, $X^2$, $X^3$, $R^1$, $R^2$, $R^3$, $R^4$, $R^6$, $R^7$, $R^8$ and $R^9$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by $—Si(R^{10})_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20, or
a disubstituted amino group represented by $—N(R^{11})_2$, wherein the two $R^{11}$ moieties each independently represent a hydrocarbyl group or a halogenated hydrocarbyl group, and the total number of the carbon atoms in the two $R^{11}$ moieties is 2 to 20, and
at least one of $R^5$, $R^6$, $R^7$, $R^8$ and $R^9$ is the alkoxy group, the aryloxy group, the aralkyloxy group, the substituted silyl group or the disubstituted amino group; or
of $R^1$, $R^2$, $R^3$ and $R^4$, two group bonded to two adjoining carbon atoms may be bonded to each other to form a ring together with the two carbon atoms to which the two groups are bonded, and of $R^5$, $R^6$, $R^7$, $R^8$ and $R^9$, two group bonded to two adjoining carbon atoms may be bonded to each other to form a ring together with the two carbon atoms to which the two groups are bonded.

2. The transition metal complex represented by formula (1) according to claim 1, wherein M is a titanium atom.

3. The transition metal complex represented by formula (1) according to claim 1, wherein $R^1$, $R^2$, $R^3$ and $R^4$ are each a methyl group.

4. The transition metal complex represented by formula (1) according to claim 1, wherein $R^6$ is
a substituted silyl group represented by $—Si(R^{10})_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20.

5. The transition metal complex represented by formula (1) according to claim 1, wherein $R^6$ and $R^8$ are a substituted silyl group represented by $—Si(R^{10})_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20.

6. The transition metal complex represented by formula (1) according to claim 1, wherein $R^6$ is a substituted silyl group represented by $—Si(R^{10})_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20, and $R^8$ is an alkyl group having 1 to 20 carbon atoms which may have a halogen atom as a substitute.

7. A catalytic component for trimerization comprising a transition metal complex according to claim 1.

8. A catalyst for trimerization which is obtained by bringing a transition metal complex according to claim 1, into contact with an activating co-catalyst component.

9. The catalyst for trimerization according to claim 8, wherein the activating co-catalyst component comprises the following compound (A):
compound (A): one or more aluminum compounds selected from the compound group consisting of the following compounds (A1), (A2) and (A3):
(A1): an organic aluminum compound represented by formula $(E^1)_a Al(G)_{3-a}$,
(A2): cyclic aluminoxane having a structure represented by formula $\{-Al(E^2)-O—\}_b$, and
(A3): linear aluminoxane having a structure represented by formula $E^3\{-Al(E)-O—\}_c Al(E)_2$, wherein $E^1$, $E^2$ and $E^3$ each independently represent a hydrocarbyl group having 1 to 8 carbon atoms; G represents a hydrogen atom or a halogen atom; a represents an integer of 1 to 3; b represents an integer of 2 or more; c represents an integer of 1 or more; in the case that more than one $E^1$ moieties exist, the $E^1$ moieties may be the same as or different from each other; in the case that more than one G moieties exist, the G moieties may be the same as or different from each other; a plurality of $E^2$ moieties may be the same as or different from each other; and a plurality of $E^3$ moieties may be the same as or different from each other.

10. The catalyst for trimerization according to claim 8, wherein the activating co-catalyst component comprises the following compound (B):

compound (B): one or more boron compounds selected from the compound group consisting of the following compounds (B1), (B2) and (B3):

(B1): a boron compound represented by formula $BQ^1Q^2Q^3$, (B2): a borate compound represented by formula $T^+(BQ^4Q^5Q^6)^-$, and (B3): a borate compound represented by formula $(L\text{-}H)^+(BQ^8Q^9Q^{10}Q^{11})^-$, B represents a trivalent boron; $Q^1$, $Q^2$, $Q^3$, $Q^4$, $Q^5$, $Q^6$, $Q^7$, $Q^8$, $Q^9$, $Q^{10}$ and $Q^{11}$ the same as or different from each other and each independently represent a halogen atom, a hydrocarbyl group having 1 to 20 carbon atoms which may have a halogen atom as a substituent, a hydrocarbylsilyl group having 1 to 20 carbon atoms which may have a halogen atom as a substituent, an alkoxy group having 1 to 20 carbon atoms which may have a halogen atom as a substituent or a dihydrocarbylamino group having 2 to 20 carbon atoms which may have a halogen atom as a substituent; $T^+$ represents an inorganic or organic cation; and $(L\text{-}H)^+$ represents Broensted acid.

11. A method for producing 1-hexene by ethylene trimerization in the presence of a catalyst for trimerization according to claim 8.

12. A production method of the transition metal complex represented by formula (1) according to claim 1, comprising the steps of:

reacting a substituted cyclopentadiene compound represented by formula (2) with a base in the presence of an amine compound;

(2)

[Chemical structure showing substituted biphenyl-silyl-cyclopentadiene compound with substituents $R^1$ through $R^9$]

wherein $R^1$, $R^2$, $R^3$, $R^4$, $R^5$, $R^6$, $R^7$, $R^8$ and $R^9$ are as defined above, the moiety

[Chemical structure showing Si-cyclopentadiene with $R^1$, $R^2$, $R^3$, $R^4$]

represents

[Five chemical structures showing Si-cyclopentadiene tautomers with $R^1$, $R^2$, $R^3$, $R^4$]

and reacting the reaction product of the substituted cyclopentadiene compound (2) and the base with a transition metal compound represented by formula (3):

$$X^1\underset{X^2}{\overset{}{\diagup}}M\underset{X^3}{\overset{(X^4)_m}{\diagdown}} \quad (3)$$

wherein M, $X^1$, $X^2$ and $X^3$ are as defined above; and $X^4$ represents a hydrogen atom, a halogen atom, an alkyl group having 1 to 20 carbon atoms which may have a halogen atom as a substituent, an alkoxy group having 1 to 20 carbon atoms which may have a halogen atom as a substituent, an aryl group having 6 to 20 carbon atoms which may have a halogen atom as a substituent, an aryloxy group having 6 to 20 carbon atoms which may have a halogen atom as a substituent, an aralkyl group having 7 to 20 carbon atoms which may have a halogen atom as a substituent, an aralkyloxy group having 7 to 20 carbon atoms which may have a halogen atom as a substituent, a substituted silyl group represented by $-\text{Si}(R^{10})_3$, wherein the three $R^{10}$ moieties each independently represent a hydrogen atom, a hydrocarbyl group or a halogenated hydrocarbyl group, and the total number of the carbon atoms in the three $R^{10}$ moieties is 1 to 20, or a disubstituted amino group represented by $-\text{N}(R^{11})_2$, wherein the two $R^{11}$ moieties each independently represent a hydrocarbyl group or a halogenated hydrocarbyl group, and the total number of the carbon atoms in the two $R^{11}$ moieties is 2 to 20, and m represents 0 or 1.

13. A substituted cyclopentadiene compound represented by formula (2)

(2)

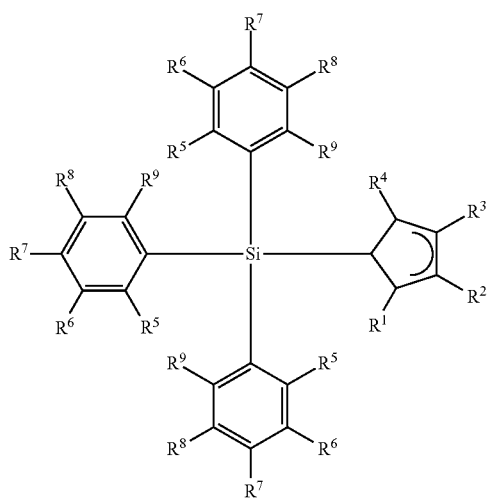

wherein
$R^1$, $R^2$, $R^3$, $R^4$, $R^5$, $R^6$, $R^7$, $R^8$ and $R^9$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{10}$)$_3$, wherein the three $R^1$ moieties each independently represent a hydrogen atom, a hydrocarbyl group or a halogenated hydrocarbyl group, and the total number of the carbon atoms in the three $R^{10}$ moieties is 1 to 20, or
a disubstituted amino group represented by —N($R^{11}$)$_2$, wherein the two $R^{11}$ moieties each independently represent a hydrocarbyl group or a halogenated hydrocarbyl group, and the total number of the carbon atoms in the two $R^{11}$ moieties is 2 to 20, and
at least one of $R^5$, $R^6$, $R^7$, $R^8$ and $R^9$ is the alkoxy group, the aryloxy group, the aralkyloxy group, the substituted silyl group or the disubstituted amino group; or
of $R^1$, $R^2$, $R^3$ and $R^4$, two groups bonded to two adjoining carbon atoms may be bonded to each other to form a ring together with the two carbon atoms to which the two groups are bonded, and of $R^5$, $R^6$, $R^7$, $R^8$ and $R^9$, two groups bonded to two adjoining carbon atoms may be bonded to each other to form a ring together with the two carbon atoms to which the two groups are bonded,
the moiety

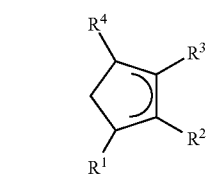

represents

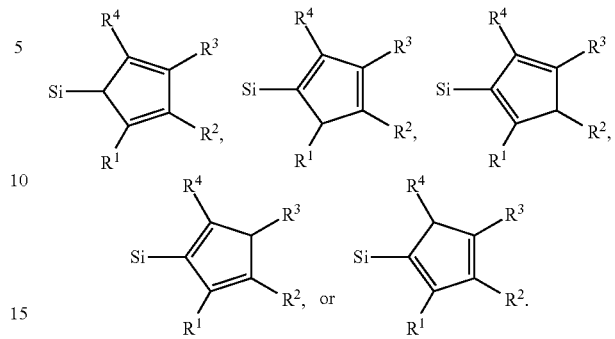

14. A method for producing a substituted cyclopentadiene compound represented by formula (2) according to claim 13, comprising the steps of
reacting a substituted cyclopentadiene compound represented by formula (4) with a base.

(4)

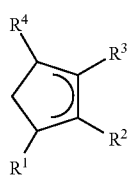

wherein $R^1$, $R^2$, $R^3$ and $R^4$ are as defined above, and
the moiety

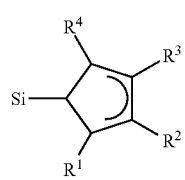

represents

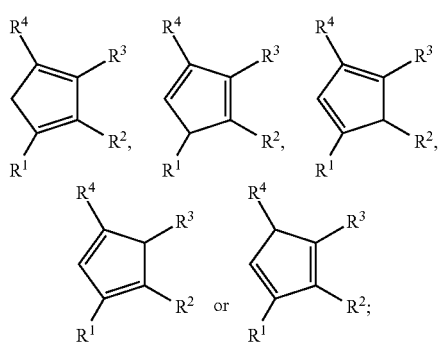

and
reacting the reaction product of the substituted cyclopentadiene compound (4) and the base with a halogenated silyl compound represented by formula (5):

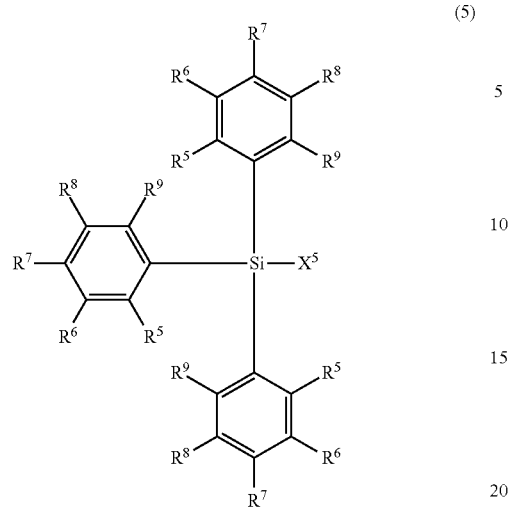
(5)
wherein $R^5$, $R^6$, $R^7$, $R^8$ and $R^9$ are as defined above, and $X^5$ is a halogen atom.
* * * * *